(12) United States Patent
Meares et al.

(10) Patent No.: US 7,267,994 B2
(45) Date of Patent: *Sep. 11, 2007

(54) ELEMENT-CODED AFFINITY TAGS

(75) Inventors: Claude F. Meares, Davis, CA (US); Carlito B. Lebrilla, Davis, CA (US); Nathaniel G. Butlin, Davis, CA (US); Sarah M. Cheal, Davis, CA (US); Todd M. Corneillie, Berkeley, CA (US); Susan Lee, Woodland, CA (US); Paul A. Whetstone, Davis, CA (US); Nicolas L. Young, Richmond, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/854,735

(22) Filed: May 24, 2004

(65) Prior Publication Data
US 2005/0042695 A1    Feb. 24, 2005

Related U.S. Application Data

(63) Continuation-in-part of application No. 10/835,533, filed on Apr. 28, 2004.

(60) Provisional application No. 60/495,449, filed on Aug. 15, 2003, provisional application No. 60/466,529, filed on Apr. 28, 2003.

(51) Int. Cl.
| G01N 33/532 | (2006.01) |
| G01N 33/24 | (2006.01) |
| G01N 24/00 | (2006.01) |
| G01N 33/53 | (2006.01) |
| C07K 1/14 | (2006.01) |
| C07D 257/02 | (2006.01) |

(52) U.S. Cl. .................. 436/544; 436/81; 436/82; 436/96; 436/173; 435/6; 435/7.1; 435/7.5; 435/7.92; 435/810; 435/975; 435/973; 530/405; 530/412; 540/474

(58) Field of Classification Search .............. 540/474; 530/402, 409, 391.5, 405, 412; 436/544, 436/81, 82, 96, 173; 424/9.363, 1.53; 435/7.9, 435/6, 7.1, 7.5, 7.92, 810, 975, 973
See application file for complete search history.

(56) References Cited

U.S. PATENT DOCUMENTS 5,760,191 A * 6/1998 Snow et al. ................. 534/10

FOREIGN PATENT DOCUMENTS

WO   WO 00/11208 A1   3/2000

OTHER PUBLICATIONS

Liu et al. Radiolabeling of monoclonal antibodies with metal chelates. Pure & Appl. Chem., 1991, vol. 63, No. 3, pp. 427-463.*

(Continued)

*Primary Examiner*—Long V. Le
*Assistant Examiner*—Shafiqul Haq
(74) *Attorney, Agent, or Firm*—Townsend and Townsend and Crew LLP

(57) ABSTRACT

The present invention provides compositions and methods for detecting, analyzing, and identifying biomolecules. More particularly, the invention provides Element Coded Affinity Tags comprising a metal chelate and a metal ion and methods of using the tags to detect, analyze, and identify biomolecules including polypeptides, nucleic acids, lipids, and polysaccharides.

27 Claims, 29 Drawing Sheets

OTHER PUBLICATIONS

Kramerov, A.A., et al., "Tissue Localization and Secretion of Mucin-D in *Drosophila melanogaster*," *Russian Journal of Developmental Biology* (1997) 28(4): 227-234.

Aebersold, et al.; "Mass Spectrometry-based Proteomics;" *Nature*; Mar. 2003; pp. 198-207; vol. 422.

Butterfield, et al.; "Proteomics for the Identification of Specifically Oxidized Proteins in Brain: Technology and Application to the Study of Neurodegenerative Disorders;" *Amino Acids*; 2003; pp. 419-425; vol. 25; Austria.

Butterfield; "Proteomics: A New Approach to Investigate Oxidative Stress in Alzheimer's Disease Brain;" *Brain Research*; 2004; pp. 1-7; vol. 1000; Elsevier B.V.

Dalle-Donne, et al.; "Protein Carbonylation in Human Diseases;" *TRENDS in Molecular Medicine*; Apr. 2003; pp. 169-176; vol. 9; No. 4; Elsevier Science Ltd.

Gygi, et al.; "Mass Spectrometry and Proteomics;" *Current Opinion in Chemical Biology*; 2000; pp. 489-494; vol. 4.

Gygi, et al.; "Proteome Analysis of Low-Abundance Proteins Using Multidimensional Chromatography and Isotope-Coded Affinity Tags;" *Journal of Proteome Research*; Jan. 18, 2002; pp. 47-54; vol. 1; American Chemical Society.

Gygi, et al.; "Quantitative Analysis of Complex Protein Mixtures Using Isotope-coded Affinity Tags;" *Nature Biotechnology*; Oct. 1999; pp. 994-999; vol. 17.

Himmelfarb, et al.; "Albumin is the Major Plasma Protein Target of Oxidant Street in Uremia;" *Kidney International*; 2001; pp. 358-363; vol. 60; International Society of Nephrology.

Odetti, et al.; "Levels of Carbonyl Groups in Plasma Proteins of Type 2 Diabetes Mellitus Subjects;" *Acta Diabetol*; 1999; pp. 179-183; vol. 36.

Patterson, et al.; "Proteomics: The First Decade and Beyond;" *Nature Genetics Supplement*; Mar. 2003; pp. 311-323; vol. 33.

Ranish, et al.; "The Study of Macromolecular Complexes by Quantitative Proteomics;" *Nature Genetics*; Mar. 2003; pp. 349-355; vol. 33.

Tao, et al.; "Advances in Quantitative Proteomics Via Stable Isotope Tagging and Mass Spectrometry;" *Current Opinion in Biotechnology*; 2003; pp. 110-118; vol. 14.

Zhou, et al.; "Quantitative Proteome Analysis by Solid-Phase Isotope Tagging and Mass Spectrometry;" *Nature Biotechnology*; May 2002; pp. 512-515; vol. 20.

* cited by examiner

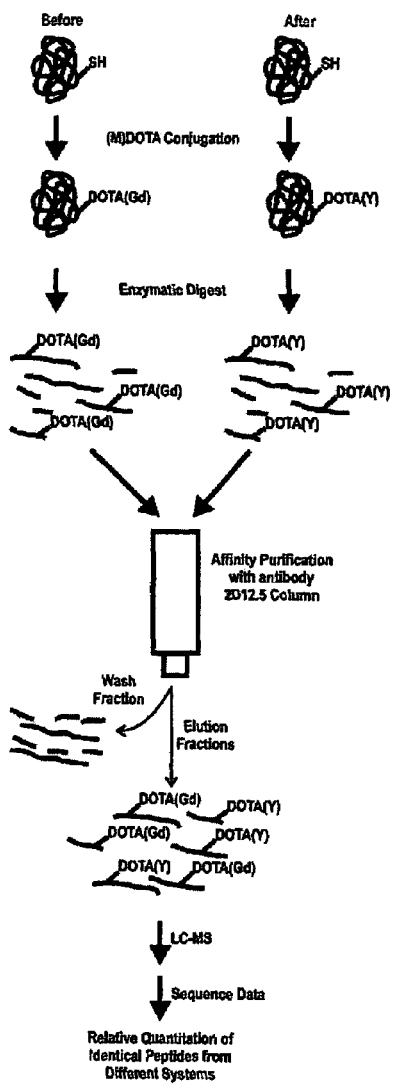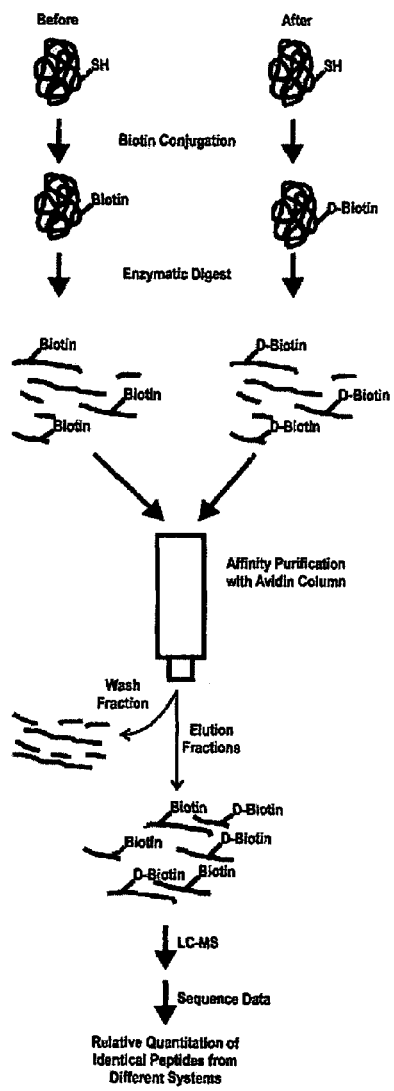
Figure 1

FIG. 3

R indicates one of the reactive groups below

Exemplary Sulfhydryl Reactive Groups:

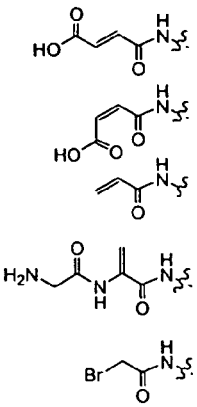

Exemplary Amine Reactive Groups:

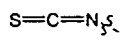

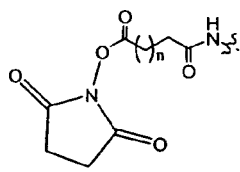

Exemplary Carbonyl Reactive Groups:

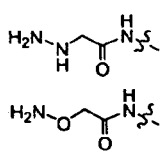

Exemplary bifunctional chelating agents:

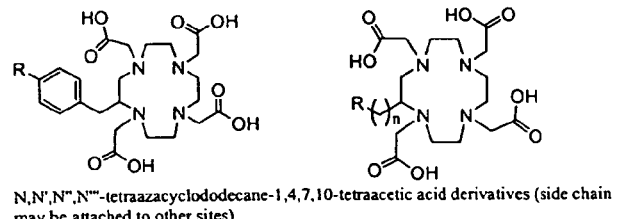

N,N',N",N'''-tetraazacyclododecane-1,4,7,10-tetraacetic acid derivatives (side chain may be attached to other sites)

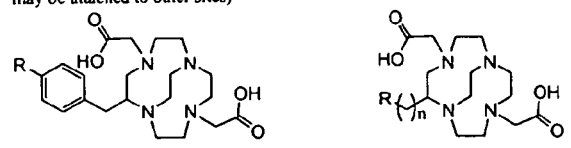

4,10-bis(carboxymethyl)-1,4,7,10-tetraazabicyclo[5.5.2]tetradecane derivatives (side chain may be attached to other sites)

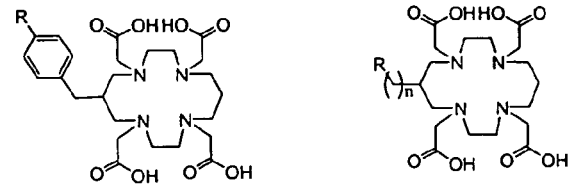

N,N',N",N'''-tetraazacyclotetradecane-1,4,8,11-tetraacetic acid derivatives (side chain may be attached to other sites)

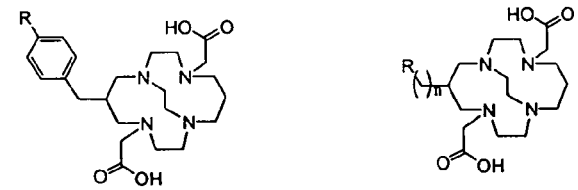

4,11-bis(carboxymethyl)-1,4,8,11-tetraazabicylco[6.6.2]hexadecane derivatives (side chain may be attached to other sites)

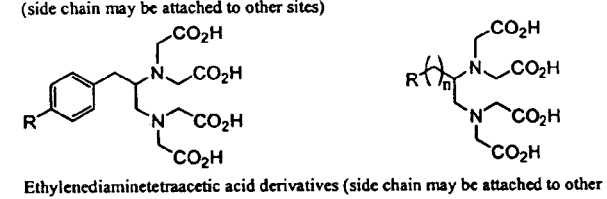

Ethylenediaminetetraacetic acid derivatives (side chain may be attached to other sites)

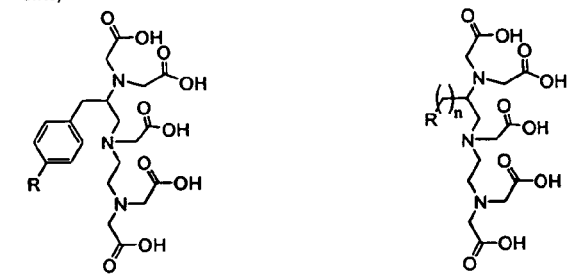

Diethylenetriaminepentaacetic acid derivatives (side chain may be attached to other sites)

FIG. 5A

| Element | Isotope | Abundance[1] |
|---|---|---|
| Y | 89 | 100.00 |
| La | 139 | 100.00 |
| Ce | 136 | 0.2 |
| | 138 | 0.2 |
| | 140 | 100.00 |
| | 142 | 12.5 |
| Pr | 141 | 100.00 |
| Nd | 142 | 100.00 |
| | 143 | 44.8 |
| | 144 | 87.7 |
| | 145 | 30.6 |
| | 146 | 63.3 |
| | 148 | 21.1 |
| | 150 | 20.8 |
| Pm | No data | |
| Sm | 144 | 12.0 |
| | 147 | 58.3 |
| | 148 | 44.0 |
| | 149 | 53.7 |
| | 150 | 28.8 |
| | 152 | 100.00 |
| | 154 | 88.2 |
| Eu | 151 | 91.5 |
| | 153 | 100.00 |
| Gd | 152 | 0.8 |
| | 154 | 8.8 |
| | 155 | 59.6 |
| | 156 | 82.4 |
| | 157 | 63.0 |
| | 158 | 100.00 |
| | 160 | 88.0 |
| Tb | 159 | 100.00 |
| Dy | 156 | 0.2 |
| | 158 | 0.4 |
| | 160 | 8.3 |
| | 161 | 67.0 |
| | 162 | 90.4 |
| | 163 | 88.2 |
| | 164 | 100.00 |
| Ho | 165 | 100.00 |
| Er | 162 | 0.4 |
| | 164 | 4.7 |
| | 166 | 100.00 |
| | 167 | 68.2 |
| | 168 | 79.7 |
| | 170 | 44.2 |

FIG. 5B

| Element | Isotope | Abundance[1] |
|---|---|---|
| Tm | 169 | 100.00 |
| Yb | 168 | 0.4 |
|  | 170 | 9.5 |
|  | 171 | 45.0 |
|  | 172 | 68.9 |
|  | 173 | 50.7 |
|  | 174 | 100.00 |
|  | 176 | 39.8 |
| Lu | 175 | 100.00 |
|  | 176 | 2.7 |

[1]Decimal number is abundance relative to the most abundant, set at 100.00 sequence_AA_2D12.5_variable domains.txt

>2D12.5VL_MOUSE
(1) QAVVTQESALTTSPGETVTLTCRSSTGAVTTSNYANWVQEKPDHLFTGLIGGNNNRPPGVPARFSGSLIGDKAALTIAGTQTED
EAIYFCALWYSNHWVFGGGTRLTVLG (2) CDR1 - RSSTGAVTTSNYAN
(3) CDR2 - GNNNRPP
(4) CDR3 - ALWYSNHWV

>2D12.5VH_MOUSE
(5) QVKLQESGPGLVQPSQSLSITCTVSGFSLTDYGVHWVRQSPGKGLEWLGVIWSGGGTAYTAAFISRLNIY
KDNSKNQVFFEMNSLQANDTAMYYCARRGSYPYNYFDVWGQGTTVTSS (6) CDR1 - DYGVH
(7) CDR2 - VIWSGGGTAYTAAFIS
(8) CDR3 - RGSYPYNYFDV

FIG. 7

Translation of 2D12.5 VH variable genes

```
                              10         20         30         40         50
                              |....|....|....|....|....|....|....|....|....|....|
(9) 2d12.5 VH native hybridoma   1 VKLQESGPGLVQPSQSLSITCTVSGFSLTDYGVHWVRQSPGKGLEWLGVI  50
(10) 2d12.5 VH native cloned     1 ..................................................  50
(11) 2d12.5 VH N87D_cloned       1 ..................................................  50
(12) 2d12.5 VH N87D_G53C_cloned  1 ..................................................  50
(13) 2d12.5 VH N87D_G54C_cloned  1 ..................................................  50
(14) 2d12.5 VH N87D_G55C_cloned  1 ..................................................  50

60         70         80         90        100
                              |....|....|....|....|....|....|....|....|....|....|
2d12.5 VH native hybridoma   51 WSGGGTAYTAAFISRLNIYKDNSKNQVFFEMNSLQANDTAMYYCARRGSY 100
2d12.5 VH native cloned      51 .................................................. 100
2d12.5 VH N87D_cloned        51 ....................................D............. 100
2d12.5 VH N87D_G53C_cloned   51 ..C.................................D............. 100
2d12.5 VH N87D_G54C_cloned   51 ...C................................D............. 100
2d12.5 VH N87D_G55C_cloned   51 ....C...............................D............. 100

110
                              |....|....|....|
2d12.5 VH native hybridoma  101 PYNYFDVWGQGTTVTVSS 118
2d12.5 VH native cloned     101 ................A  118
2d12.5 VH N87D_cloned       101 ................A  118
2d12.5 VH N87D_G53C_cloned  101 ................A  118
2d12.5 VH N87D_G54C_cloned  101 ................A  118
2d12.5 VH N87D_G55C_cloned  101 ................A  118
```

FIG. 8

2D12.5 VH variable genes

```
                                         10        20        30        40        50
                                ....|....|....|....|....|....|....|....|....|....|
(15) 2d12.5 VH native hybridoma   1 GTGAAGCTGCAGGAGTCAGGACCTGGCCTAGTGCAGCCCTCACAGAGCCT  50
(16) 2d12.5 VH native cloned      1 ..............................T...................  50
(17) 2d12.5 VH N87D_cloned        1 ..............................T...................  50
(18) 2d12.5 VH N87D_G53C_cloned   1 ..............................T...................  50
(19) 2d12.5 VH N87D_G54C_cloned   1 ..............................T..G.................  50
(20) 2d12.5 VH N87D_G55C_cloned   1 ..............................T...................  50

60        70        80        90       100
                                ....|....|....|....|....|....|....|....|....|....|
     2d12.5 VH native hybridoma  51 GTCCATCACCTGCACGGTCTCTGGTTTCTCATTAACTGACTATGGTGTAC 100
     2d12.5 VH native cloned     51 .................................................. 100
     2d12.5 VH N87D_cloned       51 .................................................. 100
     2d12.5 VH N87D_G53C_cloned  51 .................................................. 100
     2d12.5 VH N87D_G54C_cloned  51 .................................................. 100
     2d12.5 VH N87D_G55C_cloned  51 .................................................. 100

110       120       130       140       150
                                ....|....|....|....|....|....|....|....|....|....|
     2d12.5 VH native hybridoma 101 ACTGGGTTCGCCAGTCTCCAGGAAAGGGTCTGGAATGGCTGGGAGTGATA 150
     2d12.5 VH native cloned    101 .................................................. 150
     2d12.5 VH N87D_cloned      101 .................................................. 150
     2d12.5 VH N87D_G53C_cloned 101 .................................................. 150
     2d12.5 VH N87D_G54C_cloned 101 .................................................. 150
     2d12.5 VH N87D_G55C_cloned 101 .................................................. 150
```

FIG. 9

```
                     160         170        180        190        200
                      |   .   .   |   .   .   |   .   .   |   .   .   |
2d12.5 VH native hybridoma  151 TGGAGTGGTGGAGGCACGGCCTATACTGCGGGCGTTCATATCCAGACTGAA 200
2d12.5 VH native cloned     151 .................................................. 200
2d12.5 VH N87D_cloned       151 ........T......................................... 200
2d12.5 VH N87D_G53C_cloned  151 ........T......................................... 200
2d12.5 VH N87D_G54C_cloned  151 ........T...T.T.................................... 200
2d12.5 VH N87D_G55C_cloned  151 ........T.....T.................................... 200

210        220        230        240        250
                      |   .   .   |   .   .   |   .   .   |   .   .   |
2d12.5 VH native hybridoma  201 CATCTACAAGGACACAATTCCAAGAACCAAGTTTTCTTTGAAATGAACAGTC 250
2d12.5 VH native cloned     201 .................................................. 250
2d12.5 VH N87D_cloned       201 .................................................. 250
2d12.5 VH N87D_G53C_cloned  201 .................................................. 250
2d12.5 VH N87D_G54C_cloned  201 .................................................. 250
2d12.5 VH N87D_G55C_cloned  201 .................................................. 250

260        270        280        290        300
                      |   .   .   |   .   .   |   .   .   |   .   .   |
2d12.5 VH native hybridoma  251 TGCAAGCTAATGACACAGCCCATGTATTACTGTGCCAGAGAAGGGGTAGCTAC 300
2d12.5 VH native cloned     251 .................................................. 300
2d12.5 VH N87D_cloned       251 ..........G....................................... 300
2d12.5 VH N87D_G53C_cloned  251 ..........G....................................... 300
2d12.5 VH N87D_G54C_cloned  251 ..........G....................................... 300
2d12.5 VH N87D_G55C_cloned  251 ..........G....................................... 300
```

FIG. 9 Cont.

Translation of 2D12.5 VL genes

```
                                  10        20        30        40        50
                           ....|....|....|....|....|....|....|....|....|....|
(21) 2d12.5 VL native hybridoma  1 AVVTQESALTTSPGETVTLTCRSSTGAVTTSNYANWVQEKPDHLFTGLIG 50
(22) 2d12.5 VL_native cloned     1 ................................................. 50
(23) 2d12.5 VL_N53C_cloned       1 ................................................. 50

60        70        80        90       100
                           ....|....|....|....|....|....|....|....|....|....|
2d12.5 VL native hybridoma  51 GNNNRPPGVPARFSGSLIGDKAALTIAGTQTEDEAIYFCALWYSNHWVFG 100
2d12.5 VL_native cloned     51 ................................................. 100
2d12.5 VL_N53C_cloned       51 ..C.............................................. 100

2d12.5 VL native hybridoma 101 GGTRLTVLG 109
2d12.5 VL_native cloned    101 ...K...S  109
2d12.5 VL_N53C_cloned      101 ...K...S  109
```

FIG. 10

2D12.5 VL variable genes

```
                              10        20        30        40        50
                              ....|....|....|....|....|....|....|....|....|....|
(24) 2d12.5 VL native hybridoma  1 GCTGTTGTGACTCAGGAATCTGCACTCACCACCATCACCTGGTGAAACAGT  50
(25) 2d12.5 VL_native_cloned      1 ..................................................  50
(26) 2d12.5 VL_N53C_cloned        1 ..................................................  50

60        70        80        90       100
                              ....|....|....|....|....|....|....|....|....|....|
2d12.5 VL native hybridoma   51 CACACTCACTTGTCGCTCAAGTACTGGGGCTGTGTTACGACTAGTAACTATG 100
2d12.5 VL_native_cloned      51 .................................................. 100
2d12.5 VL_N53C_cloned        51 .................................................. 100

110       120       130       140       150
                              ....|....|....|....|....|....|....|....|....|....|
2d12.5 VL native hybridoma  101 CCAACTGGGGTCCAAGAGAAACCAGATCATTTATTCACTGGTCTAATAGGT 150
2d12.5 VL_native_cloned     101 .................................................. 150
2d12.5 VL_N53C_cloned       101 .................................................. 150

160       170       180       190       200
                              ....|....|....|....|....|....|....|....|....|....|
2d12.5 VL native hybridoma  151 GGTAATAATAACCGACCTTCCAGGTGTTCCTGCCAGATTCTCAGGCTCCCT 200
2d12.5 VL_native_cloned     151 .................................................. 200
2d12.5 VL_N53C_cloned       151 ...TG............................................. 200
```

FIG. 11

```
                             210        220        230        240        250
                             ....|....|....|....|....|....|....|....|....|....|
2d12.5 VL native hybridoma  201 GATTGGAGACAAGGCTGCCCTCACCATCGCAGGACACAGACTGAGGATG 250
2d12.5 VL_native_cloned     201 ................................................ 250
2d12.5 VL_N53C_cloned       201 ................................................ 250

260        270        280        290        300
                             ....|....|....|....|....|....|....|....|....|....|
2d12.5 VL native hybridoma  251 AGGCAATATATTCTGTGCTCTATGGTACAGCAACCATTGGGTGTTCGGT 300
2d12.5 VL_native_cloned     251 ................................................ 300
2d12.5 VL_N53C_cloned       251 ................................................ 300

310        320
                             ....|....|....|....|.......
2d12.5 VL native hybridoma  301 GGAGGAACCAGACTGACTGTCCTAGGC 327
2d12.5 VL_native_cloned     301 ..G.........A...........A.. 327
2d12.5 VL_N53C_cloned       301 ..G.........A...........A.. 327
```

FIG. 11 cont.

FIG. 18
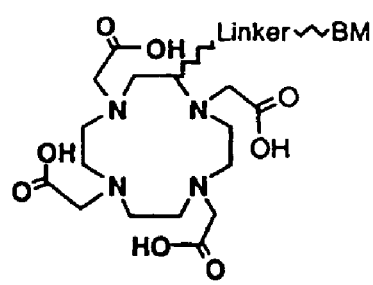 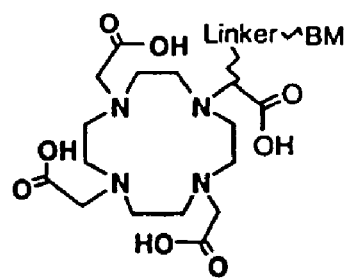 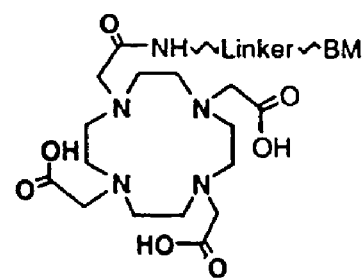
On the macrocyclic
chelator backbone
via a C-C bond
On the acetate
chelating arm
via a C-C bond
On the acetate
chelating arm via
a C-N amide bond FIG. 19
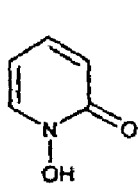
1-Hydroxy-2-pyridinones
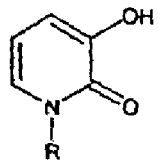
3-Hydroxy-2-pyridinones
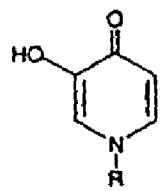
3-Hydroxy-4-pyridinones
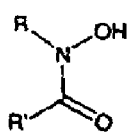
Hydroxymates
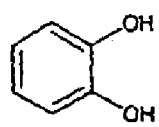
Catechol
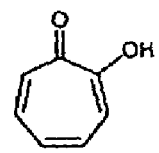
Tropolone
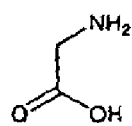
amino acid
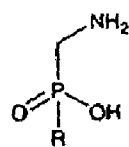
aminophosphi(o)nic acid
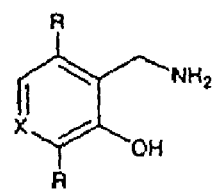
aminephenol
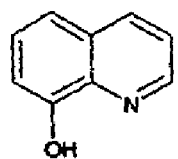
Quinoline
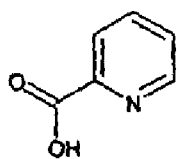
2-pyridine-carboxylic acid
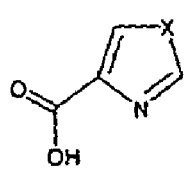
Imidazole-carboxylic acid
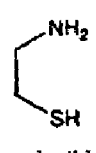
aminethiol
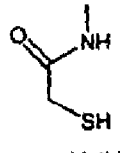
amidethiol
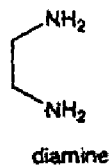
diamine Figure 20   (((S)-2-(4-(2-aminooxy)-acetamido)-benzyl)-1,4,7,10-tetraazacyclododecane-N, N', N'', N'''-tetraacetic acid, AOD.

Figure 22

Table 1A.   Oxidized peptides identified on rHSA.

| M+H | Sequence | modified AA | sequence number |
|---|---|---|---|
| 1508 | (K)AAC*LLP*K | proline | 175-181 |
| 2237 | (K)LDELRDEGK*ASSAK | lysine | 182-195 |
| 1531 | (K)FGER*AFK | arginine | 206-212 |
| 1679 | (K)TPVSDR*VTK | arginine | 467-475 |

Table 1B.   Oxidized peptides identified on FeEDTA/ascorbate-oxidized rHSA.

| M+H | Sequence | modified AA | sequence number | present in control? |
|---|---|---|---|---|
| 1945 | (R)FK*DLGEENFK | lysine | 11-20 | |
| 1665 | (K)ASSAKQR*LK | arginine | 191-199 | |
| 1531 | (K)FGER*AFK | arginine | 206-212 | Y |
| 1971 | (R)FPK*AEFAEVSK | lysine | 223-233 | |
| 1916 | (K)DVC*K*NYAEAK | lysine | 314-323 | |
| 2015 | (R)LAK*TYETTLEK | lysine | 349-359 | |
| 1410 | (K)TP*VSDR | proline | 467-472 | |
| 1679 | (K)TPVSDR*VTK | arginine | 467-475 | Y |

Figure 25

Table 1A.     Oxidized peptides identified on rHSA.

| M+H | Sequence | modified AA | sequence number |
|---|---|---|---|
| 1508 | (K)AAC*LLP*K | proline | 175-181 |
| 2237 | (K)LDELRDEGK*ASSAK | lysine | 182-195 |
| 1531 | (K)FGER*AFK | arginine | 206-212 |
| 1679 | (K)TPVSDR*VTK | arginine | 467-475 |

Table 1B.     Oxidized peptides identified on FeEDTA/ascorbate-oxidized rHSA.

| M+H | Sequence | modified AA | sequence number | present in control? |
|---|---|---|---|---|
| 1945 | (R)FK*DLGEENFK | lysine | 11-20 | |
| 1665 | (K)ASSAKQR*LK | arginine | 191-199 | |
| 1531 | (K)FGER*AFK | arginine | 206-212 | Y |
| 1971 | (R)FPK*AEFAEVSK | lysine | 223-233 | |
| 1916 | (K)DVC*K*NYAEAK | lysine | 314-323 | |
| 2015 | (R)LAK*TYETTLEK | lysine | 349-359 | |
| 1410 | (K)TP*VSDR | proline | 467-472 | |
| 1679 | (K)TPVSDR*VTK | arginine | 467-475 | Y |

SEQUENCE LISTING

<160> NUMBER OF SEQ ID NOS: 58

<210> SEQ ID NO 1
<211> LENGTH: 110
<212> TYPE: PRT
<213> ORGANISM: Mus sp.
<220> FEATURE:
<223> OTHER INFORMATION: mouse monoclonal antibody 2D12.5 light chain
      variable domain (V-L)

<400> SEQUENCE: 1

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Asn Asn Asn Arg Pro Pro Gly Val Pro Ala Arg Phe
        50                  55                  60

Ser Gly Ser Leu Ile Gly Asp Lys Ala Ala Leu Thr Ile Ala Gly Thr
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Arg Leu Thr Val Leu Gly
            100                 105                 110

<210> SEQ ID NO 2
<211> LENGTH: 14
<212> TYPE: PRT
<213> ORGANISM: Mus sp.
<220> FEATURE:
<223> OTHER INFORMATION: mouse monoclonal antibody 2D12.5 light chain
      variable domain (V-L) complementarity determining
      region 1 (CDR1)

<400> SEQUENCE: 2

Arg Ser Ser Thr Gly Ala Val Thr Thr Ser Asn Tyr Ala Asn
 1               5                  10

<210> SEQ ID NO 3
<211> LENGTH: 7
<212> TYPE: PRT
<213> ORGANISM: Mus sp.
<220> FEATURE:
<223> OTHER INFORMATION: mouse monoclonal antibody 2D12.5 light chain
      variable domain (V-L) complementarity determining
      region 2 (CDR2)

<400> SEQUENCE: 3

Gly Asn Asn Asn Arg Pro Pro
 1               5

<210> SEQ ID NO 4
<211> LENGTH: 9
<212> TYPE: PRT
<213> ORGANISM: Mus sp.
<220> FEATURE:
<223> OTHER INFORMATION: mouse monoclonal antibody 2D12.5 light chain
      variable domain (V-L) complementarity determining
      region 3 (CDR3)

<400> SEQUENCE: 4

Ala Leu Trp Tyr Ser Asn His Trp Val

<210> SEQ ID NO 5
<211> LENGTH: 117
<212> TYPE: PRT
<213> ORGANISM: Mus sp.
<220> FEATURE:
<223> OTHER INFORMATION: mouse monoclonal antibody 2D12.5 heavy chain
      variable domain (V-H)

<400> SEQUENCE: 5

```
Gln Val Lys Leu Gln Glu Ser Pro Gly Leu Gln Pro Ser Gln Ser Leu
  1               5                  10                  15

Ser Ile Thr Cys Thr Val Ser Gly Phe Ser Leu Thr Asp Tyr Gly Val
             20                  25                  30

His Trp Val Arg Gln Ser Pro Gly Lys Gly Leu Glu Trp Leu Gly Val
         35                  40                  45

Ile Trp Ser Gly Gly Gly Thr Ala Tyr Thr Ala Ala Phe Ile Ser Arg
 50                  55                  60

Leu Asn Ile Tyr Lys Asp Asn Ser Lys Asn Gln Val Phe Phe Glu Met
 65                  70                  75                  80

Asn Ser Leu Gln Ala Asn Asp Thr Ala Met Tyr Tyr Cys Ala Arg Arg
                 85                  90                  95

Gly Ser Tyr Pro Tyr Asn Tyr Phe Asp Val Trp Gly Gln Gly Thr Thr
            100                 105                 110

Val Thr Val Ser Ser
        115
```

<210> SEQ ID NO 6
<211> LENGTH: 5
<212> TYPE: PRT
<213> ORGANISM: Mus sp.
<220> FEATURE:
<223> OTHER INFORMATION: mouse monoclonal antibody 2D12.5 heavy chain
      variable domain (V-H) complementarity determining
      region 1 (CDR1)

<400> SEQUENCE: 6

```
Asp Tyr Gly Val His
  1               5
```

<210> SEQ ID NO 7
<211> LENGTH: 16
<212> TYPE: PRT
<213> ORGANISM: Mus sp.
<220> FEATURE:
<223> OTHER INFORMATION: mouse monoclonal antibody 2D12.5 heavy chain
      variable domain (V-H) complementarity determining
      region 2 (CDR2)

<400> SEQUENCE: 7

```
Val Ile Trp Ser Gly Gly Gly Thr Ala Tyr Thr Ala Ala Phe Ile Ser
  1               5                  10                  15
```

<210> SEQ ID NO 8
<211> LENGTH: 11
<212> TYPE: PRT
<213> ORGANISM: Mus sp.
<220> FEATURE:
<223> OTHER INFORMATION: mouse monoclonal antibody 2D12.5 heavy chain
      variable domain (V-H) complementarity determining
      region 3 (CDR3)

<400> SEQUENCE: 8

Arg Gly Ser Tyr Pro Tyr Asn Tyr Phe Asp Val
1               5                   10

<210> SEQ ID NO 9
<211> LENGTH: 116
<212> TYPE: PRT
<213> ORGANISM: Mus sp.
<220> FEATURE:
<223> OTHER INFORMATION: mouse monoclonal antibody 2D12.5 heavy chain
      variable domain (V-H) native hybridoma sequence

<400> SEQUENCE: 9

Val Lys Leu Gln Glu Ser Pro Gly Leu Gln Pro Ser Gln Ser Leu Ser
1               5                   10                  15

Ile Thr Cys Thr Val Ser Gly Phe Ser Leu Thr Asp Tyr Gly Val His
                20                  25                  30

Trp Val Arg Gln Ser Pro Gly Lys Gly Leu Glu Trp Leu Gly Val Ile
            35                  40                  45

Trp Ser Gly Gly Gly Thr Ala Tyr Thr Ala Ala Phe Ile Ser Arg Leu
50                  55                  60

Asn Ile Tyr Lys Asp Asn Ser Lys Asn Gln Val Phe Phe Glu Met Asn
65                  70                  75                  80

Ser Leu Gln Ala Asn Asp Thr Ala Met Tyr Tyr Cys Ala Arg Arg Gly
                85                  90                  95

Ser Tyr Pro Tyr Asn Tyr Phe Asp Val Trp Gly Gln Gly Thr Thr Val
            100                 105                 110

Thr Val Ser Ser
        115

<210> SEQ ID NO 10
<211> LENGTH: 116
<212> TYPE: PRT
<213> ORGANISM: Mus sp.
<220> FEATURE:
<223> OTHER INFORMATION: mouse monoclonal antibody 2D12.5 heavy chain
      variable domain (V-H) native cloned hybridoma
      sequence

<400> SEQUENCE: 10

Val Lys Leu Gln Glu Ser Pro Gly Leu Gln Pro Ser Gln Ser Leu Ser
1               5                   10                  15

Ile Thr Cys Thr Val Ser Gly Phe Ser Leu Thr Asp Tyr Gly Val His
                20                  25                  30

Trp Val Arg Gln Ser Pro Gly Lys Gly Leu Glu Trp Leu Gly Val Ile
            35                  40                  45

Trp Ser Gly Gly Gly Thr Ala Tyr Thr Ala Ala Phe Ile Ser Arg Leu
50                  55                  60

Asn Ile Tyr Lys Asp Asn Ser Lys Asn Gln Val Phe Phe Glu Met Asn
65                  70                  75                  80

Ser Leu Gln Ala Asn Asp Thr Ala Met Tyr Tyr Cys Ala Arg Arg Gly
                85                  90                  95

Ser Tyr Pro Tyr Asn Tyr Phe Asp Val Trp Gly Gln Gly Thr Thr Val
            100                 105                 110

Thr Val Ser Ala
        115

<210> SEQ ID NO 11
<211> LENGTH: 116
<212> TYPE: PRT
<213> ORGANISM: Artificial Sequence

```
<220> FEATURE:
<223> OTHER INFORMATION: Description of Artificial Sequence:mouse
      monoclonal antibody 2D12.5 heavy chain variable
      domain (V-H) N87D cloned sequence

<400> SEQUENCE: 11

Val Lys Leu Gln Glu Ser Pro Gly Leu Gln Pro Ser Gln Ser Leu Ser
  1               5                  10                  15

Ile Thr Cys Thr Val Ser Gly Phe Ser Leu Thr Asp Tyr Gly Val His
             20                  25                  30

Trp Val Arg Gln Ser Pro Gly Lys Gly Leu Glu Trp Leu Gly Val Ile
         35                  40                  45

Trp Ser Gly Gly Thr Ala Tyr Thr Ala Ala Phe Ile Ser Arg Leu
     50                  55                  60

Asn Ile Tyr Lys Asp Asn Ser Lys Asn Gln Val Phe Phe Glu Met Asn
 65                  70                  75                  80

Ser Leu Gln Ala Asp Asp Thr Ala Met Tyr Tyr Cys Ala Arg Arg Gly
             85                  90                  95

Ser Tyr Pro Tyr Asn Tyr Phe Asp Val Trp Gly Gln Gly Thr Thr Val
            100                 105                 110

Thr Val Ser Ala
        115

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence:mouse
      monoclonal antibody 2D12.5 heavy chain variable
      domain (V-H) N87D_G53C cloned sequence

<400> SEQUENCE: 12

Val Lys Leu Gln Glu Ser Pro Gly Leu Gln Pro Ser Gln Ser Leu Ser
  1               5                  10                  15

Ile Thr Cys Thr Val Ser Gly Phe Ser Leu Thr Asp Tyr Gly Val His
             20                  25                  30

Trp Val Arg Gln Ser Pro Gly Lys Gly Leu Glu Trp Leu Gly Val Ile
         35                  40                  45

Trp Ser Cys Gly Gly Thr Ala Tyr Thr Ala Ala Phe Ile Ser Arg Leu
     50                  55                  60

Asn Ile Tyr Lys Asp Asn Ser Lys Asn Gln Val Phe Phe Glu Met Asn
 65                  70                  75                  80

Ser Leu Gln Ala Asp Asp Thr Ala Met Tyr Tyr Cys Ala Arg Arg Gly
             85                  90                  95

Ser Tyr Pro Tyr Asn Tyr Phe Asp Val Trp Gly Gln Gly Thr Thr Val
            100                 105                 110

Thr Val Ser Ala
        115

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence:mouse
      monoclonal antibody 2D12.5 heavy chain variable
      domain (V-H) N87D_G54C cloned sequence

<400> SEQUENCE: 13
```

```
Val Lys Leu Gln Glu Ser Pro Gly Leu Gln Pro Ser Gln Ser Leu Ser
 1               5                  10                  15

Ile Thr Cys Thr Val Ser Gly Phe Ser Leu Thr Asp Tyr Gly Val His
             20                  25                  30

Trp Val Arg Gln Ser Pro Gly Lys Gly Leu Glu Trp Leu Gly Val Ile
         35                  40                  45

Trp Ser Gly Cys Gly Thr Ala Tyr Thr Ala Ala Phe Ile Ser Arg Leu
     50                  55                  60

Asn Ile Tyr Lys Asp Asn Ser Lys Asn Gln Val Phe Phe Glu Met Asn
 65                  70                  75                  80

Ser Leu Gln Ala Asp Asp Thr Ala Met Tyr Tyr Cys Ala Arg Arg Gly
                 85                  90                  95

Ser Tyr Pro Tyr Asn Tyr Phe Asp Val Trp Gly Gln Gly Thr Thr Val
             100                 105                 110

Thr Val Ser Ala
        115
```

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence:mouse
      monoclonal antibody 2D12.5 heavy chain variable
      domain (V-H) N87D_G55C cloned sequence

<400> SEQUENCE: 14

```
Val Lys Leu Gln Glu Ser Pro Gly Leu Gln Pro Ser Gln Ser Leu Ser
 1               5                  10                  15

Ile Thr Cys Thr Val Ser Gly Phe Ser Leu Thr Asp Tyr Gly Val His
             20                  25                  30

Trp Val Arg Gln Ser Pro Gly Lys Gly Leu Glu Trp Leu Gly Val Ile
         35                  40                  45

Trp Ser Gly Gly Cys Thr Ala Tyr Thr Ala Ala Phe Ile Ser Arg Leu
     50                  55                  60

Asn Ile Tyr Lys Asp Asn Ser Lys Asn Gln Val Phe Phe Glu Met Asn
 65                  70                  75                  80

Ser Leu Gln Ala Asp Asp Thr Ala Met Tyr Tyr Cys Ala Arg Arg Gly
                 85                  90                  95

Ser Tyr Pro Tyr Asn Tyr Phe Asp Val Trp Gly Gln Gly Thr Thr Val
             100                 105                 110

Thr Val Ser Ala
        115
```

<210> SEQ ID NO 15
<211> LENGTH: 354
<212> TYPE: DNA
<213> ORGANISM: Mus sp.
<220> FEATURE:
<223> OTHER INFORMATION: mouse monoclonal antibody 2D12.5 heavy chain
      variable domain (V-H) native hybridoma sequence

<400> SEQUENCE: 15

```
gtgaagctgc aggagtcagg acctggccta gtgcagccct cacagagcct gtccatcacc     60
tgcacggtct ctggtttctc attaactgac tatggtgtac actgggttcg ccagtctcca    120
ggaaagggtc tggaatggct gggagtgata tggagtggtg gaggcacggc ctatactgcg    180
gcgttcatat ccagactgaa catctacaag gacaattcca agaaccaagt tttctttgaa    240
```

```
atgaacagtc tgcaagctaa tgacacagcc atgtattact gtgccagaag gggtagctac    300
ccttacaact acttcgatgt ctggggccaa gggaccacag tcaccgtctc ctca           354
```

<210> SEQ ID NO 16
<211> LENGTH: 354
<212> TYPE: DNA
<213> ORGANISM: Mus sp.
<220> FEATURE:
<223> OTHER INFORMATION: mouse monoclonal antibody 2D12.5 heavy chain
      variable domain (V-H) native cloned hybridoma
      sequence

<400> SEQUENCE: 16

```
gtgaagctgc aggagtctgg acctggccta gtgcagccct cacagagcct gtccatcacc    60
tgcacggtct ctggtttctc attaactgac tatggtgtac actgggttcg ccagtctcca   120
ggaaagggtc tggaatggct gggagtgata tggagtggtg gaggcacggc ctatactgcg   180
gcgttcatat ccagactgaa catctacaag gacaattcca agaaccaagt tttctttgaa   240
atgaacagtc tgcaagctaa tgacacagcc atgtattact gtgccagaag gggtagctac   300
ccttacaact acttcgatgt ctggggccaa gggaccacgg tcaccgtctc cgca          354
```

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence:mouse
      monoclonal antibody 2D12.5 heavy chain variable
      domain (V-H) N87D cloned sequence

<400> SEQUENCE: 17

```
gtgaagctgc aggagtctgg acctggccta gtgcagccct cacagagcct gtccatcacc    60
tgcacggtct ctggtttctc attaactgac tatggtgtac actgggttcg ccagtctcca   120
ggaaagggtc tggaatggct gggagtgata tggagtggtg gaggcacggc ctatactgcg   180
gcgttcatat ccagactgaa catctacaag gacaattcca agaaccaagt tttctttgaa   240
atgaacagtc tgcaagctga tgacacagcc atgtattact gtgccagaag gggtagctac   300
ccttacaact acttcgatgt ctggggccaa gggaccacgg tcaccgtctc cgca          354
```

<210> SEQ ID NO 18
<211> LENGTH: 354
<212> TYPE: DNA
<213> ORGANISM: Artificial Sequence
<220> FEATURE:
<223> OTHER INFORMATION: Description of Artificial Sequence:mouse
      monoclonal antibody 2D12.5 heavy chain variable
      domain (V-H) N87D_G53C cloned sequence

<400> SEQUENCE: 18

```
gtgaagctgc aggagtctgg acctggccta gtgcagccct cacagagcct gtccatcacc    60
tgcacggtct ctggtttctc attaactgac tatggtgtac actgggttcg ccagtctcca   120
ggaaagggtc tggaatggct gggagtgata tggagttgtg gaggcacggc ctatactgcg   180
gcgttcatat ccagactgaa catctacaag gacaattcca agaaccaagt tttctttgaa   240
atgaacagtc tgcaagctga tgacacagcc atgtattact gtgccagaag gggtagctac   300
ccttacaact acttcgatgt ctggggccaa gggaccacgg tcaccgtctc cgca          354
```

<210> SEQ ID NO 19
<211> LENGTH: 354

<212> TYPE: DNA
<213> ORGANISM: Artificial Sequence
<220> FEATURE:
<223> OTHER INFORMATION: Description of Artificial Sequence:mouse
monoclonal antibody 2D12.5 heavy chain variable
domain (V-H) N87D_G54C cloned sequence

<400> SEQUENCE: 19

```
gtgaagctgc aggagtctgg gcctggccta gtgcagccct cacagagcct gtccatcacc    60
tgcacggtct ctggtttctc attaactgac tatggtgtac actgggttcg ccagtctcca   120
ggaaagggtc tggaatggct gggagtgata tggagtggtt gtggcacggc ctatactgcg   180
gcgttcatat ccagactgaa catctacaag gacaattcca agaaccaagt tttctttgaa   240
atgaacagtc tgcaagctga tgacacagcc atgtattact gtgccagaag gggtagctac   300
ccttacaact acttcgatgt ctggggccaa gggaccacgg tcaccgtctc cgca          354
```

<210> SEQ ID NO 20
<211> LENGTH: 354
<212> TYPE: DNA
<213> ORGANISM: Artificial Sequence
<220> FEATURE:
<223> OTHER INFORMATION: Description of Artificial Sequence:mouse
monoclonal antibody 2D12.5 heavy chain variable
domain (V-H) N87D_G55C cloned sequence

<400> SEQUENCE: 20

```
gtgaagctgc aggagtctgg acctggccta gtgcagccct cacagagcct gtccatcacc    60
tgcacggtct ctggtttctc attaactgac tatggtgtac actgggttcg ccagtctcca   120
ggaaagggtc tggaatggct gggagtgata tggagtggtg gatgcacggc ctatactgcg   180
gcgttcatat ccagactgaa catctacaag gacaattcca agaaccaagt tttctttgaa   240
atgaacagtc tgcaagctga tgacacagcc atgtattact gtgccagaag gggtagctac   300
ccttacaact acttcgatgt ctggggccaa gggaccacgg tcaccgtctc cgca          354
```

<210> SEQ ID NO 21
<211> LENGTH: 109
<212> TYPE: PRT
<213> ORGANISM: Mus sp.
<220> FEATURE:
<223> OTHER INFORMATION: mouse monoclonal antibody 2D12.5 light chain
variable domain (V-L) native hybridoma sequence

<400> SEQUENCE: 21

```
Ala Val Val Thr Gln Glu Ser Ala Leu Thr Thr Ser Pro Gly Glu Thr
  1               5                  10                  15

Val Thr Leu Thr Cys Arg Ser Ser Thr Gly Ala Val Thr Thr Ser Asn
             20                  25                  30

Tyr Ala Asn Trp Val Gln Glu Lys Pro Asp His Leu Phe Thr Gly Leu
         35                  40                  45

Ile Gly Gly Asn Asn Asn Arg Pro Pro Gly Val Pro Ala Arg Phe Ser
     50                  55                  60

Gly Ser Leu Ile Gly Asp Lys Ala Ala Leu Thr Ile Ala Gly Thr Gln
 65                  70                  75                  80

Thr Glu Asp Glu Ala Ile Tyr Phe Cys Ala Leu Trp Tyr Ser Asn His
                 85                  90                  95

Trp Val Phe Gly Gly Gly Thr Arg Leu Thr Val Leu Gly
            100                 105
```

<210> SEQ ID NO 22

```
<211> LENGTH: 109
<212> TYPE: PRT
<213> ORGANISM: Mus sp.
<220> FEATURE:
<223> OTHER INFORMATION: mouse monoclonal antibody 2D12.5 light chain
      variable domain (V-L) native cloned hybridoma
      sequence

<400> SEQUENCE: 22

Ala Val Val Thr Gln Glu Ser Ala Leu Thr Thr Ser Pro Gly Glu Thr
 1               5                  10                  15

Val Thr Leu Thr Cys Arg Ser Ser Thr Gly Ala Val Thr Thr Ser Asn
                20                  25                  30

Tyr Ala Asn Trp Val Gln Glu Lys Pro Asp His Leu Phe Thr Gly Leu
            35                  40                  45

Ile Gly Gly Asn Asn Asn Arg Pro Pro Gly Val Pro Ala Arg Phe Ser
    50                  55                  60

Gly Ser Leu Ile Gly Asp Lys Ala Ala Leu Thr Ile Ala Gly Thr Gln
65                  70                  75                  80

Thr Glu Asp Glu Ala Ile Tyr Phe Cys Ala Leu Trp Tyr Ser Asn His
                85                  90                  95

Trp Val Phe Gly Gly Gly Thr Lys Leu Thr Val Leu Ser
                100                 105

<210> SEQ ID NO 23
<211> LENGTH: 109
<212> TYPE: PRT
<213> ORGANISM: Artificial Sequence
<220> FEATURE:
<223> OTHER INFORMATION: Description of Artificial Sequence:mouse
      monoclonal antibody 2D12.5 light chain variable
      domain (V-L) N53C cloned sequence

<400> SEQUENCE: 23

Ala Val Val Thr Gln Glu Ser Ala Leu Thr Thr Ser Pro Gly Glu Thr
 1               5                  10                  15

Val Thr Leu Thr Cys Arg Ser Ser Thr Gly Ala Val Thr Thr Ser Asn
                20                  25                  30

Tyr Ala Asn Trp Val Gln Glu Lys Pro Asp His Leu Phe Thr Gly Leu
            35                  40                  45

Ile Gly Gly Cys Asn Asn Arg Pro Pro Gly Val Pro Ala Arg Phe Ser
    50                  55                  60

Gly Ser Leu Ile Gly Asp Lys Ala Ala Leu Thr Ile Ala Gly Thr Gln
65                  70                  75                  80

Thr Glu Asp Glu Ala Ile Tyr Phe Cys Ala Leu Trp Tyr Ser Asn His
                85                  90                  95

Trp Val Phe Gly Gly Gly Thr Lys Leu Thr Val Leu Ser
                100                 105

<210> SEQ ID NO 24
<211> LENGTH: 327
<212> TYPE: DNA
<213> ORGANISM: Mus sp.
<220> FEATURE:
<223> OTHER INFORMATION: mouse monoclonal antibody 2D12.5 light chain
      variable domain (V-L) native hybridoma sequence

<400> SEQUENCE: 24
gctgttgtga ctcaggaatc tgcactcacc acatcacctg gtgaaacagt cacactcact       60
tgtcgctcaa gtactggggc tgttacgact agtaactatg ccaactgggt ccaagagaaa     120
```

```
ccagatcatt tattcactgg tctaataggt ggtaataata accgacctcc aggtgttcct      180
gccagattct caggctccct gattggagac aaggctgccc tcaccatcgc agggacacag      240
actgaggatg aggcaatata tttctgtgct ctatggtaca gcaaccattg ggtgttcggt      300
ggaggaacca gactgactgt cctaggc                                         327

<210> SEQ ID NO 25
<211> LENGTH: 327
<212> TYPE: DNA
<213> ORGANISM: Mus sp.
<220> FEATURE:
<223> OTHER INFORMATION: mouse monoclonal antibody 2D12.5 light chain
      variable domain (V-L) native cloned hybridoma
      sequence

<400> SEQUENCE: 25
gctgttgtga ctcaggaatc tgcactcacc acatcacctg gtgaaacagt cacactcact      60
tgtcgctcaa gtactggggc tgttacgact agtaactatg ccaactgggt ccaagagaaa      120
ccagatcatt tattcactgg tctaataggt ggtaataata accgacctcc aggtgttcct      180
gccagattct caggctccct gattggagac aaggctgccc tcaccatcgc agggacacag      240
actgaggatg aggcaatata tttctgtgct ctatggtaca gcaaccattg ggtgttcggt      300
gggggaacca aactgactgt cctaagc                                         327

<210> SEQ ID NO 26
<211> LENGTH: 327
<212> TYPE: DNA
<213> ORGANISM: Artificial Sequence
<220> FEATURE:
<223> OTHER INFORMATION: Description of Artificial Sequence:mouse
      monoclonal antibody 2D12.5 light chain variable
      domain (V-L) N53C cloned sequence

<400> SEQUENCE: 26
gctgttgtga ctcaggaatc tgcactcacc acatcacctg gtgaaacagt cacactcact      60
tgtcgctcaa gtactggggc tgttacgact agtaactatg ccaactgggt ccaagagaaa      120
ccagatcatt tattcactgg tctaataggt ggttgtaata accgacctcc aggtgttcct      180
gccagattct caggctccct gattggagac aaggctgccc tcaccatcgc agggacacag      240
actgaggatg aggcaatata tttctgtgct ctatggtaca gcaaccattg ggtgttcggt      300
gggggaacca aactgactgt cctaagc                                         327

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:exemplary
      binding molecule His-4 peptide

<400> SEQUENCE: 27

His His His His
  1

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:exemplary
      binding molecule His-6 peptide
```

-continued

```
<400> SEQUENCE: 28

His His His His His His
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:exemplary
      binding molecule His-8 peptide

<400> SEQUENCE: 29

His His His His His His His His
  1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:exemplary
      binding molecule His-10 peptide

<400> SEQUENCE: 30

His His His His His His His His His His
  1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:exemplary
      binding molecule His-12 peptide

<400> SEQUENCE: 31

His His His His His His His His His His His His
  1               5                  10

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence:(Gly-4Ser)-3
      flexible linker

<400> SEQUENCE: 32

Gly Gly Gly Gly Ser Gly Gly Gly Gly Ser Gly Gly Gly Gly Ser
  1               5                  10                  15

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:5' PCR
      primer for site-directed substitution N87D of heavy chain
      (MTforward), amplification 3' primer to eliminate
      G48S mutation and introduce N53C mutation

<400> SEQUENCE: 33
catctcagtg caactaaa                                              18

<210> SEQ ID NO 34
<211> LENGTH: 31
```

<212> TYPE: DNA
<213> ORGANISM: Artificial Sequence
<220> FEATURE:
<223> OTHER INFORMATION: Description of Artificial Sequence:3' PCR
      primer for site-directed substitution N87D of heavy chain

<400> SEQUENCE: 34
catggctgtg tcatcagctt gcagactgtt c                           31

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:3' PCR
      primer for site-directed substitution G53C of heavy chain

<400> SEQUENCE: 35
cgtgcctcca caactccata tcac                                   24

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:3' PCR
      primer for site-directed substitution G54C of heavy chain

<400> SEQUENCE: 36
ccgtgccaca accactccat atc                                    23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence:3' PCR
      primer for site-directed substitution G55C of heavy chain

<400> SEQUENCE: 37
ccgtgcatcc accactccat atc                                    23

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence:5' PCR
      primer for site-directed substitution N53C of light chain
      (2dVl5'Bgl)

<400> SEQUENCE: 38
gaagatctgc tgttgtgact caggaatct                              29

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence:3' PCR
      primer for site-directed substitution N53C of light chain

<400> SEQUENCE: 39
agatggtgca gccacagttc ggcttaggac agtcagtttg gt               42

<210> SEQ ID NO 40
<211> LENGTH: 42

```
<212> TYPE: DNA
<213> ORGANISM: Artificial Sequence
<220> FEATURE:
<223> OTHER INFORMATION: Description of Artificial Sequence:5' PCR
      primer for site-directed substitution N53C of light chain

<400> SEQUENCE: 40
accaaactga ctgtcctaag ccgaactgtg gctgcaccat ct                    42

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:3' PCR
      primer for site-directed substitution N53C of light chain
      (TTCL3)

<400> SEQUENCE: 41
cgatctagaa ttaacactct cccctg                                      26

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:PCR 5'
      primer to introduce BglII site

<400> SEQUENCE: 42
gctcgggaga tgtgtgaagc tg                                          22

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:PCR
      amplification 3' primer and PCR 3' primer to
      introduce BglII site (BGH reverse)

<400> SEQUENCE: 43
tagaaggcac agtcgagg                                               18

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence:
      amplification 3' primer to eliminate G48S mutation and introduce
      N53C mutation

<400> SEQUENCE: 44
cggttattac aaccacctat tagaccagtg aataaatg                         38

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence:
      amplification 5' primer to eliminate G48S mutation and introduce
      N53C mutation

<400> SEQUENCE: 45
gctcgggaga tgtgctgttg tg                                          22
```

```
<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (3)
<223> OTHER INFORMATION: Xaa = Cys acetamide
<220> FEATURE:
<221> NAME/KEY: MOD_RES
<222> LOCATION: (6)
<223> OTHER INFORMATION: Xaa = Pro modified by Tb AOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 46

Ala Ala Xaa Leu Leu Xaa Lys
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (4)
<223> OTHER INFORMATION: Xaa = Cys acetamide
<220> FEATURE:
<221> NAME/KEY: MOD_RES
<222> LOCATION: (7)
<223> OTHER INFORMATION: Xaa = Pro modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 47

Lys Ala Ala Xaa Leu Leu Xaa Lys
 1               5

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (10)
<223> OTHER INFORMATION: Xaa = Lys modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 48

Lys Leu Asp Glu Leu Arg Asp Glu Gly Xaa Ala Ser Ser Ala Lys
 1               5                  10                  15

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
```

```
<220> FEATURE:
<221> NAME/KEY: MOD_RES
<222> LOCATION: (5)
<223> OTHER INFORMATION: Xaa = Arg modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 49

Lys Phe Gly Glu Xaa Ala Phe Lys
 1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (7)
<223> OTHER INFORMATION: Xaa = Arg modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 50

Lys Thr Pro Val Ser Asp Xaa Val Thr Lys
 1               5                  10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (3)
<223> OTHER INFORMATION: Xaa = Lys modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 51

Arg Phe Xaa Asp Leu Gly Glu Glu Asn Phe Lys
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (8)
<223> OTHER INFORMATION: Xaa = Arg modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 52

Lys Ala Ser Ser Ala Lys Gln Xaa Leu Lys
 1               5                  10

<210> SEQ ID NO 53
<211> LENGTH: 8
```

```
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (5)
<223> OTHER INFORMATION: Xaa = Arg modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 53

Lys Phe Gly Glu Xaa Ala Phe Lys
 1               5

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (4)
<223> OTHER INFORMATION: Xaa = Lys modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 54

Arg Phe Pro Xaa Ala Glu Phe Ala Glu Val Ser Lys
 1               5                  10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (4)
<223> OTHER INFORMATION: Xaa = Cys acetamide
<220> FEATURE:
<221> NAME/KEY: MOD_RES
<222> LOCATION: (5)
<223> OTHER INFORMATION: Xaa = Lys modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 55

Lys Asp Val Xaa Xaa Asn Tyr Ala Glu Ala Lys
 1               5                  10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (4)
<223> OTHER INFORMATION: Xaa = Lys modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)
```

```
<400> SEQUENCE: 56

Arg Leu Ala Xaa Thr Tyr Glu Thr Thr Leu Glu Lys
  1               5                  10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (3)
<223> OTHER INFORMATION: Xaa = Pro modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 57

Lys Thr Xaa Val Ser Asp Arg
  1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence:recombinant
      human serum albumin (rHSA) tagged tryptic peptide
<220> FEATURE:
<221> NAME/KEY: MOD_RES
<222> LOCATION: (7)
<223> OTHER INFORMATION: Xaa = Arg modified by TbAOD and HoAOD (AOD =
      ((S)-2-(4-(2-aminooxy)-acetamido)-benzyl)-1,4,7,10-
      tetraazacyclododecane-N,N',N'',N'''-tetraacetic
      acid)

<400> SEQUENCE: 58

Lys Thr Pro Val Ser Asp Xaa Val Thr Lys
  1               5                  10
```

ELEMENT-CODED AFFINITY TAGS

CROSS-REFERENCES TO RELATED APPLICATIONS

This application is a continuation-in-part of U.S. patent application Ser. No. 10/835,533, filed Apr. 28, 2004, which claims the benefit of U.S. Provisional Application No. 60/466,529, filed Apr. 28, 2003 and 60/495,449, filed Aug. 15, 2003, the disclosures of which are incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. CA16861, and Grant No. GM25909 awarded by the NIH/NCI to C. F. Meares and GM049077 awarded to C. B. Lebrilla. The Government has certain rights in this invention.

BACKGROUND OF THE INVENTION

Technologies are needed that enable comprehensive biomarker and target discovery for detection, prognosis, patient stratification, and therapeutics. Methods of detecting biomolecules (e.g., polypeptides, nucleic acids, polysaccharides, and lipids) are widely used in a variety of fields including, e.g., proteomics and genomics. Detection, analysis, and identification of biomolecules can play an important role in the understanding of the biology of organisms and the causes of disease. (See, e.g., Pandey et al., *Nature*, 405: 837-846 (2000).

In particular, oxidation of biomolecules including nucleic acids, lipids, and proteins has been implicated in several diseases including, e.g., Alzheimer's disease, acute respiratory distress syndrome, amyotrophic lateral sclerosis, cataractogenesis, chronic lung disease, bronchopulmonary dysplasia, chronic renal failure, chronic uremia, cystic fibrosis, dementia, diabetes, ischemia-reperfusion, Parkinson's diease, preeclampsia, psoriasis, rheumatoid arthritis, juvenile and chronic arthritis, severe sepsis, systemic amyloidosis, and varicocele (see, e.g., Butterfield, *Brain Res.* 1000: 1-7 (2004); Butterfield and Castegna, *Amino Acids* 25:419-425 (2003); Dalle-Donne et al., *Trends Mol. Med.* 9(4):169-176 (2003); Himmelfarb and McMonagle, *Kidney Int'l.* 60:358-363 (2001); and Odetti et al., *Acta Diabetol* 36:179-183 (1999). Often, oxidation patterns of biomolecules change (e.g., increase or decrease) with disease progression or regression. In addition, oxidation patterns (i.e., the identity of specific oxidized sites) changes with disease progression or gresssion. For example, as the severity of neurodegenerative disorders such as Alzheimer's disease increases, the levels of oxidized creatinine Kinase BB, glutamine synthase, ubiquitin carboxy-terminal hydrolase L-1, and dihydropyrimidinease related protein 2 increases (see, e.g., Butterfield and Castegna, *Amino Acids* 25:419-425 (2003)). Conversely, as the severity of a neurodegenerative disease is diminished, e.g., in conjunction with pharmaceutical therapy, the levels of oxidized proteins decreases.

A number of different technologies have been developed to separate, analyze and identify biomolecules such as proteins. For example, efforts to identify oxidized proteins and to map oxidized proteins using monoclonal antibodies, two dimensional gel electrophoresis, HPLC, and mass spectrometry have been described (see, e.g., Butterfield, *Brain Res.* 1000:1-7 (2004); Butterfield and Castegna, *Amino Acids* 25:419-425 (2003); Himmelfarb and McMonagle, *Kidney Int'l.* 60:358-363 (2001); and Odetti et al., *Acta Diabetol* 36:179-183 (1999)). However, many of these methods are inconvenient for simulataneous analysis of multiple samples.

Typically, identification by mass spectrometry (MS) involves analysis of isolated proteins or peptide fragments, followed by mapping or tandem MS to obtain sequence information. One strategy that has been used to differentiate the resulting spectra involves tagging the proteins with reagents having different masses ("mass tags"). The most predominant mass tags are based on the mass difference of the isotopes hydrogen and deuterium. The isotopically distinct mass tags are referred to as Isotope-Coded Affinity Tags (ICAT), and their use allows a number of different samples to be analyzed at the same time and directly compared. See, e.g., Ranish et al. *Nature Genet.* 33: 349-355 (2003); Zhou et al., *Nature Biotechnol.* 19: 512-515 (2002); Gygi et al., *J. Proteome Res.* 1: 47-54 (2002); Gygi et al., *Nature Biotechnol.* 17: 994-998 (1999); Gygi and Aebersold, *Curr. Opin. Chem. Biol.* 4: 489-494 (2000); Aebersold and Mann, *Nature* 422: 198-207 (2003); Patterson and Aebersold, *Nature Genetics Suppl.* 33: 311-323 (2003); and Tao and Aebersold, *Curr. Opin. Biotechnol.* 14: 110-118 (2003); and WO 00/11208. The reagent consists of biotin for affinity selection, a linker that contains light (hydrogen) or heavy (deuterium) isotopes of hydrogen for mass tagging, and a Cys-reactive group (iodoacetamide) to derivatize proteins. Differential labeling involves using two isotopic reagents for two samples in comparative profiling. Samples are mixed following the ICAT derivatization step and proteolyzed together. The tagged peptides are affinity purified using an avidin column, and analyzed by mass spectrometry. The ratio of mass peak amplitude of peptides from proteins differentially labeled with heavy and light mass tags gives a measure of the relative amounts of each protein. The ICAT method, using a heavy reagent and a light reagent, is limited to differential analysis of two samples.

ICAT has a number of shortcomings. First, ICAT utilizes only two different masses (light and heavy). Thus, the method is limited to applications that require comparisons of only two states. Second, cysteine (Cys) is an amino acid of low abundance (about 2.2%). Moreover, many cells contain endogenously biotinylated proteins, the proteolyzed fragments of which are immobilized by the affinity column. Of particular note is the tendency of the deuterated and non-deuterated probes to elute differentially, giving rise to more than one peak. Finally, the biotinylated tags have a tendency to fragment during mass spectrometric analysis.

In view of the shortcomings of tagging methodologies as presently practiced, there is a need in the art for methods of detecting, analyzing, and identifying oxidized biomolecules in a sample, including those present only in small quantities. A method that was more versatile and robust than those methods based upon ICAT would overcome current limitations in biomolecule analysis. The present invention provides such a method.

SUMMARY OF THE INVENTION

The present invention provides bioanalytical methods and reagents for the analysis of biomolecules, particularly, oxidized biomolecules, such as, e.g., proteins, nucleic acids, lipids, and polysaccharides. The reagents comprise a chelating agent and a metal ion and are useful for fractionation and quantitative (differential) profiling of biomolecules in a complex mixture, and are referred to herein as "Element-Coded Affinity Tag" (ECAT) reagents. The ECAT reagents of the invention are useful as single tagging reagents, or as sets of two or more substantially similar but differentiable tagging reagents. The ECAT reagents can conveniently be used to detect, analyze, and identify multiple oxidized biomolecules in a single sample, or the same oxidized biomolecule in different samples. Using the methods described herein, the ECAT reagents can be used to simultaneously detect and distinguish between multiple biomolecules based on the atomic weight of the particular metal ion present in the ECAT reagent. The ECAT reagents can also be used in diagnostic and therapeutic methods to detect levels of oxidized biomolecules and patterns of biomolecule oxidation in conjunction with disease progression and regression.

One embodiment of the invention provides a method of detecting an oxidized biomolecule (e.g., presence and/or quantity) in a sample, or of identifying oxidized positions in a biomoleule. A biological sample is contacted with a tag moiety comprising a complex between a metal ion and a chelating agent comprising a functional group capable of forming a linkage (e.g., a covalent linkage) at an oxidized site on said biomolecule, under conditions sufficient to form an adduct between the biomolecule and the tag moiety; and detecting the quantity of first adduct, thereby detecting the oxidized biomolecule (e.g., presence and/or quantity) or identifying oxidized positions in the biomolecule. The biomolecule can be, e.g., a polypeptide, a nucleic acid, a polysaccharide, or a lipid. In some embodiments, the sample is isolated from a tissue suspected of being diseased (e.g., from an individual suspected of having a neurodegenerative disorder, a neoplasm, a vascular disorder, an autoimmune disease, or a bacterial or viral infection). The metal can be a lanthanide ion, an actinide ion, an alkaline earth metal ion, a transition metal ion, or a post transition metal ion. In some embodiments, the quantity of the adduct is detected by mass spectrometry, thereby detecting the oxidized biomolecule. Detection of the oxidized molecule detects the present and quantity of the oxidized biomolecule as well as oxidized sites within the biomolecule. The chelating agent can be a non-macrocylic chelating agent or a macrocylic chelating agent. In some embodiments, the chelating agent is a macrocyclic chelating agent comprising four nitrogen atoms.

In some embodiments, the present invention provides a method for comparing levels of an oxidized biomolecule between a first sample and a second sample by: contacting the first sample with a first tag moiety comprising a complex between a first metal ion and a chelating agent, thereby forming a first adduct between the biomolecule and the first tag moiety; contacting the second sample with a second tag moiety comprising a complex between a second metal ion and the chelating agent, thereby forming a second adduct between the biomolecule and the second tag moiety; and comparing the quantity of the first adduct to the quantity of the second adduct, thereby comparing the levels of the biomolecule between the first sample and the second sample. The biomolecule can be, e.g., a polypeptide, a nucleic acid, a polysaccharide, or a lipid. The first sample and second sample can be isolated from different individuals or the same individual. In some embodiments, the individual is suspected of having a disease (e.g., neurodegenerative disorders, neoplasms, vascular disorders, autoimmune disease, or bacterial or viral infection). In some embodiments, the first sample is isolated from a tissue suspected of being diseased and the second sample is from a nondiseased tissue. In some embodiments, the first metal ion and the second metal ion are independently a lanthanide ion, an actinide ion, an alkaline earth metal ion, a transition metal ion, or a post transition metal ion. In some embodiments, the quantity of the first adduct and the second adduct is determined by mass spectrometry. The chelating agent can be a non-macrocylic chelating agent or a macrocyclic chelating agent. In some embodiments, the chelating agent is a macrocyclic chelating agent comprising four nitrogen atoms.

In some embodiments, the metal chelate has four nitrogen atoms. The chelating agent may comprise a substituted or unsubstituted ethyl bridge that covalently links at least two of the nitrogen atoms. An exemplary ethyl bridge is shown in Formula I below:

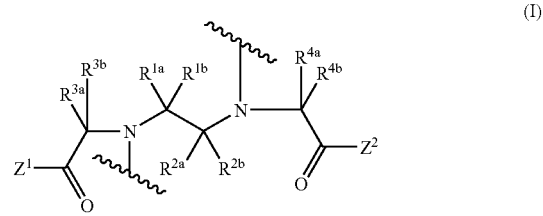

(I)

wherein $Z^1$ and $Z^2$ are members independently selected from $OR^1$ and $NR^1R^2$, in which $R^1$ and $R^2$ are members independently selected from H, substituted or unsubstituted alkyl and substituted or unsubstituted heteroalkyl. The symbols $R^{1a}$, $R^{1b}$, $R^{2a}$, $R^{2b}$, $R^{3a}$, $R^{3b}$, $R^{4a}$ and $R^{4b}$ represent members independently selected from H, substituted or unsubstituted alkyl, substituted or unsubstituted heteroalkyl, substituted or unsubstituted aryl and linker moieties.

In some embodiments, the macrocyclic chelating agent has the following formula:

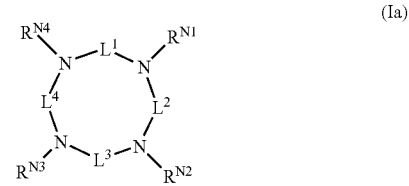

(Ia)

wherein each of $L^1$, $L^2$, $L^3$ and $L^4$ are linking groups independently selected from $C_{2-5}$ alkylene which is optionally substituted with one to three substituents selected from the group consisting of substituted and unsubstituted alkyl, substituted and unsubstituted heteroalkyl and substituted and unsubstituted aryl; each of $R^{N1}$, $R^{N2}$, $R^{N3}$ and $R^{N4}$ are independently selected from the group consisting of substituted and unsubstituted alkyl, substituted and unsubstituted heteroalkyl and substituted and unsubstituted aryl; wherein at least one of $L^1$, $L^2$, $L^3$, $L^4$, $R^{N1}$, $R^{N2}$, $R^{N3}$ and $R^{N4}$ comprise a functional group capable of forming a linkage (e.g., a covalent linkage) to an oxidized site on a biomolecule.

In some embodiments, the chelating agent has the formula:

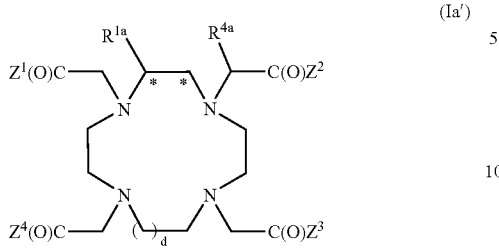

wherein $Z^1$, $Z^2$, $Z^3$ and $Z^4$ are members independently selected from $OR^1$ and $NR^1R^2$ in which $R^1$ and $R^2$ are members independently selected from H, substituted or unsubstituted alkyl and substituted or unsubstituted heteroalkyl; $R^{1a}$ and $R^{4a}$ are members independently selected from H, substituted or unsubstituted alkyl, substituted or unsubstituted heteroalkyl; substituted or unsubstituted aryl and linker moieties. At least one of $R^1$, $R^2$, $R^{1a}$, and $R^{4a}$ comprise a functional group capable of forming a linkage (e.g., a covalent linkage) to an oxidized site on a biomolecule. d is 1 or 2. The carbon atoms marked * can each be of S or R configuration.

In some embodiments, $R^{1a}$ or $R^{4a}$ comprises a moiety having the formula:

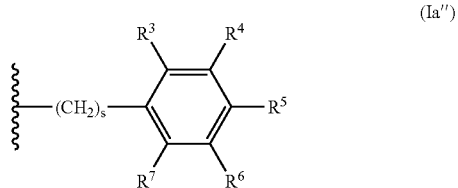

wherein
$R^3$, $R^4$, $R^5$, $R^6$ and $R^7$ are members independently selected from H, halogen, $NO_2$, CN, $X^1R^8$, $NR^9R^{10}$, and $C(=X^2)R^{11}$
wherein
$X^1$ is a member selected from O, NH and S;
$R^8$ and $R^9$ are members independently selected from H, substituted or unsubstituted alkyl, substituted or unsubstituted heteroalkyl and $C(X^3)R^{12}$
wherein
$X^3$ is a member selected from O, S and NH;
$R^{12}$ is a member selected from substituted or unsubstituted alkyl, substituted or unsubstituted heteroalkyl and $OR^{13}$
wherein
$R^{13}$ is a member selected from substituted or unsubstituted alkyl, substituted or unsubstituted heteroalkyl, substituted or unsubstituted aryl and substituted or unsubstituted heteroaryl;
$R^{10}$ is a member selected from H, substituted or unsubstituted alkyl, substituted or unsubstituted heteroalkyl and OH,
and $R^9$ and $R^{10}$, taken together are optionally (=C=S);
$X^2$ is a member selected from O, S and NH; and
$R^{11}$ is a member selected from H, halogen, substituted or unsubstituted alkyl, substituted or unsubstituted heteroalkyl, $OR^{14}$, $NR^{15}R^{16}$ wherein
$R^{14}$ is a member selected from H, substituted or unsubstituted alkyl, substituted or unsubstituted heteroalkyl, and $C(O)R^{17}$
wherein
$R^{17}$ is a member selected from substituted or unsubstituted alkyl and substituted or unsubstituted heteroalkyl;
$R^{15}$ and $R^{16}$ are members independently selected from H, substituted or unsubstituted alkyl and substituted or unsubstituted heteroalkyl; and s is 0, 1, 2, 3, 4, 5, 6, 7, 8, 9, or 10. In some embodiments, the chelating agent is selected from substituted or unsubstituted DOTA and substituted or unsubstituted TETA substituted or unsubstituted NOTA, substituted or unsubstituted DTPA substituted or unsubstituted EDTA.

In some embodiments, the method further comprises contacting the first adduct and the second adduct with an affinity medium comprising a first binding moiety that binds the first tag moiety and the second tag moiety; and eluting the first adduct and the second adduct from the affinity medium, thereby forming a solution comprising the first adduct and the second adduct. In some embodiments, the first binding moiety is a polypeptide (e.g., an antibody, including antibodies that specifically bind to a metal chelate such as 2D12.5; Protein A, Protein, or streptavidin). In some embodiments, the first tag moiety and the second tag moiety further comprise a second binding moiety that is complementary to the first binding moiety. In some embodiments, the second binding moiety is, e.g., a polypeptide, including, e.g., an antibody; or biotin.

In a further embodiment, the present invention provides an affinity medium, comprising a solid support comprising a first binding moiety that binds a tag moiety comprising a complex between a metal ion and a chelating agent. In some embodiments, the the metal ion is selected from a lanthanide ion, an actinide ion, an alkaline earth metal ion, a transition metal ion, and a post transition metal ion. In some embodiments, the first binding moiety is a polypeptide (e.g., an antibody, including antibodies that specifically bind to a metal chelate such as 2D12.5; protein A, protein G, or streptavidin). In some embodiments, the first tag moiety and the second tag moiety further comprise a second binding moiety that is complementary to the first binding moiety. In some embodiments, the second binding moiety is, e.g., a polypeptide or biotin. In some embodiments, the chelating agent is a macrocyclic chelating agent comprising four nitrogen atoms. In some embodiments, the chelating agent is compound of Formula I, Formula Ia, Formula Ia', or Fomula Ia", as described above. In some embodiments, the chelating agent is selected from, e.g., substituted or unsubstituted DOTA and substituted or unsubstituted TETA substituted or unsubstituted NOTA, substituted or unsubstituted DTPA substituted or unsubstituted EDTA.

In another embodiment, the present invention provides a kit for detecting an oxidized biomolecule (e.g., presence and/or quantity) in a sample or of identifying oxidized sites on a biomolecule. The kit comprises: at least first metal ion and a chelating agent comprising a functional group capable of forming a covalent linkage at an oxidized site on said biomolecule. The metal ion and chelating agent interact to form a tag moiety. In some embodiments, the kit further comprises a second metal ion that interacts with the chelating agents to form a second tag moiety. In some embodiments, the biomolecules is a polypeptide, a nucleic acid, a polysaccharide, or a lipid. In some embodiments, the first metal ion and the second metal ion are independently selected from a lanthanide ion, an actinide ion, an alkaline earth metal ion, a transition metal ion, and a post transition metal ion. In some embodiments, the kits further comprise a solid support comprising a first binding moiety that binds the first tag moiety and the second tag moiety. In some embodiments, the first binding moiety is a polypeptide (e.g., an antibody, including antibodies that specifically bind to a metal chelate such as 2D12.5, Protein A, Protein G, or streptavidin). In some embodiments, the first tag moiety and the second tag moiety further comprise a second binding moiety that is complementary to the first binding moiety. In some embodiments, the second binding moiety is e.g., a polypeptide, including, e.g., an antibody; or biotin. In some embodiments, the chelating agent is a macrocyclic chelating agent comprising four nitrogen atoms. In some embodiments, the chelating agent is a compound of Formula I, Formula Ia, Formula Ia', or Formula Ia", as described above. In some embodiments, the chelating agent is selected from, e.g., substituted or unsubstituted DOTA and substituted or unsubstituted TETA substituted or unsubstituted NOTA, substituted or unsubstituted DTPA substituted or unsubstituted EDTA.

BRIEF DESCRIPTION OF THE DRAWINGS

FIG. 1 is a pictorial illustration comparing an exemplary ECAT method of the invention to the ICAT method.

FIG. 3 shows exemplary ECAT reagents that are selective for amino acid residues.

FIG. 5 is a table showing the atomic weights of isotopes of selected metals, the ions of which are of use in the present invention.

FIG. 7 shows the sequences for the $V_L$ chain of 2D12.5 (SEQ ID NO: 1) and the sequences for CDR1, CDR2, and CDR3 for the $V_L$ chain of 2D12.5 (SEQ ID NOS: 2, 3, and 4, respectively). FIG. 7 also shows the sequences for the $V_H$ chain (SEQ ID NO:5) and the sequences for CDR1, CDR2, and CDR3 for the $V_H$ chain of 2D12.5 (SEQ ID NOS: 6, 7, and 8, respectively).

FIG. 8 shows the alignment of the amino acid sequence of the $V_H$ chain of 2D12.5. In particular, FIG. 8 shows the alignment of the native hybridoma sequence, the native cloned hybridoma sequence, the N87D sequence, the N87D_G53C sequence, the N87D_G54C sequence, and the N87D_G55C sequence (SEQ ID NOS.: 9, 10, 11, 12, 13, and 14, respectively). Note that the native hybridoma sequence shown corresponds to amino acids 2-119 of the $V_H$ chain of 2D12.5 as set forth in SEQ ID NO:5. Therefore, N87D is N88D, G53C is G54C, G55C is G55C, and G55C is G56C if the Kabat standard numbering system is used to determine the positions of amino acid residues in an antibody heavy chain or light chain (see, e.g., Kabat et al., *Sequences of Proteins of Immunological Interest* 5th Ed., NIH Publication No. 91-3242 (1991)).

FIG. 9 shows the alignment of the native hybridoma sequence, the native cloned hybridoma sequence, the N87D sequence, the N87D_G53C sequence, the N87D_G54C sequence, and the N87D_G55C sequence (SEQ ID NOS.: 15, 16, 17, 18, 19, and 20, respectively).

FIG. 10 shows the alignment of the amino acid sequence of the $V_L$ chain of 2D12.5. In particular, FIG. 10 shows the alignment of the native hybridoma sequence, the native cloned hybridoma sequence, and the N53C sequence (SEQ ID NOS.: 21, 22, and 23, respectively). Note that the native hybridoma sequence shown corresponds to amino acids 2-110 of the $V_L$ chain of 2D12.5 as set forth in SEQ ID NO:1. Therefore, N53C is N54C, if the Kabat standard numbering system is used.

FIG. 11 shows the alignment of the nucleotide sequence of the $V_L$ chain of 2D12.5. In particular, FIG. 11 shows the alignment of the native hybridoma sequence, the native cloned hybridoma sequence, and the N53C sequence (SEQ ID NOS.: 24, 25, and 26, respectively)

FIG. 17 shows additional exemplary ECAT reagents suitable for use in the methods of the invention.

FIG. 18 shows three exemplary approaches for attaching a biomolecule to a macrocyclic chelating agent.

FIG. 19 shows exemplary groups that can be attached to the ECAT reagents described herein.

FIG. 25 shows Tables 1A and 1B. Table 1A shows oxidized peptides (SEQ ID NOS:47-50) identified on rHSA. Table 1B shows oxidized peptides (SEQ ID NOS:51-58) identified on FeEDTA/ascorbate-oxidized rHSA. Asterisks indicate chemical modification: C* is cysteine alkylated with iodoacetamide during sample workup; R*, K*, or P* are oxidized and tagged arginine, lysine, or proline. Each residue in parentheses has been removed by trypsin during proteolysis, showing that each of these is a true tryptic peptide.

DETAILED DESCRIPTION OF THE INVENTION

I. Definitions

Figure 2:
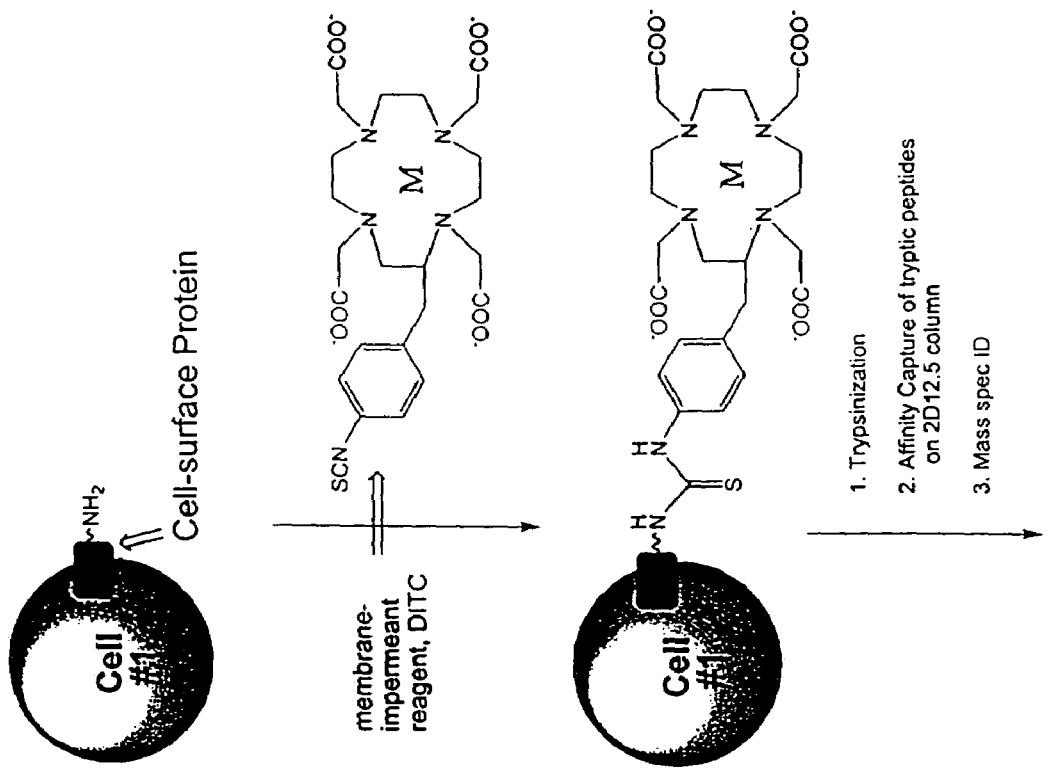
FIG. 2 is a diagram showing the use of an ECAT reagent to bind a cell surface protein. The protein is subsequently trypsinized, submitted to affinity capture on a 2D12.5 affinity column and the labeled peptides are detected and identified using mass spectrometry.
Figure 4:
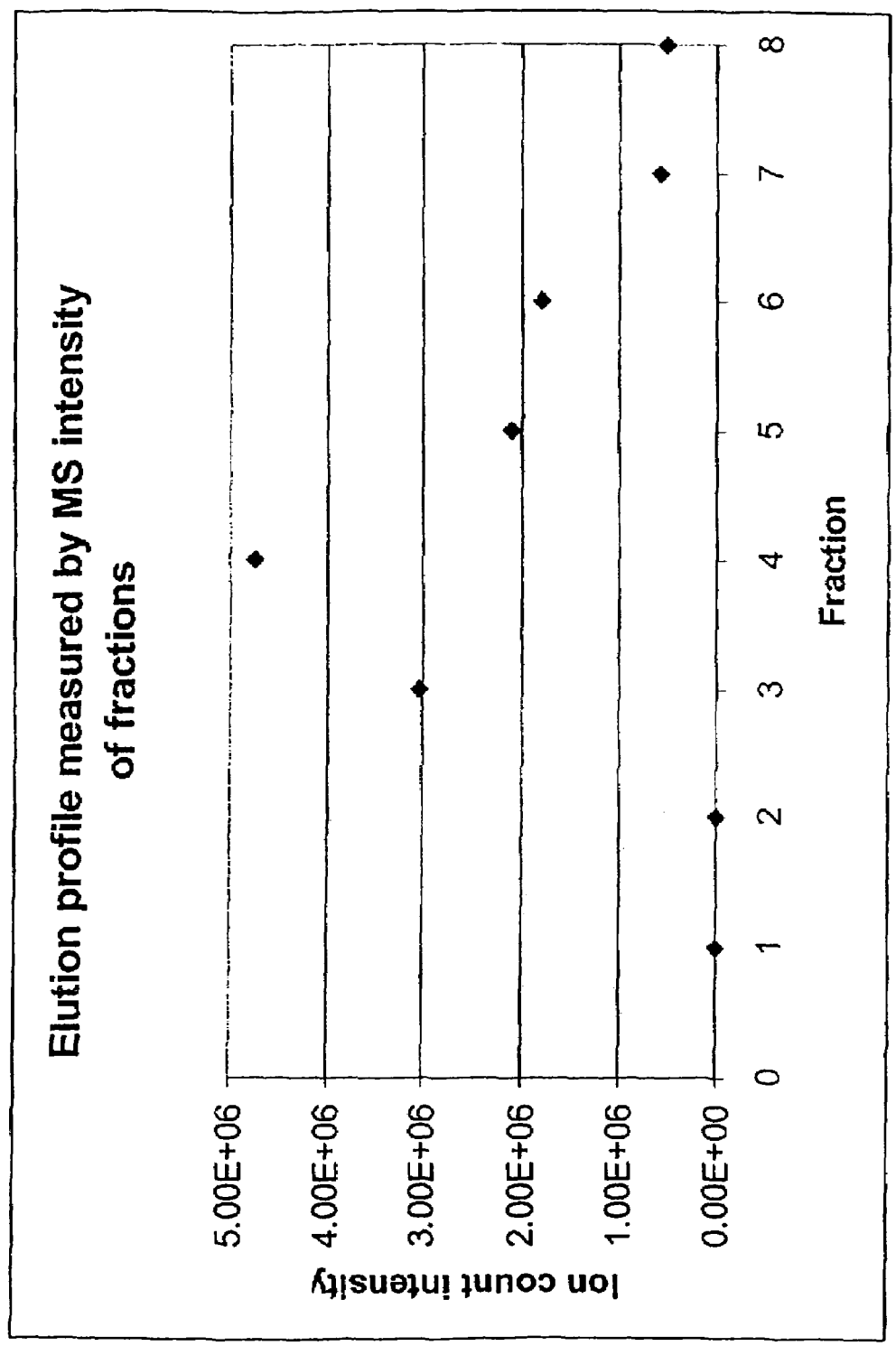
FIG. 4 is the elution profile of an ECAT-tagged peptide off of an antibody (2D12.5)-labeled affinity column.
Figure 6:
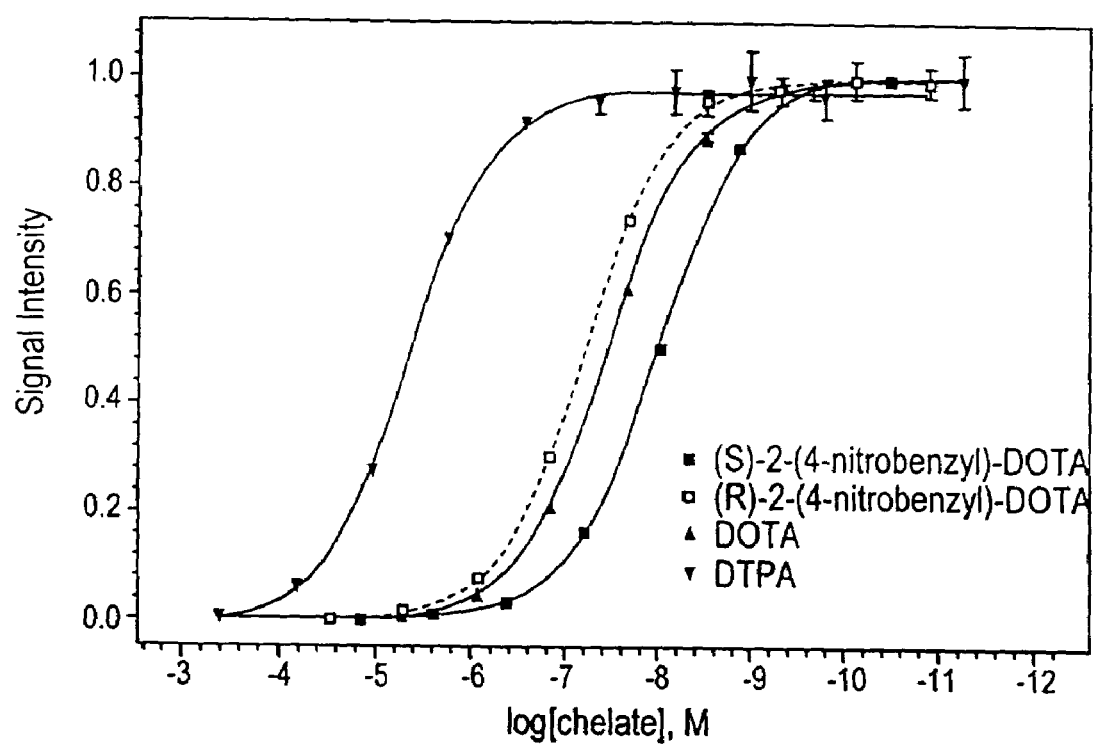
FIG. 6 is a graphical display showing the relative binding curves of an exemplary metal chelate, the Y-DOTA molecule, with different side chain locations. Changing the location of the side chain of DOTA causes a decrease in the binding affinity, but the affinity of the (5-Amino-2-methoxy-phenyl)-carboxymethyl)-DOTA is still sufficiently strong to consider for further applications. Evaluation of the crystal structure seems to indicate that shorter substitutions at this position may bind with higher affinity. Substitutions at other locations may yield reasonably high affinities as well. The (5-Amino-2-methoxy-phenyl)-carboxymethyl)-DOTA analyzed in this experiment was racemic, so it is not clear which isomer binds with higher affinity. The low pKa of the carboxymethyl proton makes it difficult to prepare a chirally pure molecule. Substitution as observed in the (S)-2-(4-nitrobenzyl)-DOTA is clearly stronger.
Figure 9:
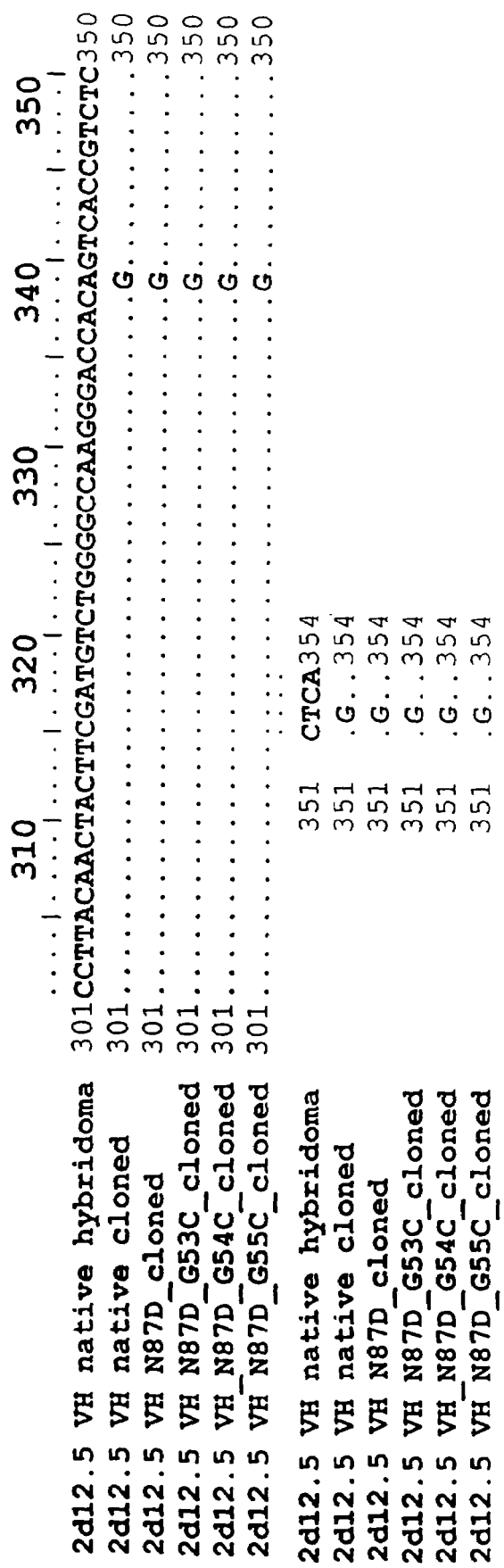
FIG. 9 shows the alignment of the nucleotide sequence of the $V_H$ chain of 2D12.5. In particular.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Tag" or "Element Coded Affinity Tag ('ECAT')" refers a moiety comprising a complex between a metal ion and a chelating agent as described in detail herein below. The chelating agents typically comprise a functional group capable of forming a covalent linkage with an oxidized site on a biomolecule. Tags are distinguishable from each others based on the differential mass of the particular metal ions in the complex. Tags can comprise any metal ion, including, e.g., any lanthanide ion, actinide ion, transition metal ion, alkaline earth metal ion, or post transition metal ion, or other metal ion, so long as the metal ion does not substantially affect the binding affinity of the biomolecule and the metal chelate. Tags can be detected when present at low concentrations (e.g., $10^{-6}$ to $10^{-15}$ mole). Tags can be attached to a biomolecule and are chemically stable toward the manipulations to which the biomolecule is subjected, including attachment and any manipulations of the biomolecule while the tag is present. Moreover, tags do not significantly interfere with the manipulations performed on the biomolecule while the tag is present.

"Biomolecule" refers to any molecule derived from a biological organism. Biomolecules may be naturally occurring or recombinant. Exemplary biomolecules include polypeptides such as, e.g., immunoglobulins, ligands, counterligands, receptors; cofactors, enzymes (e.g., kinases, phosphatases, dehydrogenases, and the like), nucleic acid binding proteins (polymerases, histones, and the like); nucleic acids (e.g., genomic DNA, cDNA, RNA), glycoproteins, lipids (e.g., fatty acids such as myristic acid, palmitic acid, palmitoleic acid, stearic acid, oleic acid, linoleic acid, linolenic acid, and arachidonic acid; sterols such as cholesterol; and sphingolipids such as sphingomyelins and glycosphingolipids), and polysaccharides (e.g., carbohydrates, lectins, and the like). Biomolecules may be oxidized. In the case of proteins, individual amino acids within the protein may be oxidized. Examples include oxidation of a sulfhdryl group on a cysteine, formation of of a disulfide bond, formation of a mixed disulfide between a sulfhydryl group and a glutathione; hydroperoxide formation on the side chains of glutamic acid, tyrosine, lysine, leucine, valine, proline, or isoleucine; formation of 2-oxo-histidine; formation of carbonyl derivatives on amino acid side chains of lysine, arginine, proline, and threonine.

"Sample" or "biological sample" as used herein is a sample of biological tissue or fluid that is suspected of containing a biomolecule of interest. Samples include, for example, body fluids such as whole blood, serum, plasma, cerebrospinal fluid, urine, lymph fluids, and various external secretions of the respiratory, intestinal and genitourinary tracts such as tears, saliva, semen, milk, and the like; and other biological fluids such as cell culture suspensions, cell extracts, cell culture supernatants. Samples may also include tissues biopsies, e.g., from the lung, liver, brain, eye, tongue, colon, kidney, muscle, heart, breast, skin, pancreas, uterus, cervix, prostate, salivary gland, and the like. A sample may be suspended or dissolved in, e.g., buffers, extractants, solvents, and the like. A sample can be from any naturally occurring organism or a recombinant organism including, e.g., viruses, prokaryotes or eukaryotes, and mammals (e.g., rodents, felines, canines, and primates). The organism may be a nondiseased organism, an organism suspected of being diseased, or a diseased organism, including a disease organism undergoing treatment for disease. Typically the disease or disorder is one in which biomolecules are oxidized. A mammalian subject from whom a sample is taken may have, be suspected of having, or be undergoing treatment for a disease such as, for example, cancer, autoimmune disease, or cardiovascular disease, pulmonary disease, gastrointestinal disease, muscoskeletal disorders, central nervous system disorders, including neurodegenerative disorders, infectious disease (e.g., viral, fungal, or bacterial infection). Specific diseases include, e.g., Alzheimer's disease, acute respiratory distress syndrome, amyotrophic lateral sclerosis, cataractogenesis, chronic lung disease, bronchopulmonary dysplasia, chronic renal failure, chronic uremia, cystic fibrosis, dementia, diabetes, ischemia-reperfusion, Parkinson's diease, preeclampsia, psoriasis, theumatori arthritis, juvenile, chronic arthritis, severe sepsis, systemic amyloidosis, and varicocele.

"Adduct refers to a complex formed by the interaction of a tag moiety with a biomolecule (e.g., a polypeptide, nucleic acid, lipid, or polysaccharide). Adducts are detected to determine the quantity of a biomolecule present in a sample. Adducts may be detected directly, or may be processed prior to detection, e.g., by enzymatic digestion and/or elution over a column such as an affinity column or a size exclusion column.

"Affinity medium" refers to a solid support attached (e.g., covalently or noncovalently) to a binding moiety (e.g., a polypeptide or nucleic acid) that specifically binds to a tag moiety, regardless of the particular metal ion present in the tag. The solid support and the binding moiety can be attached using any method known in the art including, e.g., oxidative coupling as described in, e.g., Amini et al., *Chem. and Biol.* 10:1115-1127 (2003) and Amini et al., *Angew. Chem. Int. Ed.* 41(2):356-359 (2002). Multiple solid supports are known in the art and include, for example, hydrophilic and hydrophobic resins, activated resins, metal affinity resins (e.g., nickel-based resins), metalloids, semi-conductive materials, ceramics, and the like. In addition, substances that form gels can be used. Such materials include, e.g., proteins (e.g., gelatins), lipopolysaccharides, silicates, agarose and polyacrylamides. Other materials include, e.g., glass and modified or functionalized glass, plastics (including acrylics, polystyrene and copolymers of styrene and other materials, polypropylene, polyethylene, polybutene, polyurethanes, Teflon, and the like), polysaccharides, nylon or nitrocellulose, resins, silica or silica-based materials including slicon and modified silicon, carbon, metals, inorganic glasses, plastics, and optical fiber bundles. A variety of organic and inorganic polymers, as well as other materials, both natural and synthetic, can be employed as the material for the solid support. In some cases, the solid support is porous and various pore sizes may be employed, depending on the nature of the biomolecule and particular tag moiety.

"Binding moiety" refers to a molecule that has affinity for another molecule. Typically, binding moieties refer to one member of a pair of molecules that have complementary affinity for each other such as, e.g., antibody-antigen, streptavidin-biotin, receptor-ligand, enzyme-substrate, complementary nucleic acid sequences. Molecules that have complementary affinity for each other may interact by, e.g., covalent bonds, noncovalent bonds, H-bonds, hydrophobic interactions, hydrophilic interactions, and ionic interactions. More particularly, exemplary binding molecules include, for example, polypeptides including, e.g., ligands and receptors, nucleic acid binding proteins (e.g., histones and polymerases), antibodies, protein A, protein G, enzymes, peptides (e.g., $His_2$, $His_4$ (SEQ ID NO:27), $His_6$ (SEQ ID NO:28), $His_8$ (SEQ ID NO:29), $His_{10}$ (SEQ ID NO:30), or $His_{12}$ (SEQ ID NO:31) substrates, cofactors, cell surface antigens, cancer antigens; nucleic acids (e.g., genomic DNA, cDNA, RNA); lipids (e.g., fatty acids such as myristic acid, palmitic acid, palmitoleic acid, stearic acid, oleic acid, linoleic acid, linolenic acid, and arachidonic acid; sterols such as cholesterol; and sphingolipids such as sphingomyelins and glycosphingolipids); and polysaccharides (e.g., carbohydrates, lectins, and the like). In some embodiments, the binding molecule is an antibody or antibody fragment including 2D12.5.

"Antibody" refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition, i.e., an antigen recognition domain. As used herein, "antigen recognition domain" means that part of the antibody, recombinant molecule, the fusion protein, or the immunoconjugate of the invention that recognizes the target or portions thereof. Typically the antigen recognition domain comprises the variable region of the antibody or a portion thereof, e.g., one, two, three, four, five, six, or more hypervariable regions. The terms "$V_H$" or "VH" refer to the variable region of an immunoglobulin heavy chain, including an Fv, scFv, dsFv or Fab. The terms "$V_L$" or "VL" refer to the variable region of an immunoglobulin light chain, including an Fv, scFv, dsFv or Fab.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). Thus, the term antibody, as used herein, also includes antibody fragments either produced by the modification of whole antibodies.

As used herein, "fragment" is defined as at least a portion of the variable region of the immunoglobulin molecule, which binds to its target, i.e. the antigen recognition domain or the antigen-binding region. Some of the constant region of the immunoglobulin may be included. Examples of antibody functional fragments include, but are not limited to, complete antibody molecules, humanized antibodies, antibody fragments, such as Fv, single chain Fv (scFv), hypervariable regions or complementarity determining regions (CDRs), $V_L$ (light chain variable region), $V_H$ (heavy chain variable region), Fab, F(ab)2' and any combination of those or any other portion of an immunoglobulin peptide capable of binding to target antigen (see, e.g., Fundamental Immunology (Paul ed., 4th. 1999). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., Nature 348: 552 (1990)). The term antibody also includes bivalent or bispecific molecules, diabodies, triabodies, and tetrabodies. Bivalent and bispecific molecules are described in, e.g., Kostelny et al., *J. Immunol*. 148: 1547 (1992), Pack and Pluckthun, *Biochemistry* 31: 1579 (1992), Zhu et al. *Protein Sci*. 6: 781 (1997), Hu et al. *Cancer Res*. 56: 3055 (1996), Adams et al., *Cancer Res*. 53: 4026 (1993), and McCartney, et al., *Protein Eng*. 8: 301 (1995).

A "humanized antibody" refers to an antibody in which the antigen binding loops, i.e., complementarity-determining regions (CDRs), comprised by the $V_H$ and $V_L$ regions are grafted to a human framework sequence. Typically, the humanized antibodies have the same binding specificity as the non-humanized antibodies described herein. Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al., *Nature* 321: 522 (1986); and Verhoyen et al., *Science* 239: 1534 (1988). Humanized antibodies are further described in, e.g., Winter and Milstein, *Nature* 349: 293 (1991).

"2D12.5" refers to a monoclonal antibody comprising a VH chain having the amino acid sequence set forth in SEQ ID NO: 5, 9, 10, 11, 12, 13, or 14, or encoded by the nucleic acid sequence set forth in SEQ ID NO: 15, 16, 17, 18, 19, or 20, and a VL chain having the amino acid sequence set forth in SEQ ID NO: 1, 21, 22, or 23, or encoded by the nucleic acid sequence set forth in SEQ ID NO:24, 25, or 26. 2D12.5 includes mutants of 2D12.15, fragments of 2D12.5 (e.g., Fv, dsFv, scFv, Fab, (Fab')$_2$), and humanized 2D12.5. 2D12.5 recognizes and specifically binds to the chelating agent DOTA bound to multiple metal ions, including lanthanide ions and actinide ions.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res*. 19: 5081; Ohtsuka et al. (1985) *J. Biol. Chem*. 260:2605-2608; Rossolini et al. (1994) *Mol. Cell. Probes* 8:91-98). The term nucleic acid is used interchangeably with gene, cDNA, mRNA, oligonucleotide, and polynucleotide.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25 to 100. More preferred embodiments include at least: 25%, 30%, 35%, 40%, 45%, 50%, 55%, 60%, 65%, 70%, 75%, 80%, 85%, 90%, 95%, or 99% or higher, compared to a reference sequence using the programs described herein, preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. "Substantial identity" of amino acid sequences for these purposes normally means that a polypeptide comprises a sequence that has at least 40% sequence identity to the reference sequence. Preferred percent identity of polypeptides can be any integer from 40 to 100. More preferred embodiments include at least 60%, 65%, 70%, 75%, 80%, 85%, 90%, 95%, or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Optimal alignment of sequences for comparison may be conducted by the local identity algorithm of Smith and Waterman (1981) *Add. APL. Math*. 2: 482, by the identity alignment algorithm of Needleman and Wunsch (1970) *J. Mol. Biol*. 48: 443, by the search for similarity method of Pearson and Lipman (1988) *Proc. Natl. Acad. Sci. U.S.A*. 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

A preferred example of algorithms that are suitable for determining percent sequence identity and sequence similarity are the BLAST and BLAST 2.0 algorithms, which are described in Altschul et al. (1977) *Nuc. Acids Res*. 25: 3389-3402 and Altschul et al. (1990) *J. Mol. Biol*. 215: 403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both Another indication that nucleotide sequences are substantially identical is if two molecules hybridize to each other, or to a third nucleic acid, under moderately, and preferably highly, stringent conditions. Stringent conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

For the purpose of the invention, suitable "moderately stringent conditions" include, for example, prewashing in a solution of 5×SSC, 0.5% SDS, 1.0 mM EDTA (pH 8.0), hybridizing at 50° C.-65° C., 5×SSC overnight, followed by washing twice at 65° C. for 20 minutes with each of 2×, 0.5× and 0.2×SSC (containing 0.1% SDS). Such hybridizing DNA sequences are also within the scope of this invention. As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a quencher, a fluorophore or another moiety.

"Peptide," "polypeptide" or "protein" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983). The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxy-glutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, amide linkages are represented by both —CONH or NHCO—.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —$SR^1$, -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R'" and R"" are preferably independently selected from hydrogen, (unsubstituted aryl)-(C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

The symbol ∿∿, whether utilized as a bond or displayed perpendicular to a bond indicates the point at which the displayed moiety is attached to the remainder of the molecule, solid support, etc.

II. General

The methods of separating, analyzing and identifying proteins using isotope-coded affinity tag (ICAT) reagents and biotin-streptavidin affinity columns are hampered by a number of shortcomings. First, methods using ICAT reagents are limited to differential analysis of two samples, based on weight differences between two isotopes of the same element. Second, the methods require derivitization of cysteine (Cys), an amino acid of low abundance (i.e., about 2.2%) in most proteins. Moreover, many proteins are naturally biotinylated and bind to streptavidin affinity columns regardless of whether they are tagged with an ICAT reagent, thus creating high background interference during analysis and identification. In addition the ICAT methods require synthesis and use of isotope pairs such as D/H and C12/C13.

The present invention provides methods for separating, analyzing and identifying biomolecules using complexes between metal ions and chelating agents. More particularly, the invention provides methods of using Element-Coded Affinity Tags (ECAT) comprising a complex between a metal ion and a chelating agent to analyze and identify biomolecules that are oxidized. For example, the ECAT reagents can be used to detect oxidized biomolecules, to identify oxidized sites in a biomolecule, and to identify oxidation patterns of a biomolecule. In some embodiments, the ECAT reagents are used to diagnose disease by detecting and/or quantifying oxidized biomolecules. In some embodiments, the ECAT reagents can be used to monitor the progression of disease and the efficacy of therapeutic regimens used to treat disease, e.g., by detecting the oxidation levels and oxidation patterns of biomolecules in a disease subject.

The chelating agents comprise a reactive group that can interact with and bind to a group on the biomolecule. For example, an ECAT comprising a complex between a metal ion and a chelating agent is contacted with a biological sample for form an ECAT-oxidized biomolecule adduct. The amount of the adduct is detected based on the atomic weight of the metal ion and presence and quantity of the oxidized biomolecule is detected. To identify oxidation sites within a biomolecule, an ECAT comprising a complex between first metal ion and a chelating agent and a second ECAT comprising a complex between a second metal ion and a chelating agent is contacted with a sample to form a first ECAT-oxidized biomolecule adduct and a second ECAT-oxidized biomolecule adduct. The amount of the first adduct and the amount of the second adduct are measured based on the atomic weight of the metal ion in each sample (e.g., by mass spectrometry of the adducts), and the oxidized sites within the oxidized biomolecule are identified. To compare multiple samples, an ECAT comprising a complex between first metal ion and a chelating agent is contacted with a first sample and a second ECAT comprising a complex between a second metal ion and a chelating agent is contacted with a second sample to form a first ECAT-biomolecule adduct and a second ECAT-biomolecule adduct. The amount of the first adduct and the amount of the second adduct are measured based on the atomic weight of the metal ion in each sample (e.g., by mass spectroscopy of the adducts), and the level of the biomolecule present in each sample is determined. More than two ECAT reagents can be used to compare multiple samples; as long as ECAT reagent comprises a different metal ion (e.g., a lanthanide ion, an actinide ion, an alkaline earth metal ion, a transition metal ion, and a post transition metal ion). The ECAT reagents can conveniently be used in conjunction with a broad range of analytical formats including, but not limited to the multiplexed qualitative and/or quantitative analysis of biomolecules.

In some embodiments, the ECAT-biomolecule adducts are combined and contacted with a solid support attached to a binding moiety (e.g., a polypeptide such as an antibody or a receptor) that specifically binds to the ECAT reagent, regardless of which metal ion is present in the reagent. The bound ECAT-biomolecule adducts can be eluted from the solid support generate a pool comprising all of the ECAT-biomolecule adducts. A single measurement can be taken to determine the amount of each adduct present in the pool, thus providing a differential analysis of the amount of biomolecule present in each sample. Furthermore, metal chelate-based ECAT reagents are markedly resistant to degradation, fragmentation, etc. under the sample conditions necessary for acquiring mass spectra and are also stable to enzymatic digest. In some embodiments, the solid support is in a column format.

Thus, in contrast to the ICAT-based system, samples tagged with ECAT reagents can be distinguished based on the mass differences between the particular metal ions present in each complex and, accordingly, differential analysis is not limited to two samples. In addition, methods using ECAT reagents do not require biotinylation of the biomolecule being analyzed. Thus, the methods of the invention provide multiple advantages over methods currently used to separate, analyze, and identify biomolecules.

III. Tag Moieties

Tag moieties or Element-Coded Affinity Tags (ECAT) comprise a chelating agent and a metal ion. The tags can be distinguished from each other based on the atomic weight of the metal ion present in the tag. In some embodiments, the tags comprise a chelating agent-metal ion complex that is specifically recognized by an antibody antigen recognition domain and which form covalent bonds with one or more reactive functional group on a biomolecule.

Suitable chelating agents include non-macrocylic chelating agents (e.g., linear or branched) and macrocyclic chelating agents. Typically the chelating agent comprises a functional group capable of forming a linkage (e.g., a covalent linkage) with an oxidized site on a biomolecule.

In some embodiments, the metal chelate has four nitrogen atoms. The chelating agent may comprise a substituted or unsubstituted ethyl bridge that covalently links at least two of the nitrogen atoms. An exemplary ethyl bridge is shown in Formula I below:

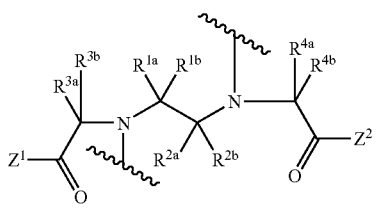

(I)

wherein $Z^1$ and $Z^2$ are members independently selected from $OR^1$ and $NR^1R^2$, in which $R^1$ and $R^2$ are members independently selected from H, substituted or unsubstituted alkyl and substituted or unsubstituted heteroalkyl. The symbols $R^{1a}$, $R^{1b}$, $R^{2a}$, $R^{2b}$, $R^{3a}$, $R^{3b}$, $R^{4a}$ and $R^{4b}$ represent members independently selected from H, substituted or unsubstituted alkyl, substituted or unsubstituted heteroalkyl, substituted or unsubstituted aryl and linker moieties.

In some embodiments, the chelate has the following formula:

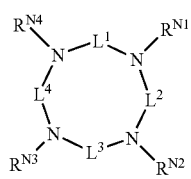

(Ia)

wherein each of $L^1$, $L^2$, $L^3$ and $L^4$ are linking groups independently selected from $C_{2-5}$ alkylene which is optionally substituted with one to three substituents selected from the group consisting of substituted and unsubstituted alkyl, substituted and unsubstituted heteroalkyl and substituted and unsubstituted aryl; each of $R^{N1}$, $R^{N2}$, $R^{N3}$ and $R^{N4}$ are independently selected from the group consisting of substituted and unsubstituted alkyl, substituted and unsubstituted heteroalkyl and substituted and unsubstituted aryl; wherein at least one of $L^1$, $L^2$, $L^3$, $L^4$, $R^{N1}$, $R^{N2}$, $R^{N3}$ and $R^{N4}$ comprise a functional group capable of forming a linkage (e.g., a covalent linkage) to an oxidized site on a biomolecule.

In another embodiment, the chelate has the following formula:

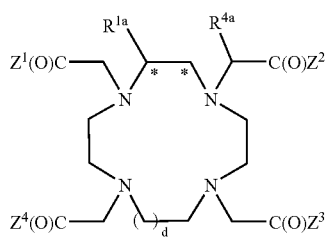

(Ia')

wherein $Z^1$, $Z^2$, $Z^3$ and $Z^4$ are members independently selected from $OR^1$ and $NR^1R^2$, in which $R^1$ and $R^2$ are members independently selected from H, substituted or unsubstituted alkyl and substituted or unsubstituted heteroalkyl. $R^{1a}$ and $R^{4a}$ are members independently selected from H, substituted or unsubstituted alkyl, substituted or unsubstituted heteroalkyl; substituted or unsubstituted aryl and linker moieties. At least one of $R^1$, $R^2$, $R^{1a}$, and $R^{4a}$ comprise a functional group capable of forming a linkage (e.g., a covalent linkage) to an oxidized site on a biomolecule. d is 1 or 2. The carbon atoms marked * can each be of S or R configuration.

In another exemplary embodiment, the ECAT reagent includes a moiety having the following formula:

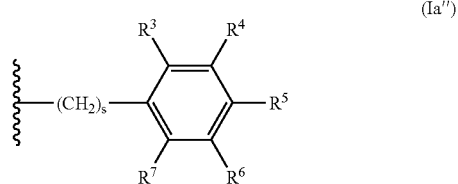

(Ia'')

wherein $R^3$, $R^4$, $R^5$, $R^6$ and $R^7$ are members independently selected from H, halogen, $NO_2$, CN, $X^1R^8$, $NR^9R^{10}$, and $C(=X^2)R^{11}$. The symbol $X^1$ represents a member selected from O, NH and S. The symbols $R^8$ and $R^9$ are members independently selected from H, substituted or unsubstituted alkyl, substituted or unsubstituted heteroalkyl and $C(X^3)R^{12}$, in which $X^3$ is a member selected from O, S and NH. $R^{12}$ is a member selected from substituted or unsubstituted alkyl, substituted or unsubstituted heteroalkyl and $OR^{13}$, in which $R^{13}$ is a member selected from substituted or unsubstituted alkyl, substituted or unsubstituted heteroalkyl, substituted or unsubstituted aryl and substituted or unsubstituted heteroaryl. The symbol $R^{10}$ is a member selected from H, substituted or unsubstituted alkyl, substituted or unsubstituted heteroalkyl and OH, and $R^9$ and $R^{10}$, taken together are optionally (=C=S). $X^2$ is a member selected from O, S and NH. The symbol $R^{11}$ represents a member selected from H, halogen, substituted or unsubstituted alkyl, substituted or unsubstituted heteroalkyl, $OR^{14}$, $NR^{15}R^{16}$. $R^{14}$ is a member selected from H, substituted or unsubstituted alkyl, substituted or unsubstituted heteroalkyl, and $C(O)R^{17}$. $R^{17}$ is a member selected from substituted or unsubstituted alkyl and substituted or unsubstituted heteroalkyl; and $R^{15}$ and $R^{16}$ are members independently selected from H, substituted or unsubstituted alkyl and substituted or unsubstituted heteroalkyl.

Exemplary chelating agents of use in the present invention include, but are not limited to, reactive chelating groups capable of chelating radionuclides include macrocycles, linear, or branched moieties. Examples of linear or branched moieties include, e.g., diethylenetriamine-N,N,N',N',N''-pentaacetic acid ("DTPA") and ethylenediamine-N,N,N',N'-tetraacetic acid ("EDTA"). Examples of macrocyclic chelating moieties include polyaza- and polyoxamacrocycles, polyether macrocycles, crown ether macrocycles, and cryptands (see, e.g., Synthesis of Macrocycles: the Design of Selective Complexing Agents (Izatt and Christensen ed., 1987) and The Chemistry of Macrocyclic Ligand Complexes (Lindoy, 1989)). Examples of polyazamacrocyclic moieties include those derived from compounds such at 1,4,7,10-tetraazacyclododecane-N,N',N'',N'''-tetraacetic acid ("DOTA"); 1,4,7,10-tetraazacyclotridecane-N,N',N'',N'''-tetraacetic acid ("TRITA"); 1,4,8,11-tetraazacyclotetradecane-N,N',N'',N'''-tetraacetic acid ("TETA"); and 1,5,9,13-tetraazacyclohexadecane-N,N',N'',N'''-tetraacetic acid (abbreviated herein abbreviated as "HETA"). Exemplary chelating agents useful in the methods described herein are shown in FIG. 3. Additional suitable chelating agents include, e.g., 1,4,7-triazacyclononane-N,N',N" triacetic acid (NOTA) as described in, e.g., Studer and Meares, *Bioconjugate Chemistry* 3:337-341 (1992)).

One of skill in the art will appreciate that chelates suitable for use in the present invention interact with any metal ion including, e.g., any lanthanide ion, actinide ion, transition metal ion, alkaline earth metal ion, or post transition metal ion, or other metal ion, so long as the metal ion does not substantially affect the binding affinity of the biomolecule and the tag moiety. Typically, the lanthanide is La, Ce, Pr, Nd, Sm, Eu, Gd, Tb, Dy, Ho, Er, Ym, Yb, Lu, or Pm. Typically, the actinide is Ac, Pa, or Am. Typically, the group IIb transition metal is Y or Sc. Typically, the alkaline earth metal is Sr. Typically, the post transition metal is Al, In, Ti, or Bi. Additional suitable metals include, for example, Mg, Ca, Sr, Ba, Ra, Th, Zr, Hf, Rf, U, V, Nb, Ta, Db, Pm, Np, Cr, Mo, W, Sg, Pu, Mn, Tc, Re, Bh, Fe, Ru, Os, Hs, Cm, Co, Rh, Ir, Mt, Bk, Ni, Pd, Pt, Cf, Cu, Ag, Au, Es, Zn, Cd, Hg, Er, Fm, Ga, In, Tl, Tm, Md, Sn, Pb, Yb, No, Sb, Lr, or Po.

Chelating moieties having carboxylic acid groups, such as DOTA, TRITA, HETA, and HEXA, may be derivatized to convert one or more carboxylic acid groups to reactive groups. Alternatively, a methylene group adjacent to an amine or a carboxylic acid group can be derivatized with a reactive functional group. Additional exemplary chelates of use in the present invention are set forth in Meares et al., U.S. Pat. No. 5,958,374 and Liu and Edwards, *Bioconjugate Chem.* 12:7-34 (2001), the disclosures of which are hereby incorporated by reference.

The preparation of chelates useful in practicing the present invention is accomplished using art-recognized methodologies or modifications thereof. In a preferred embodiment of the invention, a reactive derivative of DOTA is used. Preparation of DOTA is described in, e.g., Moi et al., *J. Am. Chem. Soc.* 110:6266-67 (1988) and Renn and Meares, *Bioconjugate Chem.* 3:563-69 (1992).

The structure of the ECAT reagent will, of course, depend on the ultimate application of the invention. In some cases, the ECAT reagents of the present invention also comprise a moiety that is reactive with a biomolecule. For example, where the biomolecule being detected is a polypeptide, the ECAT reagents include an "protein reactive" moiety that is capable of reacting with groups on the polypeptide including, but not limited to, amino acids (e.g., including amino acid side chains) and modified amino acids (e.g., including amino acids having modified side chains or amino acids with sugars attached). The protein reactive moiety may bind a specific amino acid side chain (e.g., the thio group of cysteine; the guanidinium group of arginine; the imidazole group of histidine) or a post-transitionally modified amino acid side chain. Alternatively, the protein reactive moiety may have an affinity for certain three-dimensional structural elements of proteins or peptides, or to defined amino acid patterns or any other element of a protein or peptide that could be chemically reactive.

In addition, the ECAT reagent of the present invention may also include one or more additional moieties, including, for example, a binding molecule (e.g., a binding molecule with complementary affinity to a binding molecule on an affinity media used to purify the ECAT-biomolecule adducts), a label (e.g., a fluorescent or luminescent label), a group that allows for and/or enhances separation of the biomolecules tagged by the ECAT reagents (e.g., a molecule having an enzymatic cleavage site, a molecule having a chemical cleavage site, a molecule that enhances the interaction between the ECAT reagent and an affinity medium), a group that enhances the interaction between the ECAT reagent and the biomolecule of interest (e.g., by increasing the avidity or specificity of the interaction). Preferably the additional moieties are positioned such that they do not affect the ability of the ECAT to bind to a biomolecule or the ability of the ECAT to bind any additional binding molecules. If the additional moiety is a binding molecule, it can be selected such that it has complementary affinity to a second binding molecule used to further isolate, characterize, or detect the biomolecule. Suitable binding molecule pairs include, e.g., streptavidin-biotin, antibody-antigen, receptor-ligands, and complementary nucleic acids.

Although many ECAT reagents fall within the scope of the present invention, some specific examples are set forth herein. In one embodiment, the ECAT reagent is selectively reactive towards the sulfhydryl group. An exemplary reactive functional group displaying selective reactivity towards the sulfhydryl group is the halo-acetyl moiety. The reactive functional group is bound to the metal chelating portion of the ECAT reagent via a linker arm, e.g., substituted or unsubstituted alkyl, substituted or unsubstituted heteroalkyl, etc. The chelating agent is preferably selected so that it, or its metal chelates are recognized by and interact reversibly with a polypeptide, such as an antibody. The interaction is optionally disrupted by exposing the antibody (metal) chelate-complex to conditions sufficient to disrupt the interaction between the antibody and the (metal) chelate. An exemplary motif for the ECAT reagents of the invention utilizes a macrocyclic chelating agent, such as a DOTA or TETA moiety.

The chelate reactive functional group(s), is located at any position on the metal chelate. Reactive groups and classes of reactions useful in practicing the present invention are generally those that are well known in the art of bioconjugate chemistry. Currently favored classes of reactions available with reactive chelates are those that proceed under relatively mild conditions. These include, but are not limited to nucleophilic substitutions (e.g., reactions of amines and alcohols with acyl halides, isothiocynates, active esters), electrophilic substitutions (e.g., enamine reactions), substitution of thiols with alkyl halides, and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive pendant functional groups include, for example:
  (a) carboxyl groups and various derivatives thereof including, but not limited to, N-hydroxysuccinimide esters, N-hydroxybenztriazole esters, acid halides (e.g., I, Br, Cl), acyl imidazoles, thioesters, p-nitrophenyl esters, alkyl, alkenyl, alkynyl and aromatic esters;
  (b) hydroxyl groups, which can be converted to, e.g., esters, ethers, aldehydes, etc.
  (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;
  (d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) isothiocyanates and isocyanates, which can react with, for example, any nucleophile including, e.g., a hydroxyl or amino group; and (m) aminooxy and carbonyl reactive pairs.

The reactive functional groups can be chosen such that they do not participate in, or interfere with, the reactions necessary to assemble the reactive chelates. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In another exemplary embodiment, the ECAT reagent comprises is a 1,2-dicarbonyl moiety, making the ECAT reagent specific for the amino acid residue, arginine. The 1,2 dicarbonyl moiety condenses with the guanidino moiety of arginine to yield an imidazolone adduct. In other exemplary embodiments, ECAT reagent binds to other amino acid residues (either one or more than one) or other protein structural elements, such as disulfide bonds.

The use of any two versions of an ECAT reagent is preferably sufficient to distinguish tagged biomolecules from different samples (e.g., normal and diseased samples). Because they have different masses, the ECAT reagents (and therefore ECAT-biomolecule adducts) are distinguishable by mass spectrometry. As an illustrative example, two versions of an ECAT reagent, identical except for the mass tag they carry, are used. One version of the ECAT reagent is contacted with a first sample while the other version is contacted with a second sample. Once isolated, the labeled proteins from the two samples are analyzed, optionally simultaneously, by mass spectrometry. Peaks corresponding to proteins from the first sample are differentiated from peaks corresponding to proteins from the second sample based on mass: the peaks separated by the difference in mass between the two ECAT moieties. This process allows for multiplexing of analysis by analyzing two or more samples at the same time. In addition, provided the samples have been handled in the same way, the differentially labeled biomolecules serve as internal standards, facilitating quantitative determination by mass spectrometry of the relative amounts of the biomolecules in the different samples.

The ECAT reagents can be functionalized to interact with any biomolecule using methods known in the art. For example, ECAT reagents can be modified to bind peptide nucleic acids as described in, e.g., Lewis et al., *Bioconjug. Chem.* 13(6): 1176-80 (2002), lipids, and polysaccharides.

IV. Affinity Media

The present invention also provides an affinity medium that is useful to isolate the ECAT-biomolecule adducts. The affinity medium binds to the ECAT reagent, thus forming a complex with the ECAT-biomolecule adduct. The bound ECAT-biomolecule adduct can then be further analyzed and purified to determine the quantity and amount of the biomolecule present in the sample, based on the identity of the metal ion present in the ECAT reagent. The affinity medium may be in multiple formats, including, e.g., a suspension in a single vessel (e.g., a tube), suspensions multiple vessels (e.g., a multiwell plate), or a column. In some embodiments, the affinity medium is a polypeptide such as an antibody. The antibody binds to the ECAT-biomolecule adduct, forming a complex that can conveniently be directly purified using any method known in the art. For example, size exclusion chromatography using commercially available media can be used to isolate the antibody-ECAT-biomolecule complex. One advantage of this embodiment, is that there is no need for construction of an additional solid support for attachment of the binding molecule.

In some embodiments, the affinity media comprises solid support attached to a binding molecule (e.g., a polypeptide or a nucleic acid). In these embodiments, the binding molecule interacts with and immobilizes the ECAT-biomolecule adduct on the support, regardless of the metal ion present in the ECAT reagent. The ECAT-biomolecule adduct is eluted from the affinity medium and the adduct is analyzed using methods known in the art. The "promiscuity" of the binding molecules allows for the design of different diagnostic and treatment regimens using a single binding molecule or a small cohort of binding molecules. In an exemplary embodiment, multiple types of the ECAT-biomolecule adducts are co-eluted from the affinity medium and identified based on the atomic weight of the particular metal ion in the ECAT reagent.

The binding molecule is bound to the support via a bond that is essentially stable to the conditions used to immobilize and release the ECAT-biomolecule adduct. Alternatively, the binding molecule is tethered to the medium by means of a bond that can be cleaved, to release the entire binding molecule-ECAT-tagged-analyte complex from the medium. In some embodiments, the binding molecule tethered to the medium can include a reactive functional group that is complementary in reactivity to a reactive functional group on the chelating agent. After immobilization of the tagged biomolecule by the binding molecule, the two complementary reactive functional groups form a covalent bond, binding the biomolecule to the binding molecule.

As defined above, the binding molecule are molecules that have affinity for another molecule, typically the binding molecule is a member of a pair of molecules with complementary affinity. Exemplary binding molecules include, e.g., ligands and receptors, nucleic acid binding proteins, antibodies, protein A, protein G, enzymes, peptides, substrates, cofactors, nucleic acids, lipids, and polysaccharides. In some embodiments, the binding molecule is an antibody or antibody fragment including 2D12.5. Methods of attaching binding molecules to a solid support are well known in the art and are described in, e.g., Amini et al., *Chem. and Biol.* 10:1115-1127 (2003) and Amini et al., *Angew. Chem. Int. Ed.* 41(2):356-359 (2002).

A. Binding Molecules

As discussed in detail above, binding molecules include, e.g., polypeptides, nucleic acids, lipids, and polysaccharides. In some embodiments, the binding molecules bind directly to the ECAT reagents. In other embodiments, the binding molecules bind to the ECAT reagent via a second binding molecule that is complementary to the first binding molecules. The binding molecules may be naturally occurring or they may be synthesized using recombinant and chemical means known to those of skill in the art. For example, isolation and synthesis of polypeptides and nucleic acids is described in e.g., Ausubel et al., supra and Sambrook et al., supra; isolation and synthesis of lipids is described in, e.g., Gunstone, *Lipid Synthesis and Manufacture* (1998); isolation and synthesis of polysaccharides is described in Gross et al., *Biopolymers from Polysaccharides and Agroproteins* (2001).

In an exemplary embodiment, the binding molecule is polypeptide which recognizes and binds to an array of macrocyclic metal chelates, each of are bound to a different metal ion. In one embodiment, the polypeptide is an antibody such as 2D12.5, i.e., a monoclonal antibody comprising a VH chain having the amino acid sequence set forth in SEQ ID NO: 5, 9, 10, 11, 12, 13, or 14, or encoded by the nucleic acid sequence set forth in SEQ ID NO: 15, 16, 17, 18, 19, or 20, and a VL chain having the amino acid sequence set forth in SEQ ID NO: 1, 21, 22, or 23, or encoded by the nucleic acid sequence set forth in SEQ ID NO:24, 25, or 26.

Methods of producing monoclonal and polyclonal antibodies and modifications and fragments thereof are known to those of skill in the art (see, for example, Kohler & Milstein, *Eur. J. Immunol.* 6: 511-519 (1976)); Kohler & Milstein, *Nature* 256: 495-497 (1975); Kozbor et al., *Immunology Today* 4: 72 (1983); Cole et al., pp. 77-96 in MONOCLONAL ANTIBODIES AND CANCER THERAPY, Alan R. Liss, Inc. (1985); and Huse et al., *Science* 246: 1275-1281 (1989). Specific polyclonal antisera and monoclonal antibodies will usually bind with a $K_d$ of at least about 0.1 mM, more usually at least about 1 µM, preferably, at least about 0.1 µM or better, and most preferably, 0.01 µM or better.

Techniques for the production of single chain antibodies (U.S. Pat. No. 4,946,778) can be adapted to produce antibodies to reactive chelates and other diagnostic, analytical and therapeutic agents. Also, transgenic mice, or other organisms such as other mammals, may be used to express humanized antibodies. Alternatively, phage display technology can be used to produce and identify antibodies and heteromeric Fab fragments that specifically bind to selected antigens (see, e.g., McCafferty et al., *Nature* 348: 552-554 (1990); Marks et al., *Biotechnology* 10: 779-783 (1992)).

In some embodiments, the antibodies are labeled, e.g., with fluorescent agents as is well known in the art. Fluorescent labeled antibodies can be used in immunohistochemical staining (Osborn et al., *Methods Cell Biol.* 24: 97-132 (1990); in flow cytometry or cell sorting techniques (Ormerod, M. G. (ed.), FLOW CYTOMETRY. A PRACTICAL APPROACH, IRL Press, New York, 1990); for tracking and localization of antigens, and in various double-staining methods (Kawamura, A., Jr., FLUORESCENT ANTIBODY TECHNIQUES AND THEIR APPLICATION, Univ. Tokyo Press, Baltimore, 1977).

Many reactive fluorescent labels are available commercially (e.g., Molecular Probes, Eugene, Oreg.) or they can be synthesized using art-recognized techniques. In an exemplary embodiment, an antibody of the invention is labeled with an amine-reactive fluorescent agent, such as fluorescein isothiocyanate under mildly basic conditions. For other examples of antibody labeled antibodies, (see, Goding, *J. Immunol. Methods* 13: 215-226 (1976); and in, MONOCLONAL ANTIBODIES: PRINCIPLES AND PRACTICE, pp. 6-58, Academic Press, Orlando (1988).

The heterodimers of heavy and light chain domains that occur in whole IgG, for example, are connected by a disulfide bond, but $F_v$ fragments lack this connection. Although native unstabilized $F_v$ heterodimers have been produced from unusual antibodies (Skerra et al., *Science*, 240: 1038-1041 (1988); Webber et al., *Mol. Immunol.* 4: 249-258 (1995)), generally $F_v$ fragments by themselves are unstable because the $V_H$ and $V_L$ domains of the heterodimer can dissociate (Glockshuber et al., *Biochemistry* 29: 1362-1367 (1990)). This potential dissociation results in drastically reduced binding affinity and is often accompanied by aggregation.

Solutions to the stabilization problem have resulted from a combination of genetic engineering and recombinant protein expression techniques. Such techniques are of use in constructing the antibodies of the present invention. The most common method of stabilizing $F_v$s is the covalent connection of $V_H$ and $V_L$ by a flexible peptide linker, which results in single chain $F_v$ molecules (see, Bird et al., *Science* 242: 423-426 (1988); Huston et al., *Proc. Natl. Acad. Sci. USA* 16: 5879-5883 (1988)). The single chain $F_v$s (sc$F_v$s) are generally more stable than $F_v$s alone.

Another way to generate stable recombinant $F_v$s is to connect $V_H$ and $V_L$ by an interdomain disulfide bond instead of a linker peptide; this technique results in disulfide stabilized $F_v$ (ds$F_v$). The ds$F_v$s solve many problems that can be associated with sc$F_v$s: they are very stable, often show full antigen binding activity, and sometimes have better affinity than sc$F_v$s (Reiter et al., *Int. Cancer* 58: 142-149 (1994)). Thus, in another preferred embodiment, the antibody of the invention is a sc$F_v$s.

Peptide linkers, such as those used in the expression of recombinant single chain antibodies, may be employed as the linkers and connectors of the invention. Peptide linkers and their use are well known in the art. (See, e.g., Huston et al., 1988; Bird et al., 1983; U.S. Pat. No. 4,946,778; U.S. Pat. No. 5,132,405; and Stemmer et al., Biotechniques 14:256-265 (1993)). The linkers and connectors are flexible and their sequence can vary. Preferably, the linkers and connectors are long enough to span the distance between the amino acids to be joined without putting strain on the structure. For example, the linker (Gly$_4$Ser)$_3$ (SEQ ID NO:32) is a useful linker because it is flexible and without a preferred structure (Freund et al., *Biochemistry* 33: 3296-3303 (1994)).

After the stabilized immunoglobulin has been designed, a gene encoding at least $F_v$ or a fragment thereof is constructed. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)).

The present invention provides for the expression of nucleic acids encoding essentially any antibody that can be raised against a metal chelate, preferably a series of metal chelates that differ only in the identity of the complexed metal ion. In some embodiments, the antibody is 2D12.5.

Those of skill in the art will understand that substituting selected codons from the above-recited sequences with equivalent codons is within the scope of the invention. Oligonucleotides that are not commercially available are preferably chemically synthesized according to the solid phase phosphoramidite triester method first described by Beaucage & Caruthers, *Tetrahedron Letts.* 22: 1859-1862

(1981), using an automated synthesizer, as described in Van Devanter et. al., *Nucleic Acids Res.* 12: 6159-6168 (1984). Purification of oligonucleotides is accomplished by any art-recognized method, e.g., native acrylamide gel electrophoresis or by anion-exchange HPLC as described in Pearson & Reanier, *J. Chrom.* 255: 137-149 (1983).

The sequence of the cloned genes and synthetic oligonucleotides can be verified after cloning using art-recognized methods, e.g., the chain termination method for sequencing double-stranded templates of Wallace et al., *Gene* 16: 21-26 (1981).

One preferred method for obtaining specific nucleic acid sequences combines the use of synthetic oligonucleotide primers with polymerase extension or ligation on a mRNA or DNA template. Such a method, e.g., RT-PCR, or LCR, amplifies the desired nucleotide sequence, which is often known (see, U.S. Pat. Nos. 4,683,195 and 4,683,202). Restriction endonuclease sites can be incorporated into the primers. Amplified polynucleotides are purified and ligated into an appropriate vector. Alterations in the natural gene sequence can be introduced by techniques such as in vitro mutagenesis and PCR using primers that have been designed to incorporate appropriate mutations.

An exemplary method of constructing the immunoglobulin is by overlap extension PCR. In this technique, individual fragments are first generated by PCR using primers that are complementary to the immunoglobulin sequences of choice. These sequences are then joined in a specific order using a second set of primers that are complementary to "overlap" sequences in the first set of primers, thus linking the fragments in a specified order. Other suitable $F_v$ fragments can be identified by those skilled in the art.

The immunoglobulin, e.g., $F_v$, is inserted into an "expression vector," "cloning vector," or "vector." Expression vectors can replicate autonomously, or they can replicate by being inserted into the genome of the host cell. Often, it is desirable for a vector to be usable in more than one host cell, e.g., in *E. coli* for cloning and construction, and in a mammalian cell for expression. Additional elements of the vector can include, for example, selectable markers, e.g., tetracycline resistance or hygromycin resistance, which permit detection and/or selection of those cells transformed with the desired polynucleotide sequences (see, e.g., U.S. Pat. No. 4,704,362). The particular vector used to transport the genetic information into the cell is also not particularly critical. Any suitable vector used for expression of recombinant proteins host cells can be used.

Expression vectors typically have an expression cassette that contains all the elements required for the expression of the polynucleotide of choice in a host cell. A typical expression cassette contains a promoter operably linked to the polynucleotide sequence of choice. The promoter used to direct expression of the nucleic acid depends on the particular application, for example, the promoter may be a prokaryotic or eukaryotic promoter depending on the host cell of choice. The promoter is preferably positioned about the same distance from the heterologous transcription start site as it is from the transcription start site in its natural setting. As is known in the art, however, some variation in this distance can be accommodated without loss of promoter function.

Promoters include any promoter suitable for driving the expression of a heterologous gene in a host cell, including those typically used in standard expression cassettes. In addition to the promoter, the recombinant protein gene will be operably linked to appropriate expression control sequences for each host. For *E. coli* this includes a promoter such as the T7, trp, tac, lac or lambda promoters, a ribosome binding site, and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The vectors can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes. One of skill in the art will appreciate that vectors comprising DNA encoding the $V_L$ chain of an antibody and vectors comprising DNA encoding the $V_H$ chain of an antibody can conveniently be separately transfected into different host cells. Alternately vectors comprising DNA encoding the $V_L$ chain of an antibody and vectors comprising DNA encoding the $V_H$ chain of an antibody may be cotransfected into the same host cells.

The wild-type antichelate-antibodies can be expressed in a variety of host cells, including *E. coli*, other bacterial hosts, yeast, and various higher eukaryotic cells such as the COS, CHO, and HeLa cells lines and myeloma cell lines. Methods for refolding single chain polypeptides expressed in bacteria such as *E. coli* have been described, are well-known and are applicable to the wild-type anti-chelate polypeptides. (See, e.g., Buchner et al., *Analytical Biochemistry* 205: 263-270 (1992); Pluckthun, *Biotechnology* 9: 545 (1991); Huse et al., *Science* 246: 1275 (1989) and Ward et al., *Nature* 341: 544 (1989)).

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. Renaturation to an appropriate folded form is typically accomplished by dilution (e.g. 100-fold) of the denatured and reduced protein into refolding buffer.

Once expressed, the recombinant proteins can be purified according to standard procedures of the art, including ammonium sulfate precipitation, affinity columns, colunm chromatography, and the like (see, generally, Scopes, PROTEIN PURIFICATION (1982)). The recombinant proteins can be separated from other proteins on the basis of their size, net surface charge, hydrophobicity, and affinity for ligands. In some embodiments, the recombinant proteins comprise tags that facilitate column purification (e.g., tags comprising at least 2, 3, 4, 6, or 8 histidine residues (SEQ ID NOS:27-29)). Suitable columns include, for example, charge induction chromatography columns (HCICC), thiolphilic columns, ion exchange columns, gel filtration columns, immobilized metal affinity columns (IMAC), immunoaffinity columns, and combinations thereof. It will also be apparent to one of skill in the art that additional processing of the recombinant proteins may be performed. For example, a reactive site on the protein or polypeptide may be treated to deblock the thiol groups using methods known in the art and described in, e.g., Stimmel et al., *J. Biol. Chem.* 275: 30445-30450 (2000). Substantially pure compositions of at least about 90 to 95% homogeneity are preferred, and those of 98 to 99% or more homogeneity are most preferred for pharmaceutical uses. Once purified, partially or to homogeneity as desired, the polypeptides may then be used therapeutically and diagnostically.

In some embodiments, the ECAT reagents further comprise a second binding molecule that is complementary to the first binding molecule. In some embodiments, the second binding molecule is bispecific, i.e., the second binding molecule specifically binds both the first binding molecule and the ECAT reagent or a moiety on the ECAT reagent. The second binding molecule can conveniently be used to immobilize the ECAT-biomolecule adduct on a solid support comprising the first binding molecule. For example, the second binding molecule may be a nucleic acid complementary to a nucleic acid attached to the affinity media. In some cases, the second binding molecule is bispecific, i.e., it comprises a first group that specifically binds to the ECAT reagent or to a moiety attached to the ECAT reagent and a second group that specifically binds the first binding molecule. For example, the ECAT reagent and an unrelated molecule such as biotin. The biotin labeled antibody can be used to immobilize the ECAT-biomolecule adduct on an affinity medium comprising streptavidin.

Another exemplary bispecific binding molecule is a bispecific antibody, i.e., an antibody specific for both the ECAT reagent and the binding molecule on the affinity medium. Bispecific antibodies can be derived from full length antibodies or antibody fragments (e.g. F(ab')$_2$ bispecific antibodies). In some embodiments, the bispecific antibody recognizes a reactive chelate of the invention and an antigen on the surface of a cancer cell. In some embodiments, the bispecific antibody recognizes a DOTA complex (e.g., Y—, La—, Ce—, Pr—, Nd—, Sm—, Eu—, Gd—, Th—, Dy—, Ho—, Er—, Ym—, Yb—, Lu—, Pm—, Ac—, Pa—, Am—, Sc—, Sr—, In—, Ti—, Bi— DOTA), an AABD complex (e.g., Y—, La—, Ce—, Pr—, Nd—, Sm—, Eu—, Gd—, Tb—, Dy—, Ho—, Er—, Ym—, Yb—, Lu—, Pm—, Ac—, Pa—, Am—, Sc—, Sr—, In—, Ti—, Bi— AABD), a BAD complex (e.g., Y—, La—, Ce—, Pr—, Nd—, Sm—, Eu—, Gd—, Tb—, Dy—, Ho—, Er—, Ym—, Yb—, Lu—, Pm—, Ac—, Pa—, Am—, Sc—, Sr—, In—, Ti—, Bi— BAD), an ABD complex (e.g., Y—, La—, Ce—, Pr—, Nd—, Sm—, Eu—, Gd—, Tb—, Dy—, Ho—, Er—, Ym—, Yb—, Lu—, Pm—, Ac—, Pa—, Am—, Sc—, Sr—, In—, Ti—, Bi— ABD), or a NBD complex (e.g., Y—, La—, Ce—, Pr—, Nd—, Sm—, Eu—, Gd—, Tb—, Dy—, Ho—, Er—, Ym—, Yb—, Lu—, Pm—, Ac—, Pa—, Am—, Sc—, Sr—, In—, Ti—, Bi— NBD), including reactive DOTA, AABD, BAD, ABD, NBD, MABD, and FABD complexes and a binding molecule on the affinity media.

Methods for making bispecific antibodies are known in the art. Traditional production of full-length bispecific antibodies is based on the co-expression of two immunoglobulin heavy chain-light chain pairs, where the two chains have different specificities (Millstein and Cuello, *Nature* 305: 537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.* 10: 3655-3659 (1991).

According to one approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. One of skill in the art will appreciate that any immunoglobulin heavy chain known in the art may be fused to an antibody variable domain with the desired binding specificity. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies (see, for example, Suresh et al., *Methods in Enzymology* 121: 210 (1986)).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are discussed herein and disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al. (*Science* 229: 81 (1985)) describe a procedure wherein intact antibodies are proteolytically cleaved to generate F(ab')$_2$ fragments. The fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Ex. Med.*, B 217-225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also, Rodrigues et al., *Int. J. Cancers*, (Suppl.) 7: 45-50 (1992).

Various techniques for making and isolating BsAb fragments directly from recombinant cell culture have also been described. For example, bispecific F(ab')$_2$ heterodimers have been produced using leucine zippers. Kostelny et al., *J. Immunol.*, 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. (USA)*, 90: 6444-6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported (see, Gruber et al., *J. Immunol.*, 152: 5368 (1994)). Gruber et al., designed an antibody which comprised the $V_H$ and $V_L$ domains of a first antibody joined by a 25-amino-acid-residue linker to the $V_H$ and $V_L$ domains of a second antibody. The refolded molecule bound to fluorescein and the T-cell receptor and redirected the lysis of human tumor cells that had fluorescein covalently linked to their surface.

In addition to the preparation of wild-type antibodies that specifically bind to metal chelates, the present invention provides mutant antibodies that include a reactive site within their structure. The mutant antibodies are prepared by any method known in the art, most preferably by site directed mutagenesis of a nucleic acid encoding the wild-type antibody.

The preparation of antibodies that bind to metal chelates is discussed above. The elements of the discussion above are also broadly applicable to aspects and embodiments of the invention in which site directed mutagenesis is used to produce mutant antibodies. The concept of site-directed mutagenesis as it applies to the present invention is discussed in greater detail to supplement, not to replace the discussion above.

The mutant antibodies are suitably prepared by introducing appropriate nucleotide changes into the DNA encoding the polypeptide of interest, or by in vitro synthesis of the desired mutant antibody. Such mutants include, for example, deletions from, or insertions or substitutions of, residues within the amino acid sequence of the polypeptide of interest so that it recognizes the proper epitope and is able to form a covalent bond with a reactive metal chelate. Any combination of deletion, insertion, and substitution is made to arrive at the final construct, provided that the final construct possesses the desired characteristics. The amino acid changes also may alter post-translational processes of the polypeptide of interest, such as changing the number or position of glycosylation sites. Moreover, like most mammalian genes, the antibody can be encoded by multi-exon genes.

For the design of amino acid sequence mutants of the antibodies, the location of the mutation site and the nature of the mutation will be determined by the specific polypeptide of interest being modified and the structure of the reactive chelate to which the antibody binds. The sites for mutation can be modified individually or in series, e.g., by: (1) substituting first with conservative amino acid choices and then with more radical selections depending upon the results achieved; (2) deleting the target residue; or (3) inserting residues of the same or a different class adjacent to the located site, or combinations of options 1-3.

A useful method for identification of certain residues or regions of the polypeptide of interest that are preferred locations for mutagenesis is called "alanine scanning mutagenesis," as described by Cunningham and Wells, *Science*, 244: 1081-1085 (1989). Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the variants produced are screened for increased reactivity with a particular reactive chelate.

Amino acid sequence deletions generally range from about 1 to 30 residues, more preferably about 1 to 10 residues, and typically they are contiguous. Contiguous deletions ordinarily are made in even numbers of residues, but single or odd numbers of deletions are within the scope hereof. As an example, deletions may be introduced into regions of low homology among antibodies which share the most sequence identity to the amino acid sequence of the polypeptide of interest to modify the half-life of the polypeptide. Deletions from the polypeptide of interest in areas of substantial homology with one of the binding sites of other ligands will be more likely to modify the biological activity of the polypeptide of interest more significantly. The number of consecutive deletions will be selected so as to preserve the tertiary structure of the polypeptide of interest in the affected domain, e.g., beta-pleated sheet or alpha helix.

Amino acid sequence insertions include amino- and/or carboxyl-terminal fusions ranging in length from one residue to polypeptides containing a hundred or more residues, as well as intra-sequence insertions of single or multiple amino acid residues. Intra-sequence insertions (i.e., insertions within the mature polypeptide sequence) may range generally from about 1 to 10 residues, more preferably 1 to 5, most preferably 1 to 3. Insertions are preferably made in even numbers of residues, but this is not required. Examples of insertions include insertions to the internal portion of the polypeptide of interest, as well as N- or C-terminal fusions with proteins or peptides containing the desired paratope that will result, upon fusion, in an increased reactivity with the chelate.

A third group of variants are amino acid substitution variants. These variants have at least one amino acid residue in the polypeptide molecule removed and a different residue inserted in its place. The sites of greatest interest for substitutional mutagenesis include one or two loops in antibodies. Other sites of interest are those in which particular residues of the polypeptide obtained from various species are identical among all animal species of the polypeptide of interest, this degree of conservation suggesting importance in achieving biological activity common to these molecules.

These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, such as the exemplary substitutions in Table 1, or as further described below in reference to amino acid classes, are introduced and the products screened.

TABLE 1

| Original | Substitution |
|---|---|
| Ala (A) | val; leu; ile |
| Arg (R) | lys; gln; asn |
| Asn (N) | gln; his; lys |
| Asp (D) | glu |
| Cys (C) | ser |
| Gln (Q) | asn |
| Glu (E) | asp |
| Gly (G) | pro; ala |
| His (H) | asn; gln; lys; arg |
| Ile (I) | leu; vat; met; ala phe; norleucine |
| Leu (L) | norleucine; ile; val; met; ala; phe |
| Lys (K) | arg; gln; asn |
| Met (M) | leu; phe; ile |
| Phe (F) | leu; val; ile; ala; leu |
| Pro (P) | ala |
| Ser (S) | thr |
| Thr (T) | ser |
| Trp (W) | tyr; phe |
| Tyr (Y) | trp; phe; thr; ser |
| Val (V) | ile; leu; met; phe; ala; norleucine |

In addition to the incorporation of the reactive site in the antibody structure, modifications in the function of the polypeptide of interest can be made by selecting substitutions that differ significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions entail exchanging a member of one of these classes for another class. Such substituted residues also may be introduced into the conservative substitution sites or, more preferably, into the remaining (non-conserved) sites.

It also may be desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a residue such as glutamine or a hydrophilic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1-3 residues are inserted adjacent to such sites.

The nucleic acid molecules encoding amino acid sequence mutations of the antibodies of interest are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the polypeptide on which the variant herein is based.

Oligonucleotide-mediated mutagenesis is a preferred method for preparing substitution, deletion, and insertion antibody mutants herein. This technique is well known in the art as described by Ito et al., *Gene* 102: 67-70 (1991) and Adelman et al., *DNA* 2: 183 (1983). Briefly, the DNA is altered by hybridizing an oligonucleotide encoding the desired mutation to a DNA template, where the template is the single-stranded form of a plasmid or bacteriophage containing the unaltered or native DNA sequence of the polypeptide to be varied. After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can be generated by those vectors that are either derived from bacteriophage M13 vectors (e.g., the commercially available M13mp18 and M13mp19 vectors are suitable), or those vectors that contain a single-stranded phage origin of replication as described by Viera et al. *Meth. Enzymol.*, 153: 3 (1987). Thus, the DNA that is to be mutated may be inserted into one of these vectors to generate single-stranded template. Production of the single-stranded template is described in Sections 4.21-4.41 of Sambrook et al., supra. Alternatively, single-stranded DNA template is generated by denaturing double-stranded plasmid (or other) DNA using standard techniques.

Mutations in the $V_H$ and $V_L$ domains may be introduced using a number of methods known in the art. These include site-directed mutagenesis strategies such as overlap extension PCR (see, e.g., Sambrook & Russell, supra; Ausubel et al., supra). Exemplary techniques and primers are provided in Examples 2 and 3.

The PCR products are subcloned into suitable cloning vectors that are well known to those of skill in the art and commercially available. Clones containing the correct size DNA insert are identified, for example, by agarose gel electrophoresis. The nucleotide sequence of the heavy or light chain coding regions is then determined from double stranded plasmid DNA using the sequencing primers adjacent to the cloning site. Commercially available kits (e.g., the Sequenase® kit, United States Biochemical Corp., Cleveland, Ohio) are used to facilitate sequencing the DNA.

One of skill will appreciate that, utilizing the sequence information provided for the variable regions, nucleic acids encoding these sequences are obtained using a number of methods well known to those of skill in the art. Thus, DNA encoding the variable regions is prepared by any suitable method, including, for example, amplification techniques such as ligase chain reaction (LCR) (see, e.g., Wu & Wallace (1989) *Genomics* 4:560, Landegren, et al. (1988) *Science* 241:1077, and Barringer, et al. (1990) *Gene* 89:117), transcription amplification (see, e.g., Kwoh, et al. (1989) *Proc. Natl Acad. Sci. USA* 86:1173), and self-sustained sequence replication (see, e.g., Guatelli, et al. (1990) *Proc. Natl Acad. Sci. USA* 87:1874), cloning and restriction of appropriate sequences or direct chemical synthesis by methods such as the phosphotriester method of Narang, et al., (1979) *Meth. Enzymol.* 68:90; the phosphodiester method of Brown, et al., (1979) *Meth. Enzymol.* 68:109; the diethylphosphoramidite method of Beaucage, et al., (1981) *Tetra. Lett.* 22:1859; and the solid support method of U.S. Pat. No. 4,458,066.

The nucleic acid sequences that encode the single chain antibodies, or variable domains, are identified by techniques well known in the art (see, Sambrook, et al., supra). Briefly, the DNA products described above are separated on an electrophoretic gel. The contents of the gel are transferred to a suitable membrane (e.g., Hybond-N®, Amersham) and hybridized to a suitable probe under stringent conditions. The probe should comprise a nucleic acid sequence of a fragment embedded within the desired sequence.

If the DNA sequence is synthesized chemically, a single stranded oligonucleotide will result. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are later ligated together.

Alternatively, subsequences may be cloned and the appropriate subsequences cleaved using appropriate restriction enzymes. The fragments may then be ligated to produce the desired DNA sequence.

Nucleic acids encoding monoclonal antibodies or variable domains thereof are typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding therapeutic proteins comprise a nucleic acid sequence encoding a therapeutic protein and subsequences, interspecies homologues, alleles and polymorphic variants thereof.

To obtain high level expression of a cloned gene, such as those cDNAs encoding a suitable monoclonal antibody, one typically subclones the gene encoding the monoclonal antibody into an expression vector that contains a strong promoter to direct transcription, a transcription/translation terminator, and if for a nucleic acid encoding a protein, a ribosome binding site for translational initiation. Suitable promoters are well known in the art and described, e.g., in Sambrook et al., supra and Ausubel et al., supra. Eukaryotic expression systems for mammalian cells are well known in the art and are also commercially available. Kits for such expression systems are commercially available.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

The nucleic acid comprises a promoter to facilitate expression of the nucleic acid within a cell. Suitable promoters include strong, eukaryotic promoter such as, for example promoters from cytomegalovirus (CMV), mouse mammary tumor virus (MMTV), Rous sarcoma virus (RSV), and adenovirus. More specifically, suitable promoters include the promoter from the immediate early gene of human CMV (Boshart et al., (1985) *Cell* 41:521) and the promoter from the long terminal repeat (LTR) of RSV (Gorman et al., (1982) *Proc. Natl. Acad. Sci. USA* 79:6777).

For eukaryotic expression, the construct may comprise at a minimum a eukaryotic promoter operably linked to a nucleic acid operably linked to a polyadenylation sequence. The polyadenylation signal sequence may be selected from any of a variety of polyadenylation signal sequences known in the art, such as, for example, the SV40 early polyadenylation signal sequence. The construct may also include one or more introns, which can increase levels of expression of the nucleic acid of interest, particularly where the nucleic acid of interest is a cDNA (e.g., contains no introns of the naturally-occurring sequence). Any of a variety of introns known in the art may be used.

Other components of the construct may include, for example, a marker (e.g., an antibiotic resistance gene (such as an ampicillin resistance gene)) to aid in selection of cells containing and/or expressing the construct, an origin of replication for stable replication of the construct in a bacterial cell (preferably, a high copy number origin of replication), a nuclear localization signal, or other elements which facilitate production of the nucleic acid construct, the protein encoded thereby, or both.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence and signals required for efficient polyadenylation of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes.

Some expression systems have markers that provide gene amplification such as thymidine kinase, hygromycin B phosphotransferase, and dihydrofolate reductase.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical; any of the many resistance genes known in the art are suitable. The prokaryotic sequences are preferably chosen such that they do not interfere with the replication of the DNA in eukaryotic cells.

Standard transfection methods are used to produce bacterial, mammalian, yeast, insect, or plant cell lines that express large quantities of the antibody or variable region domains, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the monoclonal antibody or a variable domain thereof.

After the expression vector is introduced into the cells, the transfected cells are cultured under conditions favoring expression of the polypeptide binding molecule. The expressed protein is recovered from the culture using standard techniques known to those of skill in the art.

The polypeptide binding molecule may be purified to substantial purity by standard techniques known to those of skill in the art, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

1. Covalent Modifications of Binding Molecules

Covalent modifications of binding molecules are included within the scope of this invention. The modifications are made by chemical synthesis or by enzymatic or chemical cleavage or elaboration of the binding molecules (e.g., polypeptide, nucleic acids, lipids, and polysaccharides). For example, covalent modifications can be introduced into a polypeptide binding molecule by reacting targeted amino acid residues of the polypeptide with an organic derivatizing agent that is capable of reacting with selected side chains of internal amino acids or the with N- or C-terminal residues. One of skill in the art will appreciate that modifications can be made that do not interfere with the interaction between the binding molecule and its binding partner.

The modifications of the binding molecules include the attachment of agents to, for example, enhance binding molecule stability, water-solubility, in vitro half-life and to increase the specificity and strength of the bond between the binding molecule and the ECAT reagents or the binding molecule and the affinity resin. Many methods are known in the art for derivatizing both the binding molecules and ECAT reagents. The discussion that follows is illustrative of reactive groups found on the binding molecule and on the ECAT reagent and methods of forming conjugates between the binding molecule and the ECAT reagent. The use of homo- and hetero-bifunctional derivatives of each of the reactive functionalities discussed below to link the binding molecule and the ECAT reagent is within the scope of the present invention.

Cysteinyl residues most commonly are reacted with agents that include α-haloacetates (and corresponding amines), such as chloroacetic acid or chloroacetamide, to give carboxymethyl or carboxyamidomethyl derivatives. Cysteinyl residues also are derivatized by reaction with additional agents known in the art, including, for example, bromotrifluoroketones, α-bromo-β-(5-imidozoyl)carboxylic acids, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with, for example, groups that include pyrocarbonate at pH 5.5-7.0 because this agent is relatively specific for the histidyl side chain. Para-bromophenacyl halides also are useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues are well known in the art and include, for example, imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine site. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azo-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the nitrogen groups of lysine, arginine, and histidine side chains (T. E. Creighton, PROTEINS: STRUCTURE AND MOLECULAR PROPERTIES, W. H. Freeman & Co., San Francisco, pp. 79-86 (1983)), acetylation of the N-terminal amine, and amidation of any C-terminal carboxyl group.

Another type of covalent modification of the polypeptide variant included within the scope of this invention comprises altering the original glycosylation pattern of the polypeptide variant. By altering is meant deleting one or more carbohydrate moieties found in the polypeptide variant, and/or adding one or more glycosylation sites that are not present in the polypeptide variant.

Glycosylation of the binding molecule is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the binding molecule is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide variant (for O-linked glycosylation sites). For ease, a polypeptide sequence is preferably altered through changes at the DNA level, particularly by mutating the DNA encoding the polypeptide at preselected bases such that codons are generated that will translate into the desired amino acids. The DNA mutation(s) may be made using methods described above.

Another means of increasing the number of carbohydrate moieties on the binding molecule is by chemical or enzymatic coupling of glycosides to a polypeptide. These procedures are advantageous in that they do not require production of the polypeptide variant in a host cell that has glycosylation capabilities for N- or O-linked glycosylation. Depending on the coupling mode used, the sugar(s) may be attached to (a) arginine, histidine, and lysine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston, CRC CRIT. REV. BIOCHEM., pp. 259-306 (1981).

Removal of any carbohydrate moieties present on the binding molecule is accomplished either chemically or enzymatically. Chemical deglycosylation requires exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the mutant antibody intact. Chemical deglycosylation is described by Hakimuddin et al., *Arch. Biochem. Biophys*. 259: 52 (1987) and by Edge et al., *Anal. Biochem*. 118: 131 (1981). Enzymatic cleavage of carbohydrate moieties on polypeptides can be achieved by the use of a variety of endo- and exo-glycosidases as described by Thotakura et al., *Meth. Enzymol*. 138: 350 (1987).

Another type of covalent modification of polypeptides comprises linking the polypeptide variant to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337. The polymers are added to alter the properties of the binding molecule or, alternatively, they serve as spacer groups between the targeting agent and the mutant antibody.

2. Preparation of the Binding Molecule-Affinity Media Conjugate

The binding molecules can be immobilized to a solid support via a reactive group that is present in the binding molecule or one that is engineered into the binding molecule. Generally, it is preferable to form a conjugate between the binding molecule and the solid support in a manner that does not compromise the activity or selectivity of the binding molecule. In some embodiments, the binding molecule is a polypeptide such as an antibody. In some embodiments, the antibody is 2D12.5

Methods of derivatizing nucleic acids, polypeptides (e.g., via the ϵ-amine of lysine), lipids, and polysaccharides are well known in the art and are described in, e.g., Hermanson, *Bioconjugate Techniques* (1996).

An exemplary strategy involves incorporation of a protected sulfhydryl onto an antibody using the heterobifunctional crosslinker SPDP (N-succinimidyl-3-(2-pyridyldithio)propionate and then deprotecting the sulfhydryl for formation of a disulfide bond with another sulfhydryl on the solid support. Instead of destabilizing the antibody with reducing agents to generate free sulfhydryls, new sulfhydryls are optionally incorporated onto the antibody using SPDP. In the protected form, the SPDP generated sulfhydryls on the antibody react with the free sulfhydryls incorporated onto the solid support forming a disulfide bond. By optimizing reaction conditions, the degree of SPDP modification of the antibody is controlled, thus maintaining maximum activity of the antibody. SPDP reacts with primary amines and the incorporated sulfhydryl is protected by 2-pyridylthione.

If SPDP should affect the activities of the binding molecule, there are a number of additional crosslinkers such as 2-iminothiolane or N-succinimidyl S-acetylthioacetate (SATA), available for forming disulfide bonds. 2-iminothiolane reacts with primary amines, instantly incorporating an unprotected sulfhydryl onto the protein. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary and not limiting of linkers of use in the invention. Other crosslinkers are available that can be used in different strategies for crosslinking the binding molecule to the solid support. For example, TPCH(S-(2-thiopyridyl)-L-cysteine hydrazide and TPMPH ((S-(2-thiopyridyl) mercapto-propionohydrazide) react at the carbohydrate moieties of glycoproteins that have been previously oxidized by mild periodate treatment, thus forming a hydrazone bond between the hydrazide portion of the crosslinker and the periodate generated aldehydes. The placement of this crosslinker on the antibody is beneficial since the modification is site-specific and will not interfere with the antigen-binding site of the antibody. TPCH and TPMPH introduce a 2-pyridylthione protected sulfhydryl group onto the antibody, which can be deprotected with DTT and then subsequently used for conjugation, such as forming disulfide bonds between components.

If disulfide bonding is found unsuitable for producing stable conjugates, other crosslinkers may be used that incorporate more stable bonds between components. The heterobifunctional crosslinkers GMBS (N-gamma-maleimidobutyryloxy)succinimide) and SMCC (succinimidyl 4-(N-maleimido-methyl)cyclohexane) react with primary amines, thus introducing a maleimide group onto the component. This maleimide group can subsequently react with sulfhydryls on the other component, which can be introduced by previously mentioned crosslinkers, thus forming a stable thioether bond between the components. If steric hindrance between components interferes with either component's activity, crosslinkers can be used which introduce long spacer arms between components and include derivatives of some of the previously mentioned crosslinkers (i.e., SPDP). Thus there is an abundance of suitable crosslinkers, which are useful; each of which is selected depending on the effects it has on optimal immunoconjugate production.

A variety of reagents are of use to bind the binding molecule to the solid phase. (See, Wold, F., *Meth. Enzymol.* 25: 623-651, 1972; Weetall, H. H., and Cooney, D. A., In: ENZYMES AS DRUGS. (J. S. Holcenberg, and J. Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Useful crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carbonyl (e.g., an aldehyde) and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

3. Preferred Specific Sites in Crosslinking Reagents a) Amino-Reactive Groups

In one preferred embodiment, the linker arm is formed from a reagent that includes an amino-reactive group. Useful non-limiting examples of amino-reactive groups include N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of the affinity component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with amine groups. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with α-amino groups and lysine ε-amino groups to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of mono- and dicarboxylic acids are also useful amino-reactive groups. Although the reagent specificity is not very high, α- and ε-amino groups appear to react most rapidly.

Aldehydes such as glutaraldehyde react with primary amines (e.g., ε-amino group of lysine residues). Glutaraldehyde, however, displays reactivity with several other amino acid side chains including those of cysteine, histidine, and tyrosine. Since dilute glutaraldehyde solutions contain monomeric and a large number of polymeric forms (cyclic hemiacetal) of glutaraldehyde, the distance between two crosslinked groups within the affinity component varies. Although unstable Schiff bases are formed upon reaction of the protein amino groups with the aldehydes of the polymer, glutaraldehyde is capable of modifying the affinity component with stable crosslinks. At pH 6-8, the pH of typical crosslinking conditions, the cyclic polymers undergo a dehydration to form α-β unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites, but reaction with the amino groups is the most important, resulting in a stable sulfonamide linkage.

b) Sulfhydryl-Reactive Groups

In another preferred embodiment, the linker arm is formed from a reagent that includes a sulfhydryl-reactive group. Useful non-limiting examples of sulfhydryl-reactive groups include maleimides, alkyl halides, pyridyl disulfides, and thiophthalimides.

Maleimides react preferentially with sulfhydryl groups to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form also disulfides.

c) Guanidino-Reactive Groups

In another embodiment, the linker arm is formed from a reagent that includes a guanidino-reactive group. A useful non-limiting example of a guanidino-reactive group is phenylglyoxal. Phenylglyoxal reacts primarily with the guanidino groups of arginine residues in the affinity component. Histidine and cysteine also react, but to a much lesser extent.

d) Indole-Reactive Groups

In another embodiment, the sites are indole-reactive groups. Useful non-limiting examples of indole-reactive groups are sulfenyl halides. Sulfenyl halides react with tryptophan and cysteine, producing a thioester and a disulfide, respectively. To a minor extent, methionine may undergo oxidation in the presence of sulfenyl chloride.

e) Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage (See e.g., Yamada et al., *Biochemistry* 20: 4836-4842 (1981) which teaches how to modify a protein with carbodiimde.

4. Preferred Nonspecific Sites in Crosslinking Reagents

In addition to the use of site-specific reactive moieties, the present invention contemplates the use of non-specific reactive groups to link the mutant antibody to the solid support. Non-specific groups include photoactivatable groups, for example. In another preferred embodiment, the sites are photoactivatable groups. Photoactivatable groups, completely inert in the dark, are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, C=C, and —S—H. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al, *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

5. Homobifunctional Reagents a) Homobifunctional Crosslinkers Reactive with Primary Amines Synthesis, properties, and applications of homobifunctional amine-reactive reagents are described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxycarbonyloxy)ethylsulfone (sulfo-BSOCOES), ethylene glycol-bis(succinimidylsuccinate) (EGS), ethylene glycolbis (sulfosuccinimidylsuccinate) (sulfo-EGS), dithiobis (succinimidylpropionate) (DSP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-,3'-(dimethylenedioxy)dipropionimidate (DDDP), dimethyl-3,3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride. Preferred, non-limiting examples of additional amino-reactive homobifunctional reagents include erythritolbiscarbonate which reacts with amines to give biscarbamates.

b) Homobifunctional Crosslinkers Reactive with Free Sulfhydryl Groups

Synthesis, properties, and applications of sulfhydryl-reactive reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene) bismaleimide, N,N'-(1,2-phenylene)bismaleimide, azophenyldimaleimide, and bis(N-maleimidomethyl) ether. Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene,α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di(bromoacetyl)amino-3-phenylpropane.

c) Homobifunctional Photoactivatable Crosslinkers

Synthesis, properties, and applications of photoactivatable reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-b-(4-azidosalicylamido)ethyldisulfide (BASED), di-N-(2-nitro-4-azidophenyl)-cystamine-S,S-dioxide (DNCO), and 4,4'-dithiobisphenylazide.

6. Hetero-Bifunctional Reagents a) Amino-Reactive Hetero-Bifunctional Reagents with a Pyridyl Disulfide Moiety Synthesis, properties, and applications of heterobifunctional sulfhydryl-reactive reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio)propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio)toluene (SMPT), and sulfosuccinimidyl 6-α-methyl-α-(2-pyridyldithio)toluamidohexanoate (sulfo-LC-SMPT).

b) Amino-Reactive Hetero-Bifunctional Reagents with a Maleimide Moiety

Synthesis, properties, and applications of heterobifunctional amine/sulfhydryl-reactive reagents are described in the literature. Preferred, non-limiting examples of heterobifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidylhexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

c) Amino-Reactive Hetero-Bifunctional Reagents with an Alkyl Halide Moiety

Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino) hexanoylamino)hexanoate (SIAXX), succinimidyl-6-(((4-(iodoacetyl)-amino)-methyl)-cyclohexane-1-carbonyl) aminohexanoate (SIACX), and succinimidyl-4 ((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl-2,3-dibromopropionate (SDBP). SDBP introduces intramolecular crosslinks to the affinity component by conjugating its amino groups. The reactivity of the dibromopropionyl moiety for primary amino groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

7. Photoactivatable Arylazide-Containing Hetero-Bifunctional Reagents with a NHS Ester Moiety Preferred, non-limiting examples of photoactivatable arylazide-containing heterobifunctional reagents with an amino-reactive NHS ester include N-hydroxysuccinimidyl-4-azidosalicylic acid (NHS-ASA), N-hydroxysulfosuccinimidyl-4-azidosalicylic acid (sulfo-NHS-ASA), sulfosuccinimidyl-(4-azidosalicylamido)hexanoate (sulfo-NHS-LC-ASA), N-hydroxysuccinimidyl N-(4-azidosalicyl)-6-aminocaproic acid (NHS-ASC), N-hydroxysuccinimidyl-4-azidobenzoate (HSAB), N-hydroxysulfo-succinimidyl-4-azidobenzoate (sulfo-HSAB), sulfosuccinimidyl-4-(p-azidophenyl)butyrate (sulfo-SAPB), N-5-azido-2-nitrobenzoyloxy-succinimide (ANB-NOS), N-succinimidyl-6-(4'-azido-2'-nitrophenylamino)hexanoate (SANPAH), sulfosuccinimidyl-6-(4'-azido-2'-nitrophenylamino)-hexanoate (sulfo-SANPAH), N-succinimidyl 2-(4-azidophenyl)dithioacetic acid (NHS-APDA), N-succinimidyl-(4-azidophenyl)1,3'-dithiopropionate (SADP), sulfosuccinimidyl-(4-azidophenyl)-1,3'-dithiopropionate (sulfo-SADP), sulfosuccinimidyl-2-(m-azido-o-nitrobenzamido)ethyl-1,3'-dithiopropionate (SAND), sulfosuccinimidyl-2-(p-azidosalicylamido)-ethyl-1,3'-dithiopropionate (SASD), N-hydroxysuccinimidyl 4-azidobenzoylglycyltyrosine (NHS-ABGT), sulfosuccinimidyl-2-(7-azido-4-4-methylcoumarin-3-acetamide)ethyl-1,3'-dithiopropionate (SAED), and sulfosuccinimidyl-7-azido-4-methylcoumarin-3-acetate (sulfo-SAMCA).

Other cross-linking agents are known to those of skill in the art (see, for example, Pomato et al., U.S. Pat. No. 5,965,106).

8. Linker Groups

In addition to the embodiments set forth above, wherein the cross-linking moiety is attached directly to a site on the binding molecule and on the solid support, the present invention also provides constructs in which the cross-linking moiety is bound to a site present on a linker group that is bound to either the binding molecule or the solid support or both. In certain embodiments, it is advantageous to tether the antibody to the solid support by a group that provides flexibility and increases the distance between the mutant antibody and the targeting moiety. Using linker groups, the properties of the oligonucleotide adjacent to the stabilizing moiety can be modulated. Properties that are usefully controlled include, for example, hydrophobicity, hydrophilicity, surface-activity and the distance of the antibody from the chromatographic support.

In an exemplary embodiment, the linker serves to distance the binding molecule from the solid support. Linkers with this characteristic have several uses. For example, a binding molecule (e.g., an polypeptide such as an antibody) held too closely to the support may not effectively interact with its binding partner, e.g., the binding molecule and binding partner may interact with too low an affinity. Thus, it is within the scope of the present invention to utilize linker moieties to, inter alia, vary the distance between the binding molecule and the chromatographic support.

In yet a further embodiment, the linker group is provided with a group that can be cleaved to release the binding molecule from the support. Many cleavable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover, a broad range of cleavable, bifunctional (both homo- and hetero-bifunctional) linker groups are commercially available from suppliers such as Pierce.

Exemplary cleavable moieties are cleaved using light, heat or reagents such as thiols, hydroxylamine, bases, periodate and the like. Exemplary cleavable groups comprise a cleavable moiety which is a member selected from the group consisting of disulfide, ester, imide, carbonate, nitrobenzyl, phenacyl, benzoin, and vicinal diol groups.

V. Detection of Adducts

The ECAT-biomolecule adducts can be analyzed using any means known in the art to detect, quantify, and characterize (i.e., detect oxidized sites) the oxidized biomolecules present in a sample. In some embodiments, the adducts are analyzed using mass spectrometry, e.g., electrospray ionization (ESI) MS/MS; matrix assisted laser desorption/ionization (MALDI); or Fourier-transform ion cyclotron resonance (FT-ICR) mass spectrometry. Biomolecules originating from different sources can be distinguished based on the mass difference of particular metal ion present in the ECAT. Multiple adducts can be analyzed sequentially or simultaneously, e.g., by tandem mass spectrometry ($MS^n$). In some embodiment, the adducts are analyzed in a multiplex format.

After analysis by mass spectrometry, the ratio of the ion intensities for a labeled pair of biomolecule fragments provides the relative abundance of the parent biomolecule in the original populations. In addition, through techniques well known in the art, the biomolecules may be further analyzed to determine their sequence. For example, tandem mass spectrometry MS/MS may be performed on peptides, followed by database searches to match fragmentation patterns and identify the peptide in question.

Using a plurality of distinguishable versions of an ECAT reagent allows the simultaneous analysis of additional samples. For example, the use of chelates of Y, La, Pr, Tb and Dy of a ECAT reagent described above would allow a control sample to be directly compared to four experimental samples at the same time. Thus, the reagents of the present invention provide a powerful tool for rapidly quantitatively analyzing biomolecule expression and can function as a complementary method to study gene expression and perturbation induced changes.

In certain preferred embodiments, the ECAT reagents of the present invention react specifically with selected amino acid residues. Because of the specificity of the reagents for particular protein structures (e.g., amino acid side chain), the method can be used to distinguish between functionally different but isobaric species. For example, the post-translational modification of arginine to a modified form may be difficult to detect by routine mass spectrometry. However, if the post-translational modification removed or significantly altered the guanidine group, certain arginine reactive moieties of the invention would preferably react with arginine and not the post-translationally modified form. The relative amounts of such species could be determined by selectively targeting the native and post-translationally modified amino acids with different ECATs.

In certain embodiments of the present invention, it is advantageous to separate the biomolecules in a sample into fractions before or after tagging and detection. This can be accomplished by a wide variety of methods familiar to those skilled in the art. The separation or fractionation, analysis and identification of tagged or untagged biomolecules (e.g., polypeptides, nucleic acids, lipids, and polysaccharides) can be accomplished using any means known in the art, including, e.g., 2-D gel electrophoresis, capillary electrophoresis, micro-channel electrophoresis, HPLC, FPLC, size exclusion chromatography, filtration, polyacrylamide gel electrophoresis (PAGE) (e.g., including PAGE followed by Western blotting), liquid chromatography, reverse size exclusion chromatography, ion-exchange (i.e., cation or anion) chromatography, reverse phase liquid chromatography, pulsed-field electrophoresis, field-inversion electrophoresis, dialysis, and fluorescence-activated liquid droplet sorting. Alternatively, the proteins or peptides may be bound to a solid support (e.g., hollow fibers (Amicon Corporation, Danvers, Mass.), beads (Polysciences, Warrington, Pa.), magnetic beads (Robbin Scientific, Mountain View, Calif.), plates, dishes and flasks (Corning Glass Works, Coming, N.Y.), meshes (Becton Dickinson, Mountain View, Calif.), screens and solid fibers (see Edelman et al., U.S. Pat. No. 3,843,324; see also Kuroda et al., U.S. Pat. No. 4,416,777), membranes (Millipore Corp., Bedford, Mass.), and dipsticks. If the biomolecules are bound to a solid support, within certain embodiments of the invention the methods disclosed herein may further comprise the step of washing the solid support.

In some embodiments it may be desirable to cleave or "digest" the biomolecules in a sample, either before or after tagging. For example, biomolecules may be enzymatically or chemically digested using methods known in the art. In an exemplary embodiment, proteins in the sample may be digested with cyanogen bromide (CNBr) or enzymatically digested (e.g., with trypsin) either before or after being labeled. In another exemplary embodiment, nucleic acids may be cleaved by mechanical shearing, digested with piperidine, or digested with a restriction enzyme.

The ECAT-tagged species can also be analyzed using a wide range of mass spectrometric techniques. Representative examples of suitable spectrometric techniques include time-of-flight (TOF) mass spectrometry, quadrupole mass spectrometry, magnetic sector mass spectrometry and electric sector mass spectrometry. Specific embodiments of such techniques include ion-trap mass spectrometry, electrospray ionization (ESI) mass spectrometry, ion-spray mass spectrometry, liquid ionization mass spectrometry, atmospheric pressure ionization mass spectrometry, electron ionization mass spectrometry, fast atom bombard ionization mass spectrometry, MALDI mass spectrometry, photo-ionization time-of-flight mass spectrometry, laser droplet mass spectrometry, MALDI-TOF mass spectrometry, APCI mass spectrometry, nano-spray mass spectrometry, nebulised spray ionization mass spectrometry, chemical ionization mass spectrometry, resonance ionization mass spectrometry, secondary ionization mass spectrometry and thermospray mass spectrometry.

VI. Kits

In yet another aspect, the invention provides kits for detecting biomolecules (e.g., oxidized biomolecules), identifying oxidation sites on biomolecules, and comparing levels of a biomolecule (e.g., a polypeptide, a nucleic acid, a lipid, or a polysaccharide) between samples. The kit typically includes at least a first metal ion and a second metal ion as well as a chelating agent as described herein. The chelating agents typically comprise the structure set forth in Formula, I, Ia, Ia', Ia", as described above, or a combination thereof. In some embodiments, the chelating agent is a member selected from substituted or unsubstituted DOTA and substituted or unsubstituted TETA. In some embodiments, the kits further comprise an affinity medium as described herein. The kits may optionally include instructions for use.

The invention is further described in the examples that follow.

EXAMPLES

Example 1 sets forth the use of rational computer-aided design to develop mutants of the monoclonal antibody 2D12.5. Example 2 describes construction of chimeric constructs comprising the variable domain of 2D12.5 and human antibody specific for tetanus toxoid. Example 3 demonstrates that the monoclonal antibody 2D12.5 has broad specificity and high affinity for all rare earth metal DOTA complexes. Example 4 describes affinity purification of metal-DOTA tagged peptides on a 2D12.5 aminolink gel affinity column. Example 5 describes use of ECAT tags to identify the amino acid that participates in the formation of a permanent bond between G54C Fab and AABD. Example 6 describes affinity purification of metal-DITC tagged peptides on a 2D12.5 affinity column. Example 7 describes detection of mutltiple oxidized sites on human serum albumin using (((S)-2-(4-(2-aminooxy)-acetamido)-benzyl)-1,4,7,10-tetraazacyclododecane-N,N',N"N'"-tetraacetic acid (AODOTA), loaded with monoisotopic rare earths.

Example 1

This Example sets forth the use of rational computer-aided design to develop mutants of the monoclonal antibody 2D12.5.

Evaluation of the crystal structure of 2D12.5 bound to its hapten, Y-DOTA in conjunction with molecular modeling software (InsightII, Biosym/MSI) identified two specific side-arm orientations of the chelate in the binding pocket. This observation led to the design and engineering of four separate cysteine mutants (three heavy chain and one light chain). Specifically, cysteine residues were substituted at positions 53, 54, and 55 (positions 54, 55, and 56 if the Kabat standard numbering system is used) of the heavy chain variable domain and position 53 (position 54 if the Kabat standard numbering system is used) of the light chain variable domain. These mutants can conveniently be used in experiments to evaluate the ability of the mutants to irreversible bind suitably derived electrophilic chelates. Additional mutants can conveniently be generated based on the evaluation of the crystal structure of 2D12.5 bound to its hapten.

Example 2

The following example describes the methodology used to prepare chimeric heavy and light chain Fab genes for expression in *Drosophila* Schneider (S2) cells. In all, six different chimeric heavy chain constructs were prepared. The first was the native heavy chain that was composed of the 2D12.5 mAb's variable domain fused with the CH1 of a human anti-tetanus toxoid antibody. The native variable domain contained a N-linked glycosylation site at position 87. This glycocsylation site was removed by engineering a N87D mutant (FR$^3$). This N87D mutant was the "native" heavy chain that was used to construct the three heavy chain cysteine mutants: G53C, G54C and G55C, which are all part of CDR2. The native chimeric light chain and only cysteine mutant (N53C) were also constructed. The N53C mutation is located on CDR2 of the light chain.

As explained above, after inspection of the crystal structure we chose to introduce cysteine residues at positions 53, 54, and 55 (positions 54, 55, and 56 if the Kabat standard numbering system is used) of the heavy chain variable domain and position 53 (position 54 if the Kabat standard numbering system is used) of the light chain variable domain.

2D12.5 hybridoma cells were grown in RPMI 1640 supplemented with 10% FCS and used as a source of genetic template. Poly A mRNA was extracted using methods known to those skilled in the art. Complementary DNA synthesis and PCR amplification of the variable domain genes was accomplished using Novagen's Mouse Ig-Primer kit which incorporates degenerate 3' constant domain primers specific to mouse IgG genes. Double stranded DNA was obtained from cDNA using degenerate 5' and 3' primers provided in the Mouse Ig-Primer kit. The heavy and light chain variable genes, each with an unpaired 3' terminal A, were cloned separately into a pT7Blue T-vector and sequenced. The variable domains were then used to prepare expression constructs.

Chimeric constructs of the murine 2D12.5 variable (light and heavy) domains and human anti-tetanus toxoid antibody CL and CH1 domains were assembled by two-step overlap extension (see, e.g., Pont-Kingdon, *Biotechniques* 16:1010-1011 (1994) and erratum 18:636 (1995)). A BglII restriction site was introduced onto the 5' end of heavy and light chain genes and a XbaI restriction site was introduced onto the 3' end of the tetanus toxin CH1 chain or $C_L\kappa$ chain during overlap extension, and were used to introduce each chimeric gene construct into the pMT/Bip/V5/His plasmid cassette for propagation in *E. coli* and expression in *Drosophila* S2 cells. Heavy and light chain genes were placed into separate plasmids. Site directed substitution of aspartic acid at position 87 (N87D) of the heavy chain was accomplished as described in Ito et al., *Gene* 102: 67-70 (1991). Site directed substitution of cysteine at positions 53 (G53C), 54 (G54C), and 55 (G55SC) of the heavy chain and position 53 (N53C) of the light chain was also accomplished as described in Ito et al., 1991, supra. Mutations were prepared using MT and BGH sequencing primers as well as a BglII primer, and site-specific mutation primers. Four primers and two PCR steps are used to install a mutation in a gene by this method. The primers for site-directed substitution at positions 87 (N87D), 53 (G53C), 54 (G54C), and 55 (G55C) of the heavy chain were as follows: 5' primer (catctcagtg caactaaa; SEQ ID NO:33) (MTforward) for all positions and 3' primer (catggctgtg tcatcagctt gcagactgtt c; SEQ ID NO:34) (N87D), 3' primer (cgtgcctcca caactccata tcac; SEQ ID NO:35) (G53C), 3' primer (ccgtgccaca accactccat atc; SEQ ID NO:36) (G54C), and 3' primer (ccgtgcatcc accactccat atc; SEQ ID NO:37) (G55C). A second PCR reaction to introduce a BglII site into the sequence used the following primers: 5' primer (gctcgggaga tgtgtgaagc tg; SEQ ID NO:42) and 3' primer (tagaaggcac agtcgagg; SEQ ID NO:43) (BGH reverse). The amplified products were combined, extended and amplified with 5' primer (catctcagtg caactaaa: SEQ ID NO:33) (MTforward) and 3' primer (tagaaggcac agtcgagg; SEQ ID NO:43) (BGH reverse).

Primers for site-directed substitution at position 53 (N53C) of the light chain were as follows:5' primer (gaagatctgc tgttgtgact caggaatct: SEQ ID NO:38) (2dVl5'Bgl); 3' primer (agatggtgca gccacagttc ggcttaggac agtcagtttg gt; SEQ ID NO:39) and 5' primer (accaaactga ctgtcctaag ccgaactgtg gctgcaccat ct; SEQ ID NO:40); 3' primer (cgatctagaa ttaacactct cccctg; SEQ ID NO:41) (TTCL3). The amplified products were combined, extended and amplified with 5' primer (gaagatctgc tgttgtgact caggaatct; SEQ ID NO:38) (2dVl5'Bgl) and 3' primer (cgatctagaa ttaacactct cccct; SEQ ID NO:41) (TTCL3) to generate an initial chimeric light chain construct. To eliminate an unwanted G48S mutation in the VL domain and to introduce the N53C mutation, the following primers were used to amplify the initial chimeric light chain construct: 5' primer (catctcagtg caactaaa; SEQ ID NO:33) (MTforward) and 3' primer (cggttattac aaccacctat tagaccagtg aataaatg; SEQ ID NO:44) and 5' primer (gctcgggaga tgtgctgttg tg; SEQ ID NO:45) and 3' primer (tagaaggcac agtcgagg; SEQ ID NO:43) (BGH reverse). The amplification products were combined, extended and the second chimeric light chain construct was amplified using the following primers: 5' primer (catctcagtg caactaaa; SEQ ID NO:33) (MTforward) and 3' primer (tagaaggcac agtcgagg; SEQ ID NO:43) (BGH reverse).

Heavy and light chain containing plasmids were cotransfected into *Drosophila* S2 cells using precipitating calcium phosphate. Cells were induced using 500 μM $CuSO_4$. Stable cell lines were produced by cotransfecting a plasmid containing the hygromycin B phosphotransferase gene along with heavy and light chain DNA. Selection proceeded for 3-4 weeks post-transfection with 300 μg/mL hygromycin B.

Each of the heavy chains were cotransfected with the native light chain in *Drosophila* S2 cells. Also, the N87D heavy chain was cotransfected with the N53C light chain. Stably transfected *Drosophila* S2 cells were induced (native as well as 4 cysteine mutants), and the media was assayed for gene expression by denaturing, nonreducing SDS gel separation followed by Western Blot analysis. Goat anti-human-κ and anti-V5 epitope antibodies (alkaline phosphatase (AP) conjugates) were used to detect for light and heavy chains, respectively. It is clear from the blots that there is heterogeneous glycosylation of the heavy chain. The glycoprotein bands are not present in heavy chains incorporating the N87D mutation, yielding a homogeneous product that is preferable for future applications.

Figure 12:
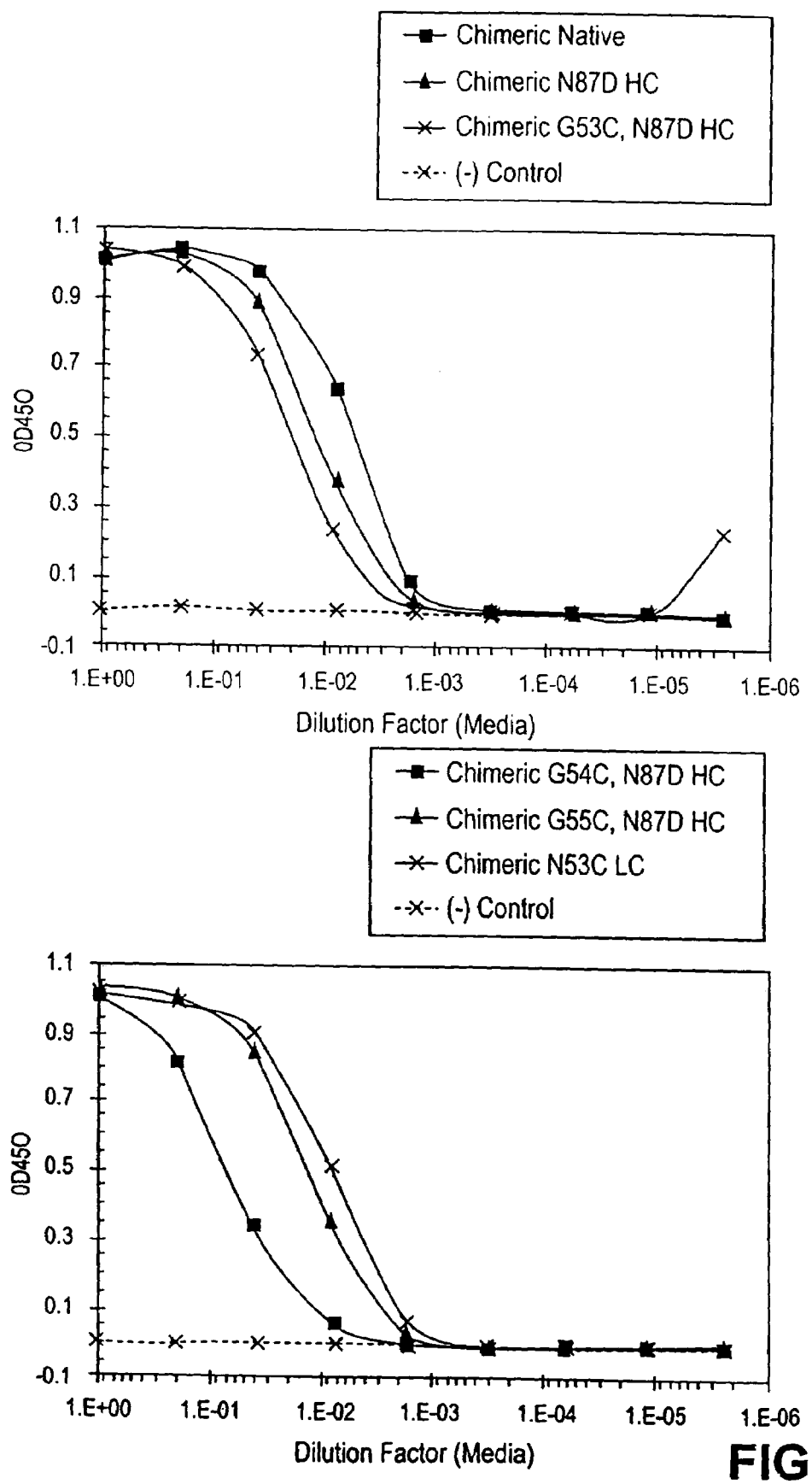
FIG. 12 is a graphical display showing binding of stably transfected *Drosophila* S2 cells expressing the chimeric 2D12.5 Fab gene products (native and site-directed cysteine mutants) to Y-DOTA. Binding curves were determined from non-competitive ELISA assays incorporating dilutions of media containing expressed gene products. The relative amount of expressed chimeric Fab were measured using anti-V5 epitope-HRP conjugate and a visible TMB (3,3',5, 5'-tetramethyl benzidine) substrate.

Stably transfected *Drosophila* S2 cells expressing the chimeric 2D12.5 Fab gene products (native and site-directed cysteine mutants) were evaluated for their ability to bind Y-DOTA. Binding curves were determined from non-competitive ELISA assays incorporating dilutions of media containing expressed gene products. The relative amount of expressed chimeric Fab were measured using anti-V5 epitope-HRP conjugate and a visible TMB (3,3',5,5'-tetramethyl benzidine) substrate. The results are shown in FIG. 12

Example 3

To determine the metal selectivity of the antibody 2D12.5, a competitive immunoassay was used to measure the binding constants of multiple metal-DOTA complexes relative to $Y^{3+}$-DOTA.

Figure 13:
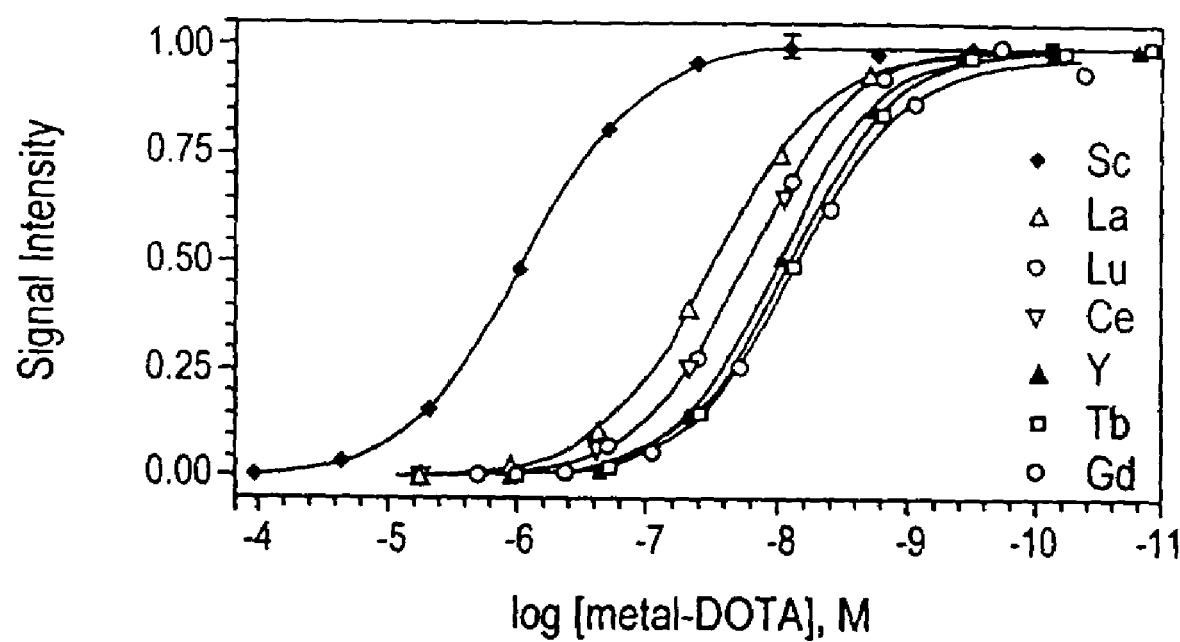
FIG. 13 is graphical display showing the relative binding of metal-DOTA complexes to antibody 2D12.5. A representative set of competitive binding curves obtained from ELISA experiments described in Example 3 below. Error bars (representing the standard error of the mean) are shown, but are generally smaller than the data points.

We examined the monoclonal antibody 2D12.5, initially developed to bind specifically to Y-DOTA for targeted radiotherapy (see, e.g., Goodwin et al., *Cancer Res.* 54: 5937-5946 (1994)), in order to determine the scope of its activity. To assess the metal selectivity of antibody 2D12.5, a competitive immunoassay to measure the binding constants of various metal-DOTA complexes relative to the original $Y^{3+}$ complex was developed (FIG. 13). Briefly, 2D12.5 was incubated at 37° C. in the presence of immobilized Y-DOTA and a soluble metal-DOTA competitor. The metal-DOTA concentration was varied from μM to pM in order to determine the relative binding affinity of 2D12.5 for each metal chelate in comparison to Y-DOTA. Binding was measured by standard methods known to those of skill in the art. The DOTA analog used to evaluate binding was [S]-2-(p-nitrobenzyl)-DOTA, which is similar to the original antigen.

We found that 2D12.5 binds not only Y-DOTA but also DOTA complexes of all the lanthanides. Surprisingly, some metal chelates such as Gd-DOTA bind more tightly than the original $Y^{3+}$ complex; overall, the dissociation constants fall within a factor of 3 above or below the Kd=10 nM value for Y-DOTA. Other antibodies that bind metal chelates do so with a strong preference for one or possibly two metals (see, e.g., Love et al., *Biochemistry* 32: 10950-10959 (1993) and Khosraviani et al., *Bioconjugate Chem.* 11: 267-277 (2000)).

Figure 14:
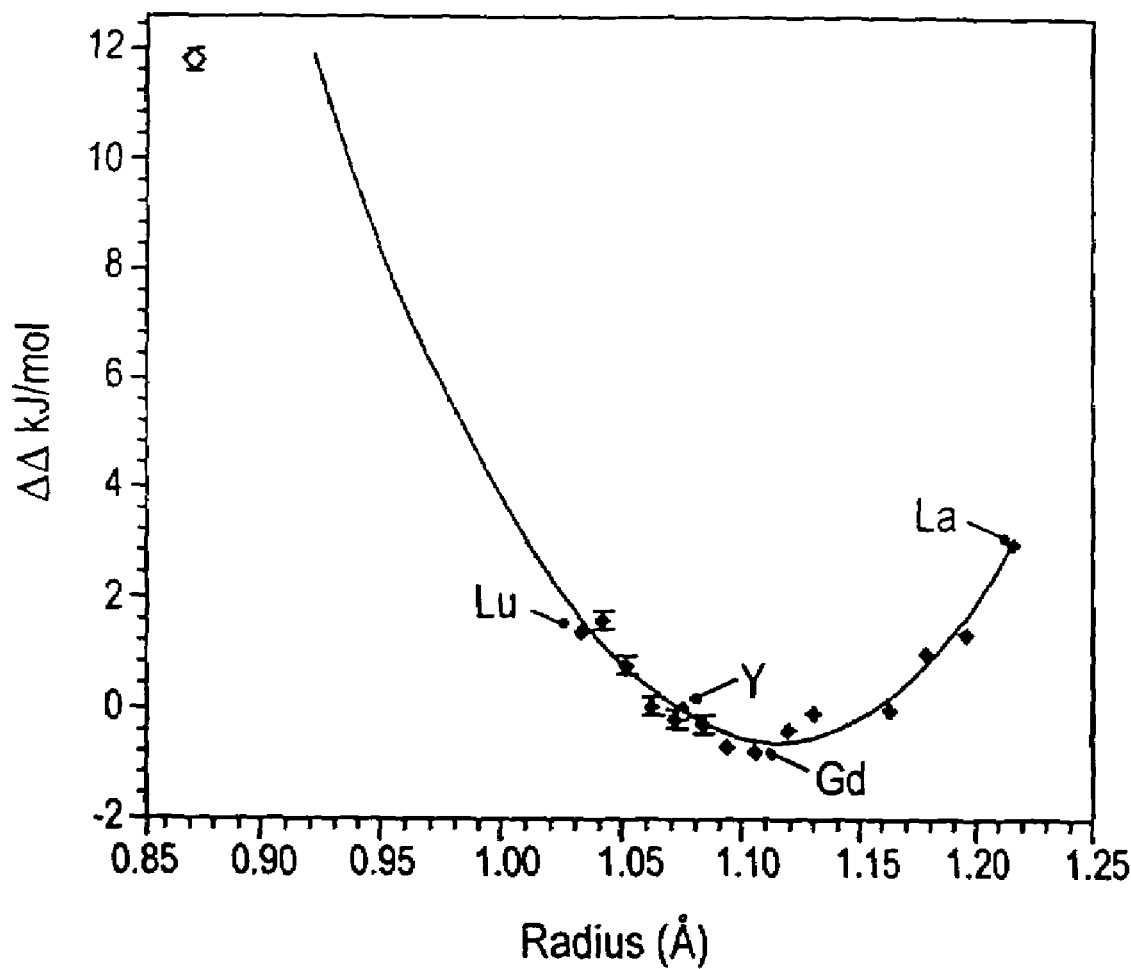
FIG. 14 is a graphical display showing the dependence of the standard Gibbs Free Energy of binding on rare earth ionic radius shows thermodynamically elastic binding behavior between antibody 2D12.5 and rare earth-DOTA complexes. Elements plotted in the order Sc (open circle), Lu, Yb, Tm, Er, Ho, Y (open diamond), Dy, Th, Gd, Eu, Sm, Nd, Pr, Ce, La. ΔΔG values relative to Y-DOTA, set at 0. Error bars represent standard error of the mean.
Figure 15:
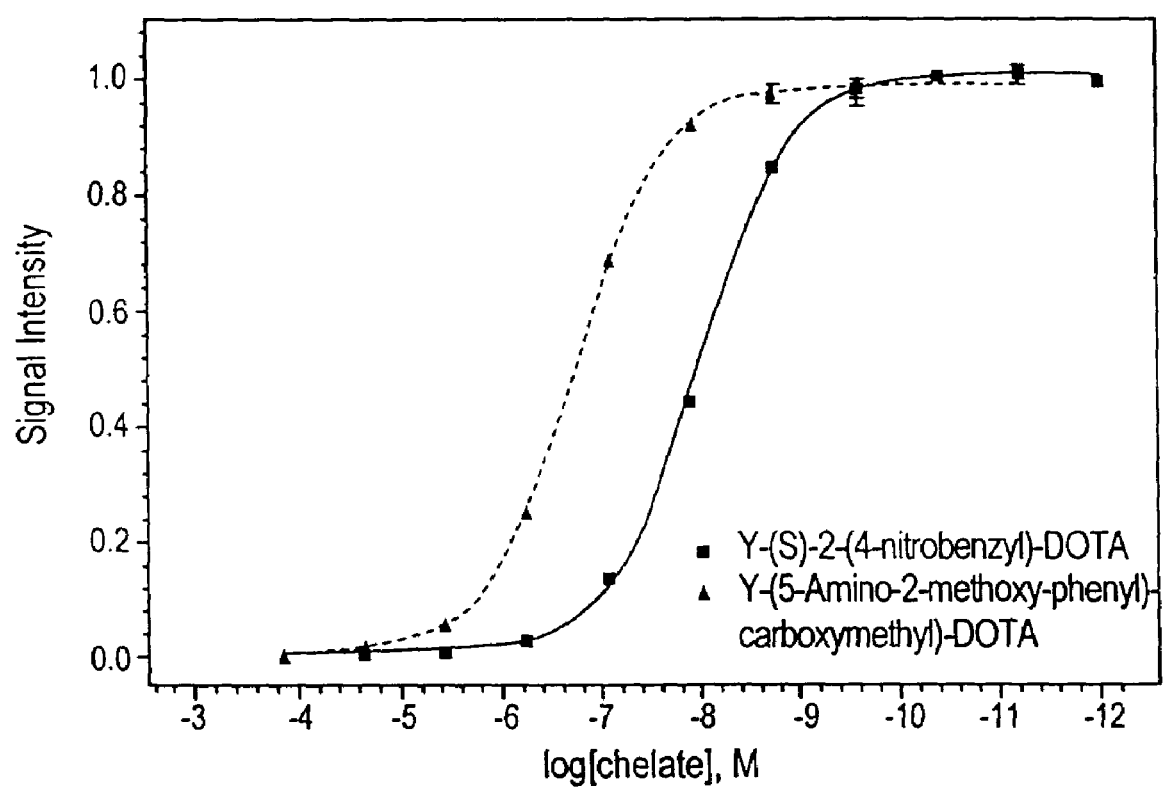
FIG. 15 is a graphical display showing the relative binding curves of 2D12.5 for Y-DOTA isomers and Y-DTPA. 2D12.5 binds both the (R)- and (S)- isomers of 2-(4-nitrobenzyl)-DOTA when the coordinated metal is $Y^{3+}$ (the same behavior is expected for the other rare earths). The (S)-isomer confers Λ-helicity, while the (R)-isomer confers Δ-helicity to the acetate arms. The Λ-helicity is observed in the crystal structure for 2D12.5 and is the preferred isomer for binding. However, the antibody tolerates the (R)-isomer with Δ-helicity, and the affinity decreases less than an order of magnitude as compared to the (S), Λisomer. Y-DOTA (no-sidearm) exists is solution as a racemic mixture of the coordination isomers. As expected, the binding affinity for racemic Y-DOTA is between that observed for the (S)- and (R)- isomers of 2-(4-nitrobenzyl)-DOTA.
Figure 16:
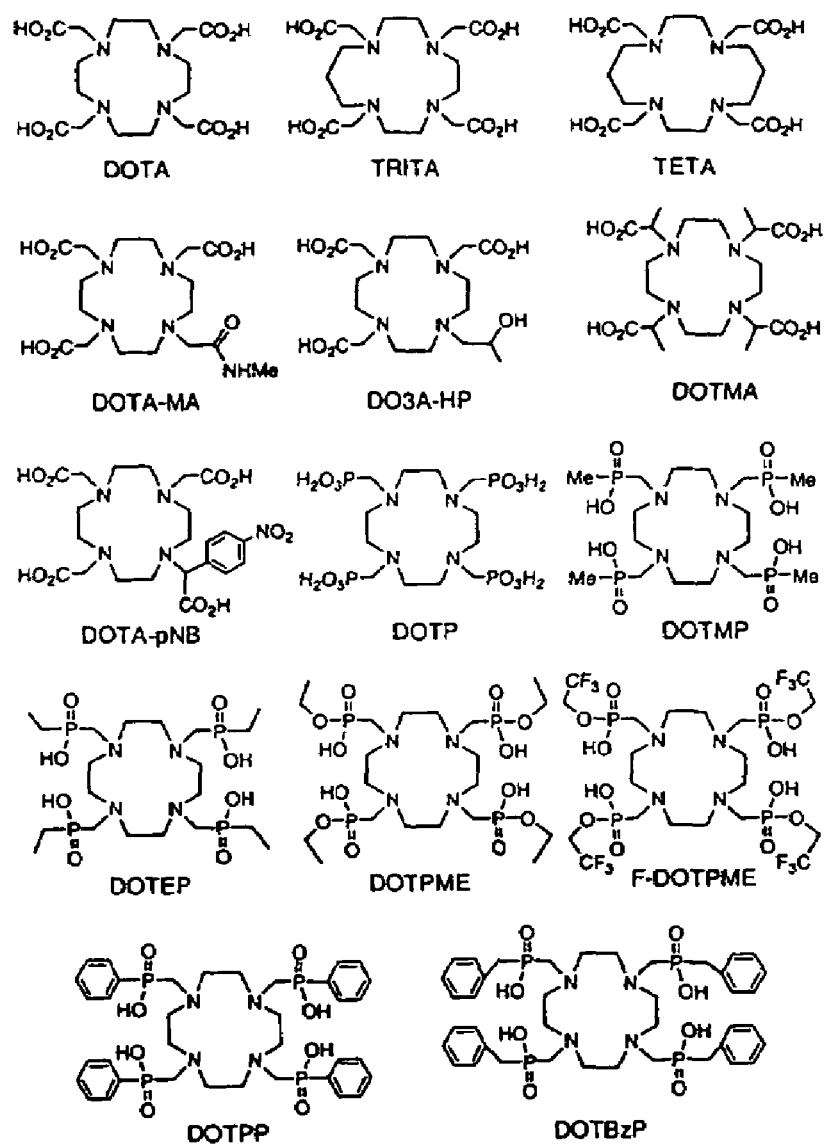
FIG. 16 shows exemplary ECAT reagents suitable for use in the methods of the invention.
Figure 12:
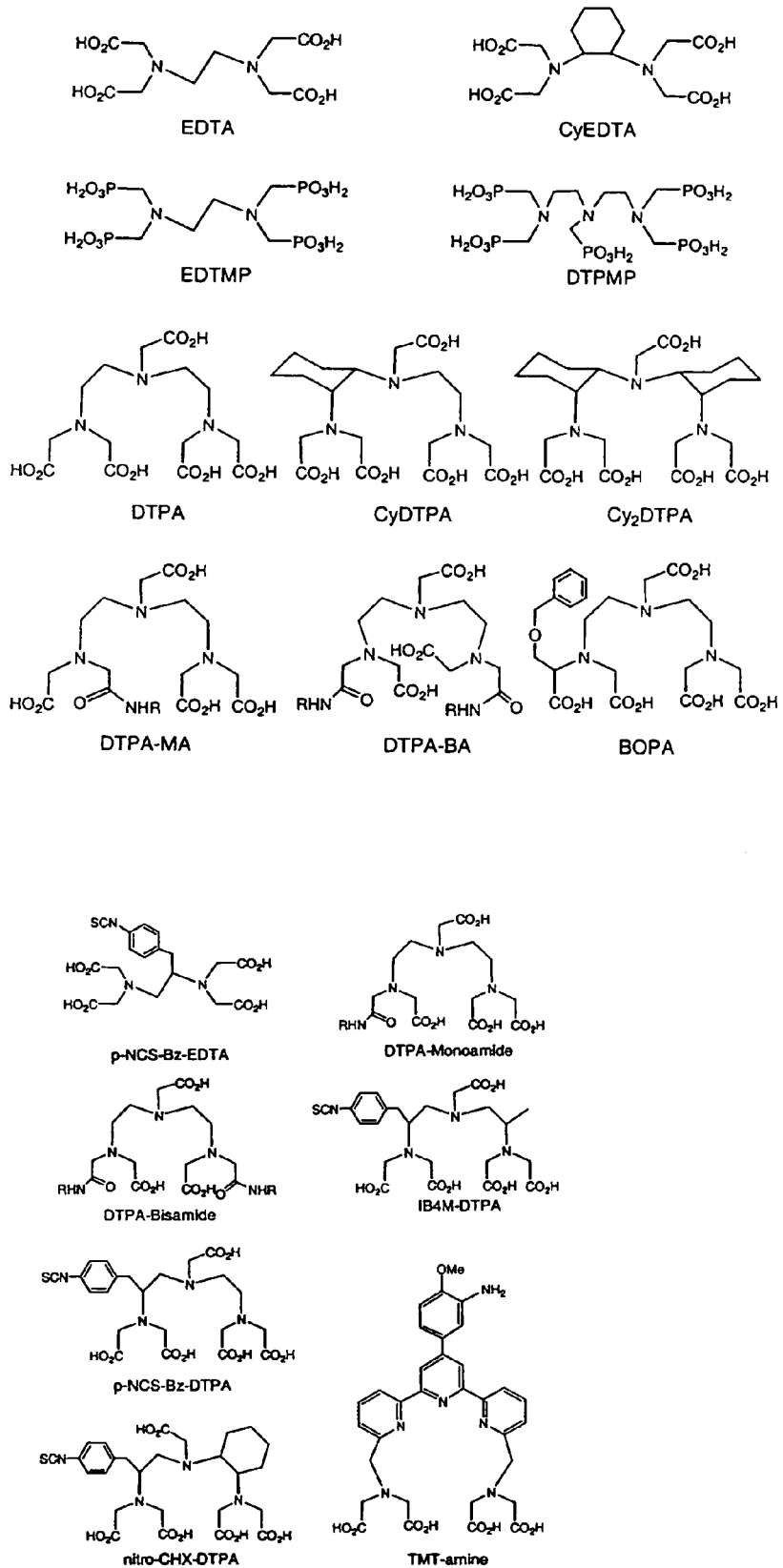

The relative binding affinities determined for each rare earth DOTA complex relative to Y-DOTA are plotted as $\Delta\Delta G$ values in FIG. 14. Out of 15 ions tested, we found six rare earth complexes with $\Delta\Delta G$ values more favorable for binding than the original $Y^{3+}$ complex. The radii of the nonacoordinate trivalent lanthanide ions vary in small increments across the series from 1.21 Å ($La^{3+}$) to 1.03 Å ($Lu^{3+}$) (see, e.g., Shannon, R. D. *Acta Crystallogr., Sect. A: Found. Crystallogr.* A32: 751-767 (1976)). Our results show that when the shape of the DOTA complex is perturbed by either increasing or decreasing the radius of the lanthanide ion, the stability of the protein-ligand complex changes in a regular fashion. The effect of the change in ion radius on the standard $\Delta G$ of binding should be described approximately by an equation of the form:

$$\frac{d\Delta G}{dr} = k|r - r_o| \text{ which integrates to } \Delta\Delta G = k(r - r_o)^2/2$$

The behavior of $\Delta\Delta G$ as a function of ionic radius fits a parabola, as might be expected for a system that behaves in a thermodynamically elastic way, obeying Hooke's law over a small range of perturbations. The quantitative binding differences allow us to assess the system's flexibility expressed as the force constant k, whose optimal value is $\approx 50$ $Nm^{-1}$, comparable to a chemical bond. The optimal ionic radius $r_o$ predicted from the parabolic fit to the binding data is 1.11 Å, close to the strongest binders $Tb^{3+}$, $Gd^{3+}$, and $Eu^{3+}$ (1.095, 1.107, and 1.120 Å).

Both Y-DOTA and Gd-DOTA are generally regarded as nonacoordinate, with 4 nitrogens and 4 oxygens from DOTA plus a single coordinated water molecule, in a capped square antiprism arrangement (denoted M). At equilibrium, rare earth DOTA complexes at either end of the lanthanide series differ in the layout of the acetate arms, and mixtures of isomers ranging from M to a distorted inverted antiprism (m) are observed for some. The ionic radius and geometry of the complex also affect the accessibility of the ninth coordination site for water (see, e.g., Aime et al., *Inorg. Chem.* 36: 2059-2068 (1997) and Cosentino et al., *Am. Chem. Soc.* 124: 4901-4909 (2002)). Large La-DOTA is almost exclusively isomer m, while small Lu-DOTA is predominantly isomer M. We suspect that these conformational equilibria play a role in the different binding affinities observed here. Even though $Sc^{3+}$ generally exhibits similar coordination geometries to the rare earths (see, e.g., Zhang et al., *Acta Crystallogr., Sect. C: Cryst. Struct. Commun.* 55: 1418-1420 (1999), Sc-DOTA does not fit well on the optimal parabola for the lanthanides, perhaps because it has a much smaller ionic radius (0.867 Å) (see, e.g., Meehan et al. *Chem. Rev.* 181: 121-145 (1999)).

The broad specificity and high affinity of the 2D12.5 antibody for all rare earth-DOTA complexes make it particularly interesting for applications that take advantage of the unique characteristics of lanthanides (see, e.g., Corneillie et al., *J. Am. Chem. Soc.* 125(49):15039-48 (2003). For example, Simeonov et al. have recently described bluefluorescent antibodies, potential sensors that change the emission of a stilbene ligand upon antibody binding (see, Simeonov, et al., *Science* 290: 307-313 (2000)). UV excitation of the Tb-DOTA-2D12.5 complex leads to energy transfer from aromatic side chains of the antibody to bound Tb-DOTA, enhancing green terbium luminescence by approximately four orders of magnitude relative to unbound Tb-DOTA. The enhancement is comparable to that observed for $Ca^{2+}$ binding proteins, which also transfer energy from aromatic side chains to $Tb^{3+}$ ions bound in $Ca^{2+}$ sites (see, e.g., Hogue et al., *J. Biol. Chem.* 267: 13340-13347 (1992)). Sensors based on lanthanide luminescence exhibit millisecond emission lifetimes, which makes them useful for a number of biological applications (see, e.g., Parker et al., *Chem. Rev.*, 102: 1977-2010 (2002)).

Example 4

This example describes affinity purification of metal-DOTA tagged peptides on a 2D12.5 aminolink gel affinity column.

4.1 Coupling of 2D12.5 Antibody to Aminolink Plus Coupling Gel

Approximately 19 mg of pure 2D12.5 antibody (6.4 mg/mL) was dialyzed into PBS, pH 7.2. The protein solution was then added to Aminolink gel that had been pre-equilibrated in PBS, pH 7.2 and agitated overnight at 4° C. 100 mM $NaCNBH_3$ (reducing agent) was then added and the mixture was agitated again for several hours. The column was then washed with PBS and unreacted sites on the gel were blocked and reduced with 1 M Tris, pH 7.4 and 100 mM $NaCNBH_3$. The column was then washed with PBS, preservative was added, and the column was stored at 4° C.

4.2 Affinity Purification of Metal-DOTA Tagged Peptides

After binding a mixture containing M-DOTA tagged species, the column is washed with a series of different solutions: high salt (e.g., ~1 M NaCl or similar), low pH (e.g., 0.1% TFA, pH 2), high pH (e.g., 0.1% TEAOAc, ~pH 10), and an organic additive wash containing less than or equal to 30% acetonitrile or equivalent. A neutral buffer or water is used between each of the above washes. A final wash of water is followed by elution of M-DOTA tagged species with an acidic solution containing acetonitrile or equivalent (e.g., 0.1% TFA in 20% acetonitrile).

In summary, the binding between antibody 2D12.5 and its high binding Metal-DOTA antigens are to be unaffected by varying pH alone (pH 1.5-12), high salt solutions (~1 M) or organic solvent additive conditions (approx 30% acetonitrile or less) where the pH is neutral. This allows for a variety of wash conditions to remove contaminating untagged species that may be present in a mixture. Elution of the tagged species can be accomplished with a combination solution of low pH and an organic additive (approx 20% acetonitrile or equiv.), but is not be limited to this elution condition exclusively.

Example 5

This example describes use of ECAT tags to identify the amino acid that participates in the formation of a permanent bond between G54C Fab and AABD.

Aliquots of mercaptoethylamine-activated G54C Fab were incubated separately with either Th-AABD or Tm-AABD and combined prior to digestion with chymotrypsin. Only the peptide containing the G54C engineered cysteine was labeled, and the ratio of Tb- and Tm-AABD labeled peptide was approximately equal as expected. MS2 analysis confirmed the sequence of the peptide and presence of either the Tb-AABD or Tm-AABD label. The labeled peptide was affinity purified with an immobilized 2D12.5 column prior to LC/MS analysis as described in, e.g., Whetstone et al., *Bioconjugate Chem.* 15:3-6 (2004). The Tb3+ and Tm3+ labels act as useful mass tags; the unnatural difference of 10 mass units between the Tb- and Tm-AABD labeled peptides greatly simplifies peptide identification and peptide purification prior to mass spectrometry analysis.

The MS/MS results demonstrate that the permanent covalent bond between the engineered ligand and G54C Fab is formed with the desired cysteine of the antibody.

Example 6

This example describes affinity purification of metal-DITC tagged peptides on a 2D12.5 affinity column.

Materials and Methods
1. Reagents
   400 µL HSA at 20 mg/mL in 0.1 M tetramethylammonium phosphate, pH 8.0 (Stock)
   300 µL DITC-Tb at 16.6 mM in 0.1M tetramethylammonium acetate, pH 6.0
   300 µL DITC-Tm at 16.6 mM in 0.1M tetramethylammonium acetate, pH 6.0
   Free amine test solution (5 g ninhydrin in 100 mL ethanol; 80 g liquefied phenol in 20 mL ethanol; 2 mL of 0.001 M aqueous potassium cyanide in 98 mL pyridine) mix three components in equal portions.
   Promega sequencing grade modified trypsin, frozen (Cat. No. V5113) triethylamine
   2D12.5 Ab affinity resin
2. Solutions:
   8 M urea in 0.1M tetramethylammonium phosphate, pH 8.0
   0.45 M DTT
   500 mM iodoacetamide
3. Buffers:
   100 mM ammonium bicarbonate, pH 8.0
   10 mM MOPS, 100 mM NaCl pH 7.2
   500 mM HEPES, pH=7.4 w/1M NaCl (10×stock soln)
   50 mM HEPES, pH=7.4 w/0.1M NaCl (L1)
   0.5% glacial acetic acid, pH≅3 (W1)
   50 mM HEPES, pH=7.4 w/0.1M NaCl and 20% acetonitrile (W2)
   0.4% trifluoroacetic acid with 50% acetonitrile (EH)
4. Labeling Human serum album (HSA) was dialyzed into 0.1M tetramethylammonium phosphate, pH 8.0 at 50 mg/mL. A portion of the dialyzed HSA was diluted to 20 mg/mL in the same buffer.

200 µL of the 20 mg/mL HSA solution was added to 300 µL of either 16.6 mM DITC-Tb or 16.6 mM DITC-Tm and the pH was adjusted to 9.0 with approximately 4 µL of triethylamine per reaction.

0.2 µL of each reaction was immediately spotted onto filter paper along with a positive (HSA at 8 mg/mL in 0.1M tetramethylammonium phosphate buffer at pH 9.0) and a negative control (buffer alone). The spots were allowed to dry and 0.5 µL of the ninhydrin test solution was spotted on top of the original spots. This was briefly heated with a hot air gun until a dark purple color developed on the positive control. Both reactions and the positive control elicited a dark purple color, while the negative control was light yellow.

The reaction solutions were placed at 37° C. and allowed to incubate for 2 hr. The ninhydrin test was repeated. The positive control was still dark purple, but both labeling reactions gave only a slight positive response to the color test.

5. Denaturation, Disulfide Reduction and Trypsinization

The two reactions were then mixed together and dialyzed into 10 mM MOPS, 100 mM NaCl pH 7.2. The final volume of the dialyzed protein solution was approximately 1.2 mL. The solution was transferred to a 1.5 mL eppendorf tube and brought to dryness in a speed-vac.

20 µL of ddH$_2$O, 40 µL of 8 M urea in 0.1 M tetramethylammonium phosphate, pH 8.0 and 4 µL of 0.45 M DTT were added to the dried protein and sonicated briefly until all salts and protein were in solution. The solution was then heated at 55° C. for 45 minutes. After cooling, 8 uL of a freshly prepared 500 mM solution of iodoacetamide in ddH$_2$O was added, the solution mixed, centrifuged briefly and incubated in the dark at room temperature for 20 min. The final volume of the protein solution was 72 µL. To this 428 µL of 0.1 M ammonium bicarbonate, pH 8.0 was added. (The protein was approximately 16 mg/mL) The pH was confirmed to be at 8.0 by indicator paper test.

20 µg of reconstituted trypsin was added to the labeled HSA solution. This mixture was incubated at 37° C. for 18 hr. An SDS-PAGE analysis of the tryptic digest indicated that the digestion was complete.

6. Purification of HSA Peptides with Immobilized 2D12.5 Ab Column

All volatile buffers are prepared fresh, in glass bottles before each experiment and the pH is verified before use. HEPES buffers were sterile filtered (0.22 µm) and stored at room temperature.

A. Buffers
   10×Load Buffer (10×L): 500 mM HEPES, pH=7.4 w/1 M NaCl.
   1×Load Buffer (L1): 50 mM HEPES, pH=7.4 w/0.1 M NaCl.
   Wash Buffer 1 (W1): 0.5% glacial acetic acid, pH≅3
   Wash Buffer 2 (W2): L1 with 25% acetonitrile
   Elute Buffer H (EH): 0.4% trifluoroacetic acid with 50% acetonitrile
   Sample Load Solution (SL): Approximately 800 ug (50 ul of 16 mg/ml) rHSA-DITC(Tb/Tm) digest and 500 ul of 10×L was brought to 5.0 ml total volume with ddH$_2$O.

B. Purification Procedure:
   1. Transfer 500 µl of 2D12.5 immobilized resin slurry to a 2 ml column (Pierce #29920) with both a top and bottom frit according to manufacturer's protocol. This should result in approximately a 250 µl column.
   2. Equilibrate the column with 12-16 CVs (3-4 ml) of L1.
   3. Load sample SL (5.0 ml) onto column and let drain by gravity flow in 5×1.0 ml fractions.
   4. Wash column with 2×1.0 ml fractions of L1.
   5. Wash column with 2×1.0 ml fractions of W1.
   6. Wash column with 2×1.0 ml fractions of W2.
   7. Add 1×500 µl of EH and collect flow through.
   8. Cap column and incubate at room temperature for at least 15 minutes.
   9. Uncap column, and collect 5×500 µl elution fractions. The first fraction after incubation typically contains the majority of tagged peptides.

10. All elution fractions were immediately neutralized with 3 μl of triethylamine and stored at −20° C. for less than 12 hrs before being analyzed by MS.

Typically flow through of buffer EH in step 7 should occur in <30 sec to maximize peptide concentration in the elution step 9.

C. LC/MS Analysis

100 μL of the elution fraction from step 9 was examined by LC/MS for the presence of tagged peptides. HPLC was performed using a Waters Atlantis C18 3 μm 2.1×100 mm column (part no. 186001295), eluted with a linear gradient of (B) 0.175% formic acid/acetonitrile in (A) 0.2% formic acid/water at a flow rate of 250 μL/min. Injections were made at 5% B, the solvents held at 5% for 5 minutes (flow off the column was diverted to waste to allow removal of buffer salts before sending sample to the mass spectrometer). The gradient was ramped to 55% B over 120 minutes, then to 100% B over an additional 25 min. The column was then washed and re-equilibrated before the next run. Mass spectrometry was performed on a ThermoFinnigan LCQDeca electrospray ion-trap instrument.

Example 7

This example describes detection of multiple oxidized sites on human serum albumin using (((S)-2-(4-(2-aminooxy)-acetamido)-benzyl)-1,4,7,10-tetraazacyclododecane-N,N',N'',N'''-tetraacetic acid (AODOTA), loaded with monoisotopic rare earths.

Oxidized sites on the protein, both pre-existing and FeEDTA/ascorbate-induced, are tagged by imine formation between protein aldehyde or keto groups and (((S)-2-(4-(2-aminooxy)-acetamido)-benzyl)-1,4,7,10-tetraazacyclododecane-N,N'N''N'''-tetraacetic acid (AODOTA), loaded with monoisotopic rare earths, e.g., Tb and Ho. The protein is then trypsinized and tagged peptides are isolated with an element-independent lanthanide-DOTA antibody 2D12.5 column. Our nanoLC-FTICR analysis platform consists of a prototype Eksigent nanoLC pump that delivers a 100 nL/min gradient through in-house C18 packed pulled glass capillary nanospray tips to a Bruker Apex 9.4T FTMS. Accurate mass peaks which show the characteristic mass difference between Tb and Ho are compared to an in silico tryptic digest of oxidized and tagged HSA, before being mapped onto the HSA crystal structure.

Figure 20:
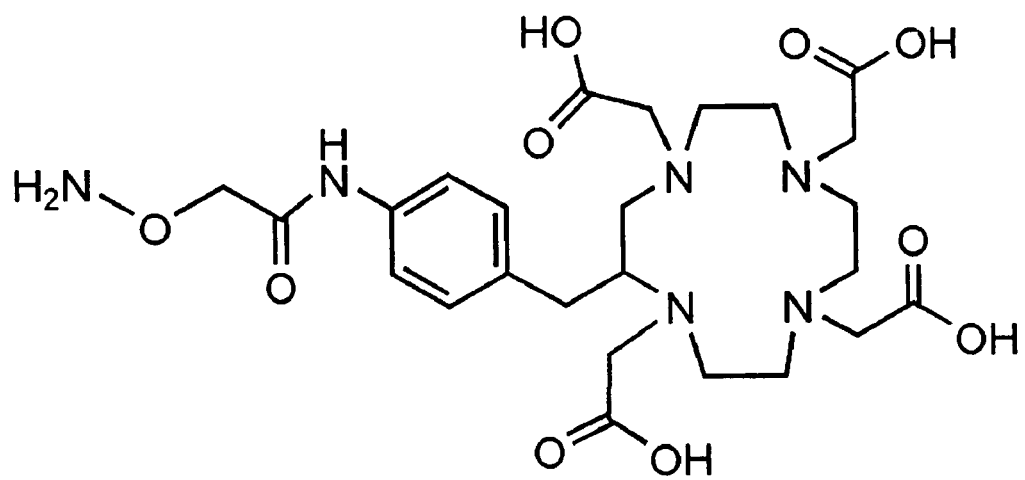
FIG. 20 depicts the structure of AODOTA or AOD.
Figure 21:
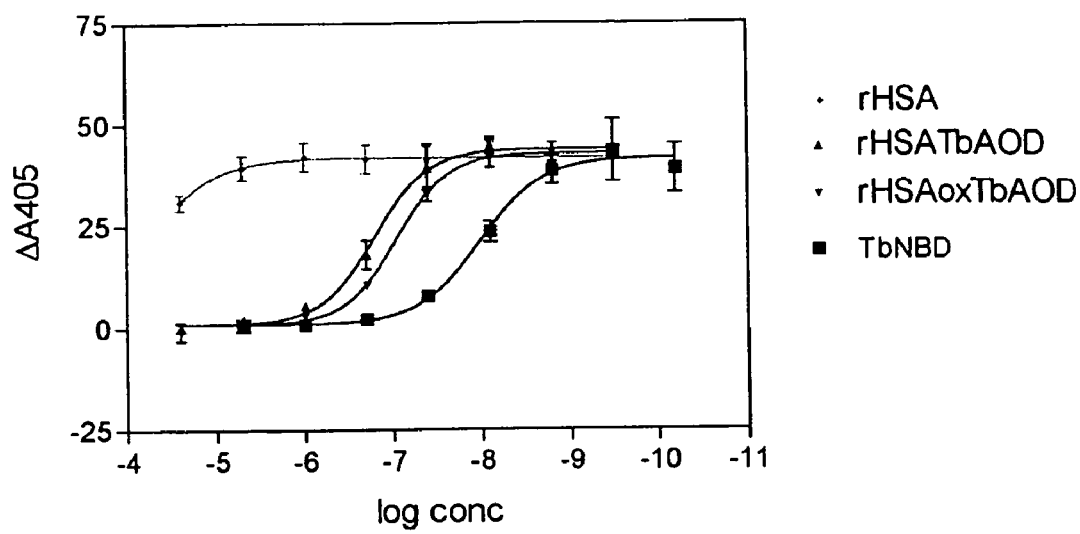
FIG. 21 depicts results from a competitive DOTA ELISA showing the tagging yield on the control rHSA TbAOD and the rHSA oxidized with FeEDTA and ascorbate (rHSAoxTbAOD). The concentration on the horizontal axis represents either protein concentration (moles/liter) or TbNBD concentration (moles/liter). The control sample showed 1 in 16 proteins tagged with TbAOD while the oxidized sample had 1 in 9 proteins tagged with TbAOD.
Figure 23:
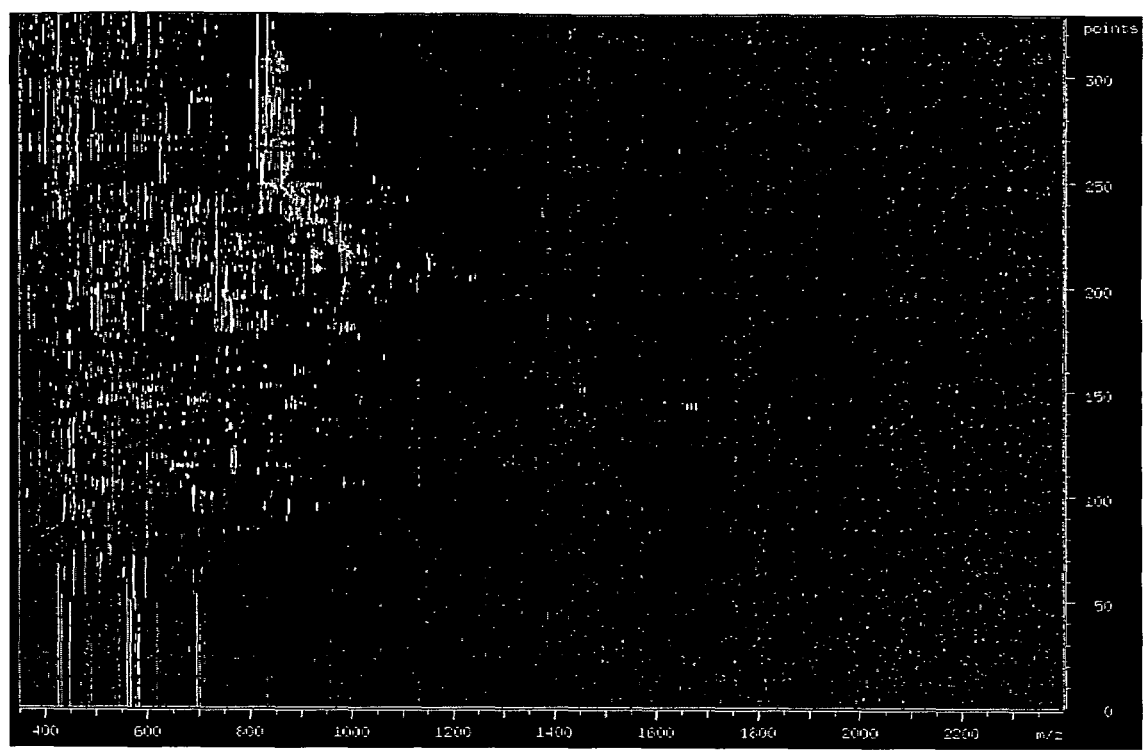

The reagent (((S)-2-(4-(2-aminooxy)-acetamido)-benzyl)-1,4,7,10-tetraazacyclododecane-N, N', N'', N'''-tetraacetic acid (AOD, FIG. 20) reacts with a carbonyl group to covalently attach to the protein oxidation site. The Element-Coded Affinity Tag can be loaded with any of a variety of lanthanide metals to allow for parallel analysis of control and experimental samples and to allow for direct comparison and quantitation. Tagged tryptic peptides are isolated by affinity capture and examined directly in the mass spectrometer, providing in a single experiment not only identification of the protein and quantitation of the oxidation level, but also identification of the specific position in the protein that has been oxidized. The technology can be applied to characterize and compare multiple sites of oxidation in a protein or proteins, potentially leading to disease-specific patterns with diagnostic utility.

This methodology is illustrated using a model protein, recombinant human serum albumin (rHSA). The approach can be applied not only to other proteins, but also to carbohydrates, lipids, and other biological molecules.

Tagging

Aliquots of rHSA[1] in 1×cleavage buffer [10 mM MOPS, 120 mM NaCl, 10 mM $MgCl_2$, 1 mM EDTA, pH 7.9] were subjected to oxidation with 20 mM FeEDTA and 20 mM ascorbate while the control had no oxidants added. The oxidation reaction was mixed and allowed to proceed at RT for 15 min before being dialyzed into tagging buffer [100 mM $KH_2PO_4$, 0.5M NaCl, pH 6.5]. The rHSA was then split into two aliquots and labeled with either equimolar ThAOD/HoAOD or ThAOD/TmAOD at RT overnight. The reactions were then dialyzed into 50 mM HEPES, pH 7.5. Aliquots were taken for the gels, blots, and ELISA before the remaining protein was reduced, alkylated with iodoacetamide, and trypsin digested.

[1] ABBREVIATIONS: 2IT, 2-iminothiolane; AOD, ((S)-2-(4-(2-amninooxy)-acetamido)-benzyl)-1,4,7,10-tetraazacyclododecane-N,N',N'', N'''-tetraacetic acid; AP, alkaline phosphatase; BAD, ((S)-2-(4-(2-bromo)-acetamido)-benzyl)-1,4,7,10-tetraazacyclododecane-N,N',N'',N'''-tetraacetic acid; NBD, (S)-2-(4-nitro-benzyl)-1,4,7,10-tetraazacyclododecane-N,N',N'',N'''-tetraacetic acid; PNPP, p-nitrophenyl phosphate; rHSA, recombinant human serum albumin; TEAOAc, triethylammonium acetate.

Tag Confirmation

Duplicate Invitrogen 10-20% Tris-glycine gels were run for 1.5 hr at 125V in Laemmli buffer [25 mM Tris, 192 mM glycine, 0.1% SDS]. One gel was blotted with a 1:5,000 dilution of the primary antibody, 1 mg/mL anti-metal chelate antibody 2D12.5, and a 1:2,000 dilution of the secondary antibody, a goat anti-mouse lambda-AP conjugate. The western blot was visualized using an HP5490c scanner. The other gel was stained with SYPRO Ruby and imaged using the Biorad ChemXRS imager, following manufacturer's instructions. The gel confirmed that the same amount of protein was loaded into each lane while the blot showed only the M-AOD tagged proteins. Though this Western blot is only qualitative, the same technique could be used, in conjunction with protein standards and a linear detection method to determine quantitatively the tagging yield.

Competitive ELISA

ABBREVIATIONS:

2IT, 2-iminothiolane; AOD, ((S)-2-(4-(2- aminooxy)-acetamido)-benzyl) -1, 4, 7, 10-tetraazacyclododecane-N, N', N'', N'''-tetraacetic acid; AP, alkaline phosphatase; BAD, (S)-2-(4-(2-bromo)-acetamido)-benzyl)-1, 4, 7, 10-tetraazacyclododecane-N, N', N'', N'''- tetraacetic acid; NBD, (S)-2-(4-nitro-benzyl)-1, 4, 7, 10-tetraazacyclododecane-N, N', N'', N'''-tetraacetic acid; PNPP, p-nitrophenyl phosphate; rHSA, recombinant human serum albumin; TEAOAc, triethylammonium acetate.

Clear, high-binding plates were coated with 0.3 pmol of HSA-2IT-Y-BAD in 50 mM $Na_2CO_3$ (pH 9.6) and stored at 4C o/n. Wells were emptied and rinsed 3x with TBST (Tris-buffered saline w/0.05% Tween-20, pH 7.4). The wells were then blocked with 200 uL of 1% BSA in TBS (24.8 mM Tris, 137mM NaC1, 0.269 mM KC1, pH 7.4), at 37C for 2hr. 25 uL of competitor (M-NBD) or 25 uL of the tagged protein, at the appropriate concentrations, were then added to the wells with 25 uL of 2nM anti-DOTA antibody 2D12.5. The plate was incubated at RT for 1hr with mixing. The wells were rinsed 3x with TBST and then 50 uL of 1:4,000 dilution of goat anti-mouse lambda-AP was added to all wells. The plate was again incubated at RT for 1hr with mixing. The plate was rinsed 3x with TBST and 1x with 10mM diethanolamine, 0.5 mM $MgCl_2$, pH 9.5. 200 uL of a 1 mg/mL solution of PNPP in the diethanolamine solution was then added to the wells. The plate was read at RT for 30min, using a kinetic reading every minute. See FIG. 22 for the resulting curves for the rHSA TbAOD and the (FeEDTA/ascorbate oxidized) rHSA TbAOD. Comparing these curves with the standard curve using T bNBD, the labeling yield was calculated to be 1 in 16 proteins for the control sample and 1 in 9 for the FeEDTA/ascorbate oxidized sample.

Note that alternative ELISA techniques could also be tested to determine the tagging yield. One example is a sandwich ELISA where the anti-metal chelate antibody 2D12.5 is immobilized onto a 96-well plate. A dilution of the sample is then added to the wells and detected using a constant amount of appropriate secondary-antibody enzyme conjugate such as anti-human serum albumin-alkaline phosphatase.

Trypsin Digestion to Identify Specific Sites of Cleavage

The trypsin protocol was as follows: 1) reduce protein with 5 M urea, 0.125 M HEPES, pH 7.5, 28 mM DTT for 45 min at 37 C, 2) alkylate the cysteines by adding iodoacetamide to a final concentration of 56 mM and incubating at RT, in the dark, for 20 min, 3) reduce the concentration of the urea to 1 M using 50 mM HEPES, pH 7.5 and add $CaCl_2$ to a final concentration of 1 mM, and 4) add trypsin (1:50 wt:wt ratio) and incubate at 37 C overnight.

Affinity Purification of ECA T-tagged Peptides

After the trypsin digestion, the two differentially labeled samples were combined and loaded onto 2D12.5 aminolink resin that had been equilibrated with loading buffer [25 mM TEAOAc, pH 7]. The flowthrough was collected before beginning the wash cycle. All washes were 6 times two column volumes with two column volumes of loading buffer between each wash, except after the first and last washes. The washes were wash 1—loading buffer, wash 2—25 mM TEAOAc, 1 M NaCl, pH 7, wash 3—0.5% acetic acid, pH 2.8, wash 4—4M urea, wash 5—25 mM TEAOAc, 10% acetonitrile. The tagged peptides were then eluted with 10×2 column volumes of 50% acetonitrile/0.4% trifluoroacetic acid. Elution fractions were combined and dried using the speed-vac.

LC-MS

The tagged, digested, and affinity purified samples were analyzed by reversed phase nano-Liquid Chromatography-Fourier Transform Ion Cyclotron Resonance Mass Spectrometry (nanoLC-FTICRMS). A prototype binary nanoLC pump (Eksigent Technologies) was used to load affinity elutions onto a 10 cm in-house packed C18 fused silica column. The gradient of A (10 mM ammonium acetate, 0.1% formic) to B (0.1% formic in acetonitrile) was from 10-50% B over 40 min. Column effluent was directly interfaced with a home-built nanospray source into a Bruker Apex 9.4T FTMS. Note that the different metallated peptides elute together and provide easy identification of peptides of interest. Also, a comparison of the isotopic distribution of the co-eluting peptide-tag pair allows identification of the charge state and parent masses; here, the m/z difference of 3 indicates that both tagged peptides are in the +2 charge state.

Data Analysis

Figure 24:
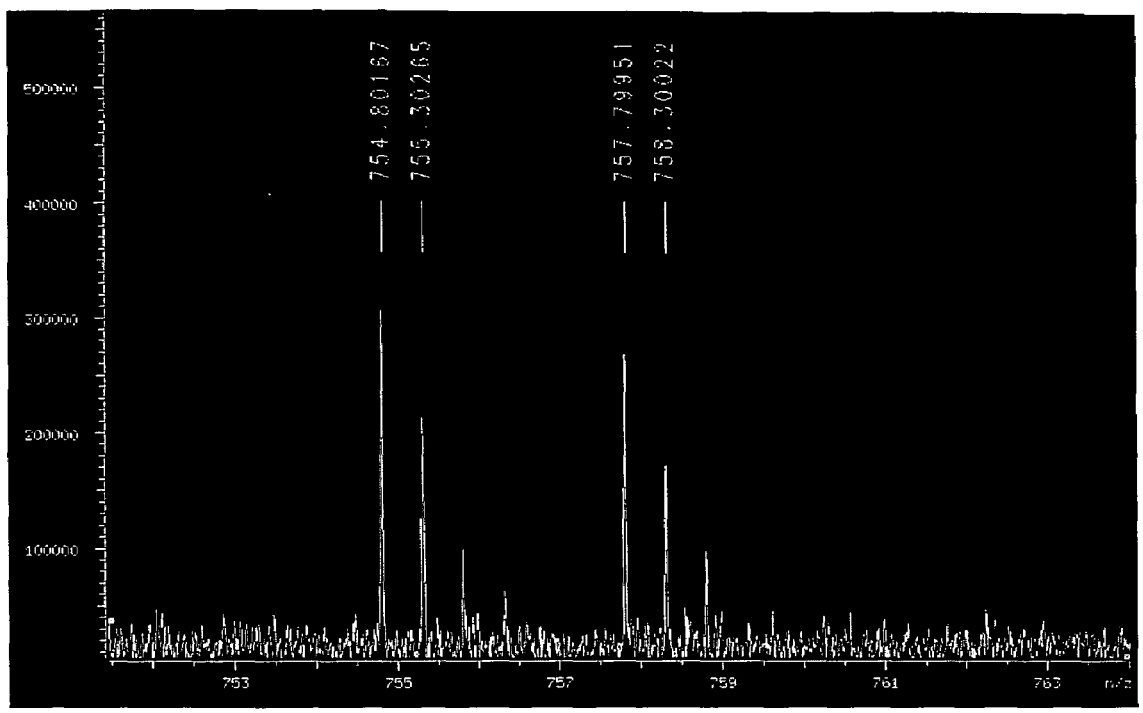
FIG. 24 shows a FTMS spectrum showing a doubly charged mass pair. The peaks shown correspond to the peptide, AAC*LLP*K (SEQ ID NO:46), with the cysteine alkylated with iodoacetamide and the proline tagged with TbAOD and HoAOD. See Table 1A (FIG. 25).

To identify the tagged peptides, mass spectral data was compared to an in silico rHSA digest that was modified with alkylated cysteines and possible oxidation and tagging modifications. The mass spectrum from one of the control peptides is shown in FIG. 24. In this spectra, the high resolution of the FT-ICR instrument can be seen and this spectrum was found to correspond to the AAC*LLP*K (SEQ ID NO:46) peptide. Each asterisk denotes modification: on this peptide, the cysteine has been alkylated with iodoacetamide and the proline has been oxidized and tagged with M-AOD. Using this method, 4 tryptic peptides were identified in the control sample and 8 tryptic peptides (including 2 of the 4 control peptides) were identified in the FeEDTA/ascorbate oxidized sample (see Tables 1A and 1B in FIG. 25).

It is noteworthy that a variety of residues, including lysine, arginine, and proline, are found to be oxidized and tagged with this method. All of the peptides have been verified using another rHSA sample and different metals. These peptides are mapped onto an HSA crystal structure 1AO6 (www.rcsb.org).

Using this methodology we have detected and identified multiple peptides containing oxidized lysine, arginine, or proline residues on recombinant HSA. Specifically, 4 sites of background oxidation were identified from control sample; 8 sites of induced oxidation were identified (2 in common with control); a variety of residues were identified as oxidized and tagged—lysine, arginine, proline; all identified peptides were identified as true tryptic peptides; and all identified peptides mapped onto the surface of the HSA crystal structure. All of the tagged HSA peptides identified contain the characteristic mass signature from the rare earth pair and have been mapped to the protein surface. The background oxidation data, from a commercially available recombinant protein, validates our technology for finding oxidation sites. The utility of this technique is further corroborated with the FeEDTA/ascorbate oxidized data. The results give us a rough map of the exposed surface of HSA, which is consistent with the crystal structure data.

We have demonstrated that by using novel tagging technologies, in combination with multidimensional separation and high-resolution mass spectrometry, we can increase the specificity and dynamic range of our analysis to the point where we expect to be able to extract oxidation site information from complex biological mixtures at biologically relevant levels. The use of novel analyte-specific synthetic chemistry with complementary affinity chromatography allows us to extract the components of interest while also offering the advantage of characteristic mass tags. Although the complexity of the sample has been reduced, the analytes of interest are still minor components of a complex mixture. Using nanoLC we are able to achieve a greater than 100 fold concentration of each remaining component while increasing the dynamic range by chromatographically resolving the mixture before using the high resolution of the FTICR to detect the co-eluting isotopic pairs with high specificity. In the final analysis it is these isotopic tags which allow us to extract the relevant information out of what remains a very complex LC-MS map.

Thus, the compositions and methods described herein can be used to detect oxidized biomolecules, quantify oxidized biomolecules, and to identify sites of oxidation in biomolecules.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A method for detecting oxidation patterns of an oxidized biomolecule, said method comprising:

(a) contacting a biological sample suspected of containing an oxidized biomolecule with a tag moiety comprising a macrocyclic chelating agent complexed to a metal ion, wherein the macrocyclic chelating agent has the formula (Ia):

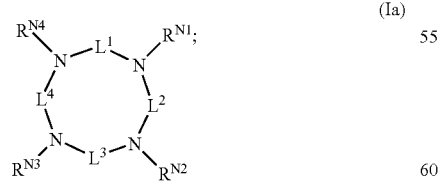

wherein each of $L^1$, $L^2$, $L^3$ and $L^4$ are linking groups independently selected from $C_{2-5}$ alkylene which is optionally substituted with one to three substituents selected from the group consisting of substituted and unsubstituted alkyl, substituted and unsubstituted heteroalkyl and substituted and unsubstituted aryl;

each of $R^{N1}$, $R^{N2}$, $R^{N3}$ and $R^{N4}$ are independently selected from the group consisting of substituted and unsubstituted alkyl, substituted and unsubstituted heteroalkyl and substituted and unsubstituted aryl;

wherein at least one of $L^1$, $L^2$, $L^3$, $L^4$, $R^{N1}$, $R^{N2}$, $R^{N3}$ and $R^{N4}$ comprises a functional group that forms a covalent linkage at an oxidized site on said oxidized biomolecule, thereby forming an adduct between said oxidized biomolecule and said tag moiety;

(b) contacting said adduct with an affinity medium comprising a first binding moiety that binds said tag moiety;

(c) eluting said adduct from said affinity medium, thereby forming a solution comprising said adduct; and (d) detecting the adduct by detecting the weight of the adduct comprising the metal ion in the tag moiety of step (c), thereby detecting the oxidation pattern of the biomolecule.

2. The method according to claim 1, wherein said biological sample is isolated from an individual suspected of having a disease selected from the group consisting of: a neurodegenerative disorder, a neoplastic disorder, a vascular disorder, and an autoimmune disorder.

3. The method according to claim 1, wherein said oxidized biomolecule is selected from the group consisting of: a polypeptide, a lipid, a glycoprotein, and a nucleic acid.

4. The method according to claim 3, wherein said oxidized biomolecule is a polypeptide.

5. The method according to claim 1, wherein said metal ion is selected from a lanthanide ion, an actinide ion, an alkaline earth metal ion, a transition metal ion, and a post transition metal ion.

6. The method according to claim 1, wherein said quantity of said adduct is determined by mass spectrometry.

7. The method according to claim 1, wherein detecting said oxidized biomolecule detects the quantity of said oxidized biomolecule in said biological sample.

8. The method according to claim 1, wherein detecting said oxidized biomolecule detects an oxidation site within said oxidized biomolecule in said biological sample.

9. The method according to claim 1, wherein said macrocyclic chelating agent comprises four nitrogen atoms.

10. The method according to claim 1, wherein said macrocyclic chelating agent has Formula Ia':

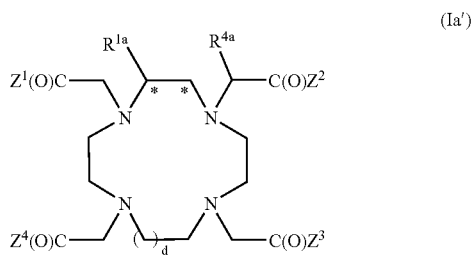

wherein
$Z^1$, $Z^2$, $Z^3$ and $Z^4$ are members independently selected from $OR^1$ and $NR^1R^2$
in which
$R^1$ and $R^2$ are members independently selected from H, substituted or unsubstituted alkyl and substituted or unsubstituted heteroalkyl;
$R^{1a}$ and $R^{4a}$ are members independently selected from H, substituted or unsubstituted alkyl, substituted or unsubstituted heteroalkyl; substituted or unsubstituted aryl and linker moieties;
wherein at least one of $R^1$, $R^2$, $R^{1a}$, $R^{4a}$ comprise said functional group; and
d is 1 or 2.

11. The method according to claim 10, wherein $R^{1a}$ or $R^{4a}$ comprises a moiety having Formula (Ia"):

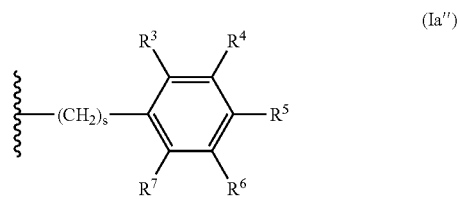

wherein
$R^3$, $R^4$, $R^5$, $R^6$ and $R^7$ are members independently selected from H, halogen, $NO_2$, CN, $X^1R^8$, $NR^9R^{10}$, and $C(=X^2)R^{11}$ wherein
$X^1$ is a member selected from O, NH and S;
$R^8$ and $R^9$ are members independently selected from H, substituted or unsubstituted alkyl, substituted or unsubstituted heteroalkyl and $C(X^3)R^{12}$
wherein
$X^3$ is a member selected from O, S and NH;
$R^{12}$ is a member selected from substituted or unsubstituted alkyl, substituted or unsubstituted heteroalkyl and $OR^{13}$
wherein
$R^{13}$ is a member selected from substituted or unsubstituted alkyl, substituted or unsubstituted heteroalkyl, substituted or unsubstituted aryl and substituted or unsubstituted heteroaryl;
$R^{10}$ is a member selected from H, substituted or unsubstituted alkyl, substituted or unsubstituted heteroalkyl and OH,
and $R^9$ and $R^{10}$, taken together are optionally (=C=S);
$X^2$ is a member selected from O, S and NH; and
$R^{11}$ is a member selected from H, halogen, substituted or unsubstituted alkyl, substituted or unsubstituted heteroalkyl, $OR^{14}$, $NR^{15}R^{16}$
wherein
$R^{14}$ is a member selected from H, substituted or unsubstituted alkyl, substituted or unsubstituted heteroalkyl, and $C(O)R^{17}$
wherein
$R^{17}$ is a member selected from substituted or unsubstituted alkyl and substituted or unsubstituted heteroalkyl;
$R^{15}$ and $R^{16}$ are members independently selected from H, substituted or unsubstituted alkyl and substituted or unsubstituted heteroalkyl; and
s is 0, 1, 2, 3, or 4.

12. The method according to claim 1, wherein said chelating agent is a member selected from substituted or unsubstituted DOTA, and substituted or unsubstituted TETA.

13. The method according to claim 1 wherein said first binding moiety is a polypeptide.

14. The method according to claim 13, wherein said polypeptide is an antibody.

15. The method according to claim 14, wherein said antibody specifically binds to a metal chelate.

16. The method according to claim 15, wherein said antibody comprises a VL and VH chain, wherein the VL chain is selected from the group consisting of SEQ ID NO: 1, 21, 22 and 23 and the VH chain is selected from the group consisting of SEQ ID NO: 5, 9, 10, 11, 12, 13 and 14.

17. The method according to claim 1, wherein said tag moiety further comprises a second binding moiety that is complementary to said first binding moiety.

18. The method according to claim 17, wherein said second binding moiety is a polypeptide.

19. The method according to claim 17, wherein said second binding moiety is biotin.

20. The method according to claim 1, further comprising detecting the oxidation pattern of said oxidized biomolecule in a second biological sample by
(e) contacting a second biological sample suspected of containing said oxidized biomolecule with a second tag moiety comprising a macrocyclic chelating agent complexed to a second metal ion, wherein the macrocyclic chelating agent comprises a functional group that forms a covalent linkage at an oxidized site on said oxidized biomolecule and wherein the macrocyclic chelating agent has the formula (Ia):

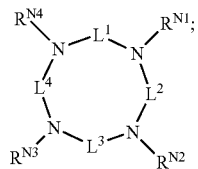

(Ia)

wherein
each of $L^1$, $L^2$, $L^3$ and $L^4$ are linking groups independently selected from $C_{2-5}$ alkylene which is optionally substituted with one to three substituents selected from the group consisting of substituted and unsubstituted alkyl, substituted and unsubstituted heteroalkyl and substituted and unsubstituted aryl;
each of $R^{N1}$, $R^{N2}$, $R^{N3}$ and $R^{N4}$ are independently selected from the group consisting of substituted and unsubstituted alkyl, substituted and unsubstituted heteroalkyl and substituted and unsubstituted aryl;
wherein at least one of $L^1$, $L^2$, $L^3$, $L^4$, $R^{N1}$, $R^{N2}$, $R^{N3}$ and $R^{N4}$ comprises said functional group, thereby forming a second adduct between said oxidized biomolecule and said second tag moiety;
(f) contacting said second adduct with the affinity medium;
(g) eluting said second adduct from said affinity medium, thereby forming a solution comprising said adduct; and
(h) detecting the second adduct by detecting the weight of the second adduct comprising the metal ion in the second tag moiety of step (g), thereby detecting the pattern of oxidation of the biomolecule in the second biological sample.

21. The method according to claim 20, wherein said first sample and said second sample are isolated from the same individual.

22. The method according to claim 20, wherein said first sample and said second sample are isolated from an individual suspected of having a disease selected from the group consisting of: a neurodegenerative disorder, a neoplastic disorder, a vascular disorder, and an autoimmune disorder.

23. The method according to claim 20, wherein said first sample and said second sample are isolated from an individual being treated for a disease selected from the group consisting of: a neurodegenerative disorder, a neoplastic disorder, a vascular disorder, and an autoimmune disorder.

24. The method according to claim 20, wherein said first sample is isolated from a tissue suspected of being diseased and said second sample is from a nondiseased tissue.

25. The method according to claim 20, wherein said first metal ion and said second metal ion are members independently selected from a lanthanide ion, an actinide ion, an alkaline earth metal ion, a transition metal ion, and a post transition metal ion.

26. The method according to claim 20, wherein said quantity of first adduct and said second adduct is determined by mass spectrometry.

27. The method according to claim 19, wherein said first binding moiety is streptavidin.

* * * * *